US008088578B2

(12) United States Patent
Hua et al.

(10) Patent No.: US 8,088,578 B2
(45) Date of Patent: *Jan. 3, 2012

(54) METHOD OF DETECTING AN ANALYTE

(75) Inventors: Zhishan Hua, Raleigh, NC (US); Michael G. Pollack, Durham, NC (US)

(73) Assignee: Advanced Liquid Logic, Inc., Research Triangle Park, NC (US)

( * ) Notice: Subject to any disclaimer, the term of this patent is extended or adjusted under 35 U.S.C. 154(b) by 135 days.

This patent is subject to a terminal disclaimer.

(21) Appl. No.: 12/546,253

(22) Filed: Aug. 24, 2009

(65) Prior Publication Data
US 2009/0311713 A1    Dec. 17, 2009

Related U.S. Application Data

(63) Continuation of application No. PCT/US2009/043774, filed on May 13, 2009.

(60) Provisional application No. 61/052,885, filed on May 13, 2008, provisional application No. 61/098,860, filed on Sep. 22, 2008, provisional application No. 61/108,880, filed on Oct. 28, 2008, provisional application No. 61/115,654, filed on Nov. 18, 2008, provisional application No. 61/141,820, filed on Dec. 31, 2008, provisional application No. 61/153,598, filed on Feb. 18, 2009, provisional application No. 61/160,607, filed on Mar. 16, 2009, provisional application No. 61/103,332, filed on Oct. 7, 2008.

(51) Int. Cl.
*C12Q 1/68* (2006.01)
*C12M 1/00* (2006.01)
*G01N 15/06* (2006.01)

(52) U.S. Cl. ............... 435/6.1; 435/91.2; 435/283.1; 435/285.2; 435/288.7; 422/68.1; 422/82.05; 422/502; 422/504; 536/23.1

(58) Field of Classification Search .................. None
See application file for complete search history.

(56) References Cited

U.S. PATENT DOCUMENTS
5,038,852 A    8/1991    Johnson et al.
(Continued)

FOREIGN PATENT DOCUMENTS
WO    WO2004073863 A2    9/2004
(Continued)

OTHER PUBLICATIONS

Wang et al "Efficient in-droplet separation of magnetic particles for digial microfluidics" J. Micromech. Microeng. 2007, 17:2148-2156.*

(Continued)

*Primary Examiner* — Betty Forman
(74) *Attorney, Agent, or Firm* — William A. Barrett; Ward and Smith, P.A.

(57) ABSTRACT

The invention relates to certain novel approaches to reducing or eliminating the movement of contaminants from one droplet to another on a droplet actuator via liquid filler fluid. In one application, a method of detecting an analyte is provided and includes providing in a detection window a droplet including a signal-producing substance indicative of the presence and/or quantity of an analyte and one or more magnetically responsive beads which may interfere with signal produced by the signal producing substance. The method further includes using a magnetic field for magnetically removing the magnetically responsive beads from the detection window and/or magnetically restricting the magnetically responsive beads from entering the detection window while transporting and/or retaining the droplet in the detection window. The method additionally includes detecting a signal produced by the signal-producing substance.

14 Claims, 56 Drawing Sheets

U.S. PATENT DOCUMENTS

| | | | |
|---|---|---|---|
| 5,176,203 | A | 1/1993 | Larzul |
| 5,498,392 | A | 3/1996 | Wilding et al. |
| 5,720,923 | A | 2/1998 | Haff et al. |
| 5,779,977 | A | 7/1998 | Haff et al. |
| 5,827,480 | A | 10/1998 | Haff et al. |
| 6,033,880 | A | 3/2000 | Haff et al. |
| 6,180,372 | B1 | 1/2001 | Franzen |
| 6,294,063 | B1 | 9/2001 | Becker et al. |
| 7,579,172 | B2 | 8/2009 | Cho et al. |
| 2004/0086870 | A1 | 5/2004 | Tyvoll et al. |
| 2004/0180346 | A1 | 9/2004 | Anderson et al. |
| 2005/0056569 | A1* | 3/2005 | Yuan et al. ............ 209/215 |
| 2005/0106742 | A1 | 5/2005 | Wahl |
| 2005/0227264 | A1 | 10/2005 | Nobile et al. |
| 2005/0282224 | A1 | 12/2005 | Fouillet et al. |
| 2006/0254933 | A1 | 11/2006 | Adachi et al. |
| 2008/0038810 | A1 | 2/2008 | Pollack et al. |
| 2008/0166793 | A1 | 7/2008 | Beer et al. |
| 2009/0053726 | A1 | 2/2009 | Owen et al. |
| 2009/0263834 | A1* | 10/2009 | Sista et al. ............ 435/7.9 |
| 2009/0291433 | A1 | 11/2009 | Pollack et al. |
| 2010/0068764 | A1* | 3/2010 | Sista et al. ............ 435/79 |

FOREIGN PATENT DOCUMENTS

| | | | |
|---|---|---|---|
| WO | WO 2007/094739 | * | 8/2007 |

OTHER PUBLICATIONS

Jie Ding, "System level architectural optimization of semi-reconfigurable microfluidic system," M.S. Thesis, Duke University Dept of Electrical Engineering, 2000.

Moon, Hyejin, Ph.D., "Electrowetting-on-dielectric microfluidics: Modeling, physics, and MALDI application," University of California, Los Angeles, 2006.

Pollack et al., "Electrowetting-Based Actuation of Droplets for Integrated Microfluidics," Lab on a Chip (LOC), vol. 2, pp. 96-101, 2002.

Vijay Srinivasan, Vamsee K. Pamula, Richard B. Fair, "An integrated digital microfluidic lab-on-a-chip for clinical diagnostics on human physiological fluids," Lab on a Chip (LOC), vol. 4, pp. 310-315, 2004.

Tsuchiya, Hiroyoshi et al., "On-chip polymerase chain reaction microdevice employing a magnetic droplet-manipulation system", Sensors and Actuators B 130 pp. 583-588, 2007.

Chang, Yi-Hsien et al., "Integrated polymerase chain reaction chips utilizing digital microfluidics", Biomed Microdevices, vol. 8, pp. 215-225, 2006.

Fair, et al., "Integrated chemical/biochemical sample collection, pre-concentration, and analysis on a digital microfluidic lab-on-a-chip platform," Lab-on-a-Chip: Platforms, Devices, and Applications, Conf. 5591, SPIE Optics East, Philadelphia, Oct. 25-28, 2004.

Terry, S.C., J.H. Jerman, and J.B. Angell, "A Gas Chromatographic Air Analyzer Fabricated on a Silicon Wafer," IEEE Transactions on Electron Devices, vol. ED-26, 1979, pp. 1880-1886.

Tuckerman, D.B. and R.F.W. Pease, "High-Performance Heat Sinking for VLSI," IEEE Electron Device Letters, 1981, pp. 126-129.

Batchelder, J.S., "Dielectrophoretic manipulator," Review of Scientific Instruments, vol. 54, 1983, pp. 300-302.

Manz, A., N. Graber, and H.M. Widmer, "Miniaturized Total Chemical Analysis Systems: a Novel Concept for Chemical Sensing," Sensors and Actuators B: Chemical, 1990, pp. 244-248.

Welters, W.J.J. and L.G.J. Fokkink, "Fast Electrically Switchable Capillary Effects," Langmuir, vol. 14, Mar. 1998, pp. 1535-1538.

McDonald, J.C., D.C. Duffy, J.R. Anderson, D.T. Chiu, H. Wu, O.J.A. Schuueller, and G.M. Whitesides, "Fabrication of Microfluidic systems in poly (dimethylsiloxane)," Electrophoresis, vol. 21, 2000, pp. 27-40.

A. Wego, S. Richter, L. Pagel, "Fluidic microsystems based on printed circuit board technology," Journal of Micromechanics and Microengineering, vol. 11, No. 5, pp. 528-531 (Sep. 2001).

Moon H, Cho SK, Garrell RL, et al., "Low voltage electrowetting-on-dielectric," Journal of Applied Physics, vol. 92 (7): pp. 4080-4087, Oct. 1, 2002.

Locascio, L.E., et al. "Polymer microfluidic devices," Talanta, vol. 56, Feb. 2002, pp. 267-287.

Garrell, R.L. et al., "Preventing Biomolecular Adsorption in Electrowetting-Based Biofluidic Chips," Analytical Chemistry, vol. 75, Oct. 2003, pp. 5097-5102.

P.Y. Chiou, H. Moon, H. Toshiyoshi, C.-J. Kim, and M.C. Wu, "Light actuation of liquid by optoelectrowetting," Sensors and Actuators A: Physical, vol. 104, May 2003, pp. 222-228.

Squires, T.M. and S.R. Quake, "Microfluidics: Fluid physics at the nanoliter scale," Reviews of Modern Physics, vol. 77, Oct. 2005, pp. 977-1-26.

Fouillet, Y., D. Jary, A.G. Brachet, C. Chabrol, J. Boutet, P. Clementz, R. Charles, and C. Peponnet, "Design and Validation of a Complex Generic Fluidic Microprocessor Based on EWOD Droplet for Biological Applications," 9th International Conference on Miniaturized Systems for Chemistry and Life Sciences (MicroTAS), Boston, MA: 2005, pp. 58-60.

Z. Guttenberg, H. Muller, H. Habermuller, A. Geisbauer, J. Pipper, J. Felbel, M. Kielpinski, J. Scriba, and A. Wixforth, "Planar chip devices for PCR and hybridization with surface acoustic wave pump. ," Lab on a chip, vol. 5, Mar. 2005, pp. 12617-12622.

Yager, P., T. Edwards, E. Fu, K. Helton, K. Nelson, M.R. Tam, and B.H. Weigl, "Microfluidic diagnostic technologies for global public health," Nature, vol. 442, 2006, pp. 412-418.

Cooney, C.G., C-Y. Chen, M.R. Emerling, A Nadim, and J.D. Sterling, Microfluidics and Nanofluidics, vol. 2 Mar. 2006, pp. 435-446.

Chatterjee, D., B. Hetayothin, A.R. Wheeler, D.J. King, and R.L. Garrell, "Droplet-based microfluidics with nonaqueous solvents and solutions.," Lab on a Chip, vol. 6, Feb. 2006, pp. 199-206.

M.Madou, J. Zoval, G. Jia, H. Kido, J. Kim, "Lab on a CD," Annual Review of Biomedical Engineering, vol. 8, pp. 601-628, 2006.

Yi, U.-C. and C.-J. Kim, "Characterization of electrowetting actuation on addressable single-side coplanar electrodes," Journal of Micromechanics and Microengineering, vol. 16, Oct. 2006, pp. 2053-2059.

Dubois, P., G. Marchand, Y. Fouillet, J. Berthier, T. Douki, F. Hassine, S. Gmouh, and M. Vaultier, "Ionic Liquid Droplet as e-Microreactor," Analytical Chemistry, vol. 78, 2006, pp. 4909-4917.

Whitesides, G.M., "The origins and the future of microfluidics," Nature, vol. 442, 2006, pp. 368-373.

Chin, C.D., V. Linder, and S.K. Sia, "Lab-on-a-chip devices for global health: past studies and future opportunities.," Lab on a Chip, vol. 7, Jan. 2007, pp. 41-57.

Baviere, R., J. Boutet, and Y. Fouillet, "Dynamics of droplet transport induced by electrowetting actuation," Microfluidics and Nanofluidics, vol. 4, May 2007, pp. 287-294.

Paik, P.Y., V.K. Pamula, and K. Chakrabarty, "A Digital-Microfluidic Approach to Chip Cooling," IEEE Design & Test of Computers, vol. 25, Jul. 2008, pp. 372-381.

The, S. -Y., R. Lin, L.-H. Hung, and A.P. Lee, "Droplet microfluidics. ," Lab on a chip, vol. 8 Feb. 2008, pp. 198-220.

I.Barbulovic-Nad, H. Yang, P.S. Park, and A.R. Wheeler, "Digital microfluidics for cell-based assays.," Lab on a chip, vol. 8, Apr. 2008, pp. 519-526.

Huebner, A., S. Sharma, M. Srisa-Art, F. Hollfelder, J.B. Edel, and A.J. DeMello, "Microdroplets: a sea of applications?," Lab on a Chip, vol. 8, Aug. 2008, pp. 1244-1254.

Gong, J. and C.-J.C. Kim, "Direct-referencing two-dimensional-array digital microfluidics using multi-layer printed circuit board," Journal of Microelectromechanical Systems, vol. 17, Jan. 2008, pp. 257-264.

Miller, E.M. and A.R. Wheeler, "A Digital Microfluidic Approach to Homogeneous Enzyme Assays," Analytical Chemistry, vol. 80, 2008, pp. 1614-1619.

R.S. Sista, A.E. Eckhardt, V. Srinivasan, M.G. Pollack, S. Palanki, and V.K. Pamula, "Heterogeneous immunoassays using magnetic beads on a digital microfluidic platform," Lab on a Chip, vol. 8, Dec. 2008, pp. 2188-2196.

R. Sista, Z. Hua, P. Thwar, A Sudarsan, V. Srinivasan, A Eckhardt, M. Pollack, and V. Pamula, "Development of a digital microfluidic platform for point of care testing," Lab on a chip, vol. 8, Dec. 2008, pp. 2091-2104.

Luk, V.N., Pluronic additives: a solution to sticky problems in digital microfluidics.,: Langmuir: the ACS journal of surfaces ans colloids, vol. 24, Jun. 2008, pp. 6382-6389.

L. Luan, R.D. Evans, N.M. Jokerst, and R.B. Fair, "Integrated Optical Sensor in a Digital Microfluidic Platform," IEEE Sensors Journal, vol. 8, May 2008, pp. 628-635.

R. Mariella, "Sample preparation: the weak link in microfluidics-based biodetection.," Biomedical Microdevices, vol. 10, Dec. 2008, pp. 777-784.

D. Brassard, L. Malic, F. Normandin, M. Tabrizian, and T. Veres, "Water-oil core-shell droplets for electrowetting-based digital microfluidic devices.," Lab on a chip, vol. 8, Aug. 2008, pp. 1342-1349.

R. Mukhopadhyay, "Microfluidics: on the slope of enlightenment.," Analytical chemsitry vol. 81, Jun. 2009, pp. 4169-4173.

J.L. Poulos, W.C. Nelson, T.-J. Jeon, C.-J. "CJ" Kim, and J.J. Schmidt, "Electrowetting on dielectric-based microfluidics for integrated lipid bilayer formation and measurement," Applied Physics Letters, vol. 95, 2009, p. 013706.

S.M. Langelier, D.S. Chang, R.I. Zeitoun, and M. a Burns, "Acoustically driven programmable liquid motion using resonance cavities" Proceedings of the National Academy of Sciences of the USA, vol. 106, Aug. 2009, pp. 12617-12622.

L. Malic, T. Veres, and M. Tabrizian, "Biochip functionalization using electrowetting-on-dielectric digital microfluidics for surface plasmon resonance imaging detection of DNA hybridization.," Biosensors & Bioelectronics, vol. 24, Mar. 2009, pp. 2218-2224.

G.J. Shah, A.T. Ohta, E.P.-Y. Chiou, M.C. Wu, and C.-J.C.J. Kim, "EWOD-driven droplet microfluidic device integrated with optoelectronic tweezers as an automated platform for cellular isolation and analysis.," Lab on a Chip, vol. 9, Jun. 2009, pp. 1732-1739.

Office Action dated Feb. 4, 2011 from co-pending U.S. Appl. No. 12/546,115.

Response to Office Action dated Jul. 5, 2011 from co-pending U.S. Appl. No. 12/546,115.

Supplemental Response to Office Action dated Jul. 19, 2011 from co-pending U.S. Appl. No. 12/546,115.

* cited by examiner

Raw data

Normalized data

METHOD OF DETECTING AN ANALYTE

RELATED APPLICATIONS

This application is a continuation of International Patent Application No. PCT/US2009/043774, entitled "Droplet Actuator Devices, Systems, and Methods," filed on May 13, 2009, pending, which claims priority to the following U.S. Patent Applications: 61/108,880, entitled "Droplet Thermal Cycling Techniques," filed Oct. 28, 2008; 61/115,654, entitled "Droplet Thermal Cycling Techniques," filed Nov. 18, 2008; 61/153,598, entitled "Droplet Thermal Cycling Techniques," filed Feb. 18, 2009; 61/052,885, entitled "Reducing Droplet Cross-contamination in a Droplet Actuator," filed May 13, 2008; 61/098,860, entitled "Reducing Droplet Cross-contamination in a Droplet Actuator," filed Sep. 22, 2008; 61/160,607, entitled "Reducing Droplet Cross-contamination in a Droplet Actuator," filed Mar. 16, 2009; 61/103,332, entitled "Nucleic Acid Handling on a Droplet Actuator," filed Oct. 7, 2008; 61/141,820, entitled "Sample Preparation and Assay Execution on a Droplet Actuator," filed Dec. 31, 2008; the entire disclosures of each of these applications is incorporated herein by reference.

GOVERNMENT INTEREST

This invention was made with government support under AI065169-01 and AI066590-02 awarded by the National Institutes of Health. The government has certain rights in the invention.

The foregoing statement with respect to government support under AI065169-01 applies only to those aspects of the invention described and claimed in this application arising out of U.S. Patent Application Nos. 61/108,880, entitled "Droplet Thermal Cycling Techniques," filed Oct. 28, 2008; 61/115,654, entitled "Droplet Thermal Cycling Techniques," filed Nov. 18, 2008; 61/153,598, entitled "Droplet Thermal Cycling Techniques," filed Feb. 18, 2009; and with respect to government support under AI066590-02 applies only to those aspects of the invention described and claimed in this application arising out of U.S. Patent Application Nos. 61/103,332, entitled "Nucleic Acid Handling on a Droplet Actuator," filed Oct. 7, 2008; 61/141,820, entitled "Sample Preparation and Assay Execution on a Droplet Actuator," filed Dec. 31, 2008.

BACKGROUND

Droplet actuators are used to conduct a wide variety of droplet operations. A droplet actuator typically includes two substrates separated by a droplet operations gap. The substrates include electrodes for conducting droplet operations. The droplet operations gap between the substrates is typically filled with a liquid filler fluid that is immiscible with the fluid that is to be subjected to droplet operations. Droplet operations are controlled by electrodes associated with one or both of the substrates. Components of droplets may in some cases exit the droplets into the filler fluid. From the filler fluid, such components may contaminate other droplets. The invention relates to certain novel approaches to reducing or eliminating the movement of contaminants from one droplet to another on a droplet actuator via liquid filler fluid. In one application, droplet actuators are used to conduct genetic analysis using polymerase chain reaction (PCR) techniques. There is a need for improved methods of performing PCR on a droplet actuator that provide for optimum amplification and detection of a sample target.

BRIEF DESCRIPTION OF THE INVENTION

The invention provides a method of amplifying and/or detecting a target nucleic acid in a sample. The method may include providing a set of nucleic acid amplification reaction droplets. Each droplet may include a portion of the sample. The method may include treating two or more subsets of the amplification reaction droplets under conditions for amplifying the target nucleic acid to yield corresponding subsets of amplified droplets with amplified nucleic acid. Each subset of the amplification reaction droplets may include one or more of the amplification reaction droplets. Each subset of the amplification reaction droplets may be treated under different conditions for amplifying the target nucleic acid. The method may include preparing the amplified droplets for detection. The method may include detecting a signal from the amplified droplets. The method may also include determining the amount and/or the identity of the amplified nucleic present in the amplified droplets and/or the sample. Providing a set of nucleic acid amplification reaction droplets may include dispensing the set of nucleic acid amplification droplets form a sample droplet. The sample droplet may be provided in a droplet operations gap of a droplet actuator, and the dispensing may be electrode mediated. The sample droplet may be provided in a reservoir of a droplet actuator. The droplet actuator may include a liquid path from the reservoir into the droplet operations gap. Dispensing the set of nucleic acid amplification droplets may include flowing the sample droplet through the liquid path into the droplet operations gap, and using electrodes to dispense the amplification reaction droplets in the droplet operations gap. Providing a set of nucleic acid amplification reaction droplets may include providing a sample droplet; dividing the sample droplet into multiple sample sub-droplets, and combining each of the sample sub-droplets with one or more droplets may include amplification reagents to yield the amplification reaction droplets. Any one or more of the steps of the methods described herein may be effected in a droplet operations gap of a droplet actuator using droplet operations mediated by electrodes. Any one or more of the steps of the methods described herein may be effected using droplet operations mediated by electrodes. The sample droplet, the multiple sub-droplets and the one or more droplets may include amplification reagents. The amplification reaction droplets may be arranged in the droplet operations gap, and at least partially surrounded by a liquid filler fluid. Providing a set of nucleic acid amplification reaction droplets may include: providing a sample droplet; combining the sample droplet with one or more droplets may include amplification reagents to yield an amplification-ready droplet; and dividing the amplification-ready droplet to yield the amplification reaction droplets. The sample droplet, the one or more droplets may include amplification reagents, the parent amplification reaction droplet, and the amplification reaction droplets may be arranged in a droplet operations gap of a droplet actuator; and at least partially surrounded by a liquid filler fluid. The method may include treating the amplification-ready droplet under conditions selected to yield enough amplified nucleic acid in the amplification-ready droplet to ensure that each amplification reaction droplet will include target nucleic acid if the target nucleic acid may be present in the sample. Treating the amplification-ready droplet may include thermal cycling the amplification-ready droplet for 1-50 cycles, 1-40 cycles, 1-30 cycles, 1-20 cycles, or 1-10 cycles, or 1-5 cycles. Treating two or more subsets of the amplification reaction droplets under conditions for amplifying the target nucleic acid may include cycling the amplification reaction droplets between two or more thermal zones by transporting the droplets along a plurality of electrode paths in a droplet operations gap of a droplet actuator. Treating two or more subsets of the amplification reaction droplets under conditions for amplifying the target nucleic acid may include cycling subsets of two or more of the amplification reaction droplets between two or more thermal zones by transporting droplets in each subset along a common electrode path in a droplet operations gap of a droplet actuator. In some cases, the one or more electrode paths establish one or more path loops between the two or more thermal zones. Treating two or more subsets of the amplification reaction droplets under conditions for amplifying the target nucleic acid may include transporting multiple amplification reaction droplets about an electrode path loop. The method may include removing each amplified droplet from the electrode path loop when its predetermined number of cycles has been completed. Removing each amplified droplet from the electrode path loop may include using electrode mediated droplet operations to transport the amplification reaction droplet to another region of the droplet operations gap. The region of the droplet operations gap may include a temperature controlled region having a temperature selected for storing the amplified droplet pending detection. Removing each amplified droplet from the electrode path loop may include removing each amplified droplet from the droplet operations gap of the droplet actuator. In other cases, the electrode path meanders between two or more thermal zones. Transport time from one electrode on the electrode path to an adjacent electrode on the electrode path may be substantially uniform for each pair of adjacent electrodes, and residence time in a thermal zone may be established by the number of electrodes in each turn of the electrode path present in the thermal zone. Treating two or more subsets of the amplification reaction droplets under conditions for amplifying the target nucleic acid may include transporting two or more subsets of the amplification reaction droplets between thermal zones in parallel. Treating two or more subsets of the amplification reaction droplets under conditions for amplifying the target nucleic acid may include sequentially transporting two or more subsets of the amplification reaction droplets into a thermal zone. Treating two or more subsets of the amplification reaction droplets under conditions for amplifying the target nucleic acid may include transporting a first subset of the amplification reaction droplets into a first thermal zone while transporting a second subset of the amplification reaction droplets into a second thermal zone, and transporting the first subset of the amplification reaction droplets into the second thermal zone while transporting the second subset of the amplification reaction droplets into the first thermal zone. The subset of the amplification reaction droplets thermal cycled sequentially may be thermal cycled along a common electrode path. Treating two or more subsets of the amplification reaction droplets under conditions for amplifying the target nucleic acid may include amplifying two or more subsets in parallel. Treating two or more subsets of the amplification reaction droplets under conditions for amplifying the target nucleic acid may include may include thermally synchronized thermal cycling for all amplification reaction droplets. Treating two or more subsets of the amplification reaction droplets under conditions for amplifying the target nucleic acid may include thermal cycling that may be not thermally synchronized for all amplification reaction droplets. Treating two or more subsets of the amplification reaction droplets under conditions for amplifying the target nucleic acid may be effected by heating and cooling a thermal cycling region of a droplet actuator. Treating two or more subsets of the amplification reaction droplets under conditions for amplifying the target nucleic acid may include may include varying amplification reaction droplet dwell times in thermal zones at one or more thermal cycling cycle numbers. Treating two or more subsets of the amplification reaction droplets under conditions for amplifying the target nucleic acid may include may be completed for all subsets of amplification reaction droplets prior to detecting a signal from the amplified droplets. Detecting a signal from the amplified droplets may in some cases be completed for a first subset of droplets prior to treating two or more subsets of the amplification reaction droplets under conditions for amplifying the target nucleic acid for a second set of droplets. Preparing the amplified droplets for detection may include transporting a set of two or more amplified droplets away from a thermal cycling region of the droplet actuator or away from a thermal cycling zone prior to treating two or more subsets of the amplification reaction droplets under conditions for amplifying the target nucleic acid with respect to the set of two or more amplified droplets. The amplified droplet may be transported to a thermal zone having a temperature appropriate for detecting a signal from the amplified droplets. Preparing the amplified droplets for detection may include arraying at least a subset of the amplified droplets away from a thermal cycling zone prior to detecting a signal from the amplified droplets with respect to each such subset of arrayed amplified droplets. Preparing the amplified droplets for detection may include separating unbound detection reagent from the amplified nucleic acid. Preparing the amplified droplets for detection may include substantially stopping amplification in the amplified droplet. Preparing the amplified droplets for detection may include transferring the amplified droplets from one droplet actuator to another droplet actuator. Substantially stopping amplification in the amplified droplet may include adjusting droplet temperature to substantially stop the amplification reaction. Substantially stopping amplification in the amplified droplet may include adding a reagent to the amplified droplet to substantially stop the amplification reaction. Adding a reagent to the amplified droplet may include combining the amplified droplet with a reagent droplet, the reagent droplet may include reagent selected to substantially stop the amplification reaction. The reagent selected to substantially stop the amplification reaction may include a reagent that substantially stops the amplification reaction by interfering with polymerase activity, interfering with polymerase cofactor activity, binding to nucleic acids, and/or releasing iron ions. In certain embodiments, the amplification reaction droplets lack a detection reagent. Preparing the amplified droplets for detection may include adding a detection reagent to the amplified droplets. Adding a detection reagent to the amplified droplets may include combining each amplified droplet with a droplet including a detection reagent. Preparing the amplified droplets for detection may include combining each of the amplified droplets with a droplet including one or more detection reagents. Detecting a signal from the amplified droplets may include detecting amplification based on a signal mediated by the detection reagent. Detecting a signal from the amplified droplets may include detecting a signal from each amplified droplet following transport of such droplet into a detection window. Detecting a signal from the amplified droplets may include transporting sets of one or more of the subsets of amplified droplets into a detection window for detection. In certain embodiments, treating two or more subsets of the amplification reaction droplets under conditions for amplifying the target nucleic acid may be accomplished in a droplet operations gap of a droplet actuator; and preparing the amplified droplets for detection and/or detecting a signal from the amplified droplets may be accomplished outside the droplet operations gap. Thus, preparing the amplified droplets for detection may include transporting one or more of the amplified droplets out of the droplet operations gap for detection. Detecting a signal from the amplified droplets may in some cases may be effected in a reservoir exterior to the droplet operations gap of the droplet actuator. Preparing the amplified droplets for detection may include transporting subsets of amplified droplets into a detection window beginning with lower cycle number subsets and proceeding to higher cycle number subsets. Detecting a signal from the amplified droplets may include scanning an array of amplified droplets. Detecting a signal from the amplified droplets may include imaging an array of amplified droplets. In certain embodiments, treating two or more subsets of the amplification reaction droplets under conditions for amplifying the target nucleic acid begins in parallel for multiple subsets; preparing the amplified droplets for detection begins in series, each subset beginning after the start of a previous subset; detecting a signal from the amplified droplets begins in series, each subset beginning after the start of a previous subset. In some cases, preparing the amplified droplets for detection begins in series, each subset beginning after the completion of a previous subset. In some cases, detecting a signal from the amplified droplets begins in series, each subset beginning after the completion of a previous subset. In some cases, detecting a signal from the amplified droplets is accomplished using an imaging device which tracks droplets and measures signal from the droplets as they move through the field of the device. In some cases, preparing the amplified droplets for detection begins in parallel, each subset beginning the process at about the same time. In some cases, detecting a signal from the amplified droplets begins in parallel, each subset beginning the process at about the same time. The method may include determining the amount of the amplified nucleic present in the amplified droplets by determining an increase or decrease in signal at a thermal cycling end-point for each of the subsets of amplified droplets. Determining the amount of the amplified nucleic acid present in the amplified droplets and/or the sample may include using the amount of amplified nucleic acid present in the amplified droplets to determine the amount of the target nucleic acid present in the sample droplet. Determining the amount of the amplified nucleic acid present in the amplified droplets and/or the sample may include using the amount of amplified nucleic acid present in the amplified droplets after different numbers of thermal cycles to determine the amount of the target nucleic acid present in the sample droplet. The different conditions for amplifying the target nucleic acid may include different numbers of thermal cycles for each subset of the amplification reaction droplets. The amplification reaction droplets may include a detection reagent. In other cases, the amplification reaction droplets may not include a significant amount of a detection reagent. The one or more droplets including amplification reagents further may include a detection reagent. In other cases, the one or more droplets including amplification reagents may not include a significant amount of a detection reagent. The detection reagent may include a nucleic acid binding agent. The nucleic acid binding agent may, in some cases, significantly inhibit the rate of nucleic acid amplification. The nucleic acid binding agent may include an intercalating agent. The intercalating agent may include a fluorescent dye. The target nucleic acid may be indicative of a genetic disorder or infectious disease. The target nucleic acid may be indicative of identification of an individual or subgroup of individuals from a biological population. In some embodiments, one or more of the nucleic acid amplification reaction droplets may be subjected to an initial detection step prior to treating two or more subsets of the amplification reaction droplets under conditions for amplifying the target nucleic acid, and determining the amount of the amplified nucleic acid present in the amplified droplets and/or the sample may include a comparison between signal detected in the initial detection step and signal detected from the amplified droplets. The method of detecting a target nucleic acid in a sample may include stopping the method when sufficient data has been collected to quantify the target nucleic acid present in the starting sample within a predetermined range of statistical certainty. The method may include selecting a first set of cycle numbers expected to provide sufficient data for determining the amount of the amplified nucleic present in the amplified droplets and/or the sample, for each of the selected cycle numbers; subjecting a subset of one or more amplification reaction droplet to the amplifying, preparing, detecting, and determining steps; and determining whether sufficient data has been collected to identify or quantify the target nucleic acid present in the sample within a predetermined range of statistical certainty. Steps may be repeated with new sets of cycle numbers until sufficient data has been collected to identify or quantify the target nucleic acid present in the starting sample within a predetermined range of statistical certainty, or sufficient data has been collected to determine within a predetermined range of statistical certainty that the target nucleic acid may be not present in the sample. Determining whether sufficient data has been collected may include determining whether sufficient data has been collected to identify the target nucleic acid present in the sample within a predetermined range of statistical certainty. Determining whether sufficient data has been collected may include determining whether sufficient data has been collected to quantify the target nucleic acid present in the sample within a predetermined range of statistical certainty.

The invention provides a method of monitoring the increase in target nucleic acid in a sample. The method may include providing a set of nucleic acid amplification reaction droplets, each droplet including a portion of the sample. The method may include thermal cycling two or more subsets of the amplification reaction droplets under conditions for amplifying the target nucleic acid to yield amplified droplets with amplified double-stranded nucleic acid. Each subset of the amplification reaction droplets may include one or more of the amplification reaction droplets. Each subset of the amplification reaction droplets may be thermal cycled for a different number of cycles. Each subset of the amplification reaction droplets may be not subjected to detection prior to the completion of a predetermined number of cycles for such subset. The method may include executing a detection preparation protocol, which may include combining each of the amplified droplets with a detection reagent for detection of amplified nucleic acid to yield detection-ready droplets. The method may include detecting a signal from the detection-ready droplets. The method may include determining, based on the signal, the presence and/or amount of the amplified nucleic present in the amplified droplets and/or the sample.

The invention provides a pre-loaded droplet actuator cartridge. The pre-loaded droplet actuator cartridge may include one or more substrates forming a droplet operations gap, and electrodes associated with the one or more substrates and arranged for mediating droplet operations in the droplet operations gap. The pre-loaded droplet actuator cartridge may include a first reservoir including one or more droplets including amplification reagents and lacking detection reagents, and a second reservoir including one or more detection reagents. The pre-loaded droplet actuator cartridge may include one or more fluid paths fluidly connecting the first reservoir and the second reservoir with the droplet operations gap. For example, the pre-loaded droplet actuator cartridge may include a fluid path fluidly connecting the first reservoir with the droplet operations gap. Similarly, the pre-loaded droplet actuator cartridge may include a fluid path fluidly connecting the second reservoir with the droplet operations gap. The pre-loaded droplet actuator cartridge may include a means for loading a sample into the droplet operations gap. The means for loading a sample into the droplet operations gap may, for example, include a sample loading reservoir and a fluid path fluidly connecting the sample loading reservoir with the droplet operations gap. The invention provides a kit including the pre-loaded droplet actuator cartridge. The kit may also include software for executing for executing an amplification protocol using the cartridge. Any of the physical embodiments of the invention may be included in such a kit including the physical embodiment and software for controlling the physical embodiment.

The invention provides a method of detecting an analyte. The method may include providing in a detection window a droplet. The droplet may include a signal-producing substance indicative of the presence and/or quantity of an analyte. The droplet may include one or more magnetically responsive beads which may interfere with signal produced by the signal producing substance. The method may include using a magnetic field for magnetically removing the magnetically responsive beads from the detection window, and/or magnetically restraining the magnetically responsive beads from entering the detection window while transporting and/or retaining the droplet in the detection window. The method may include detecting a signal produced by the signal-producing substance without substantial interference from the magnetically responsive beads. Similarly, the invention provides a method of detecting an analyte including providing in a detection window a droplet, where the droplet includes a signal-producing substance indicative of the presence and/or quantity of an analyte and one or more beads which are not substantially magnetically responsive, and which may interfere with signal produced by the signal producing substance. The method may include using physical barrier for restraining the beads from entering the detection window while transporting and/or retaining the droplet in the detection window. The method may include detecting a signal produced by the signal-producing substance without substantial interference from the beads. It will be appreciated that this physical barrier approach may be used regardless of whether or not the beads are magnetically responsive. In these methods of detecting an analyte, the droplet may be provided in a droplet operations gap of a droplet actuator. The detection window may include an opening or window in a substrate of the droplet actuator. With respect to the embodiment making use of substantially magnetically non-responsive beads, using a magnetic field may include providing a fixed magnet in proximity to the detection window. Transporting the droplet into the detection window may deliver the magnetically responsive beads into sufficient proximity with the fixed magnet that the beads may be pulled away from and/or restrained from entering the detection window. With respect to the embodiment making use of physical barrier, transporting the droplet into the detection window may be accomplished while the beads are restrained from progressing into the detection window by a physical barrier. This restraining of beads from entering the detection window may be accomplished with or without removing the magnetically responsive beads from the droplet. In these and any other embodiments of the invention making use of a magnetic field, the magnetic field may be generated by any suitable magnetic field source. For example, the magnetic field source may include a fixed permanent magnet, a moveable permanent magnet, and/or an electromagnet. The magnetic field may be arranged to aggregate the magnetically responsive beads at an edge of the droplet. The magnetic field may be arranged to aggregate the magnetically responsive beads in a region of the droplet which may be outside the detection window. In some cases, the magnetic field is selected to break the magnetically responsive beads away from the droplet. For example, the magnetic field may break the magnetically responsive beads away from the droplet while the droplet may be being held in place and/or moved by electrode mediated forces. In some cases, the magnetic field attracts the magnetically responsive beads in a manner which pulls them to an edge of the droplet while the droplet may be at least partially in the detection window. In some cases, the magnetic field pulls the magnetically responsive beads out of the droplet as the droplet passes over the magnet. In some cases, the magnetic field pulls the magnetically responsive beads out of the droplet as the droplet approaches a vicinity of the magnet. In some cases, the magnetic field pulls the magnetically responsive beads out of the droplet as the droplet approaches the detection window. In some cases, the magnetic field attracts the magnetically responsive beads in a manner which restricts substantially all of the beads from entering or re-entering the detection window as the droplet may be transported into the detection window. The detection window may be provided in a substrate of a droplet actuator device. The droplet actuator may, for example, include a plurality of paths of electrodes associated with the droplet operations substrate, each path associated with a detection window, and a magnetic field in proximity to the path arranged for magnetically removing the magnetically responsive beads from the corresponding detection window, and/or magnetically restraining the magnetically responsive beads from entering the corresponding detection window while transporting into and/or retaining the droplet in the detection window. The droplet may emit a signal indicative of the presence, absence and/or quantity of one or more analytes. For example, the one or more analytes may include amplified nucleic acid. The detection window may be located in a substrate of a droplet actuator, and the droplet actuator may include temperature control zones along the path of electrodes for conducting a thermal cycling reaction. The method using such droplet actuator may include thermal cycling an amplification-ready droplet to yield an amplified droplet, and transporting the amplified droplet into the detection window. The method may include transporting a droplet may include magnetically responsive beads along the path of electrodes to the path of electrodes at least partially into the detection window following 1 or more of the thermal cycles.

The invention also provides a method of thermal cycling a droplet. The method may include providing a droplet at least partially surrounded by a filler fluid. The droplet may potentially include a target nucleic acid. The droplet may include reagents sufficient to cause amplification in the presence of the target nucleic acid, the reagents may include a fluorophore that does not significantly partition into the filler fluid during the execution of a thermal cycling protocol. The method may include adjusting the temperature of the droplet according to a thermal cycling protocol to induce amplification in the presence of the target nucleic acid. The fluorophore may include a polar fluorophore. The fluorophore may be substantially impermeable to cell membranes. The fluorophore may be completely impermeable to cell membranes. The fluorophore may include the EVAGREEN® fluorophore. The fluorophore may include the TO-PRO1 fluorophore. The filler fluid may consist essentially of silicone oil, optionally doped with one or more additives. The filler fluid may consist essentially of a 10 to 20-carbon oil, optionally doped with one or more additives. The filler fluid may consist essentially of a 15 to 20-carbon oil, optionally doped with one or more additives. The filler fluid may consist essentially of hexadecane oil, optionally doped with one or more additives. The filler fluid may consist essentially of substantially degassed oil, optionally doped with one or more additives. Providing a droplet may include providing a droplet in a droplet operations gap of a droplet actuator. Adjusting the temperature of the droplet according to a thermal cycling protocol may include heating and/or cooling the droplet in the droplet operations gap of a droplet actuator. Adjusting the temperature of the droplet according to a thermal cycling protocol may include transporting the droplet between thermal zones in the droplet operations gap using electrode mediated droplet operations.

The invention may include a method of executing a protocol on a droplet actuator. The method may include treating one or more regions of the droplet actuator by conducting droplet operations on one or more electrodes within the regions with a droplet may include a passivation agent, and conducting the protocol using one or more of the treated regions of the droplet actuator. The protocol may include steps in the analysis of a target nucleic acid, and the passivation agent may include a nucleic acid that may be not the target nucleic acid. The protocol may include a nucleic acid amplification protocol. The protocol may include a thermal cycling protocol. To name a few examples, the passivation agent may include a nucleic acid, polyvinylpyrrolidone, polyethylene glycol, a surfactant, a tween, an albumin, a serum albumin, bovine serum albumin, and/or a dye. The passivation agent may be selected to adsorb onto a surface of the droplet actuator. The passivation agent may be selected to absorb into filler fluid. The one or more droplets may deliver sufficient passivation agent to substantially saturate potential passivation sites. The protocol may be conducted using a droplet including the passivation reagent. As an example, the protocol may include a nucleic acid amplification protocol. The nucleic acid amplification protocol and treating steps may be conducted simultaneously using a droplet including nucleic acid amplification reagents and the passivation agent.

The invention also provides a droplet actuator for conducting droplet operations in elevated temperatures. The droplet actuator may include a droplet operations substrate and a cover adjacent to the droplet operations surface and separated from the droplet operations surface to form a droplet operations gap between the droplet operations surface and the cover, the droplet operations gap has a height of at least 250 µm. The droplet actuator may include a path of electrodes associated with the droplet operations substrate and/or cover and arranged for transporting a droplet between thermal zones according to a thermal cycling protocol. The droplet actuator may include temperature control elements arranged to establish one or more thermal zones in the droplet operations gap. In some cases, the droplet operations gap may have a height selected to render a unit sized droplet substantially spherical in shape. For example, in certain embodiments, may have a height ranging from about 250 µm to about 500 µm, or from about 275 µm to about 450 µm, or from about 300 µm to about 400 µm, or from about 320 µm to about 375 µm, or from about 320 µm to about 350 µm. In certain embodiments, the electrodes may have a pitch, and the droplet operations gap may have a height establishing a pitch:height ratio ranging from about 7:1 to about 2.8:1, or from about 6:1 to about 3:1, or from about 4.3:1 to about 3.4:1. In certain embodiments, the droplet operations gap has a height selected to keep volume loss from a droplet undergoing a thermal cycling protocol to less than 5% for a complete thermal cycling protocol, or less than 1% for a complete thermal cycling protocol, or less than 0.01% for a complete thermal cycling protocol. In certain embodiments, the droplet operations gap has a height selected to keep volume loss from a droplet undergoing a thermal cycling protocol to less than 0.1% per thermal cycle, or less than 0.01% per thermal cycle, or less than 0.001% per thermal cycle. In some cases, the droplet operations gap has a height selected to substantially eliminate volume loss during a thermal cycling protocol. The invention also provides a method of conducting a thermal cycling reaction, the method may include providing a droplet actuator of this aspect of the invention; transporting a droplet may include magnetically responsive beads along the path of electrodes to the path of electrodes at least partially into the detection window such that the magnet attracts the magnetically responsive beads in a manner which restricts one or more of the beads from entering the detection window; and using the sensor to detect a signal from the droplet.

The invention provides a method of preparing a sample for analysis. The method may include providing a droplet actuator including a droplet operations substrate, electrodes arranged for conducting droplet operations on a droplet operations surface of the substrate, a cover adjacent to the droplet operations surface and separated from the droplet operations surface to form a droplet operations gap between the droplet operations surface and the cover, a reservoir associated with the top substrate and may include beads having an affinity for one or more target analytes and/or substances may include one or more target analytes, a liquid path extending from the reservoir into the droplet operations gap, and a magnetic field source associated with the droplet operations substrate and configured to produce a magnetic field sufficient to attract magnetically responsive beads. The method may include supplying a sample into the reservoir. The sample may include one or more of the target substances. The method may include flowing sample with the magnetically responsive beads through the liquid path into the droplet operations gap. The method may include aggregating the magnetically responsive beads at the magnet. The method may include removing the magnetic field or removing the beads from the magnetic field to yield a sample droplet in the droplet operations gap with magnetically responsive beads. In some cases, the liquid path may be a substantially direct liquid path, such as a hole or opening in a substrate (as opposed to a more tortuous liquid path). The magnet may have a magnetic field strength sufficient to attract one or more beads from the reservoir into the droplet operations gap. The droplet actuator may include a reservoir electrode associated with the droplet operations substrate and arranged to receive fluid entering the droplet operations gap via the liquid path. The magnet may be positioned on an opposite side of the reservoir electrode relative to the liquid path. The magnet may be any element or combination of elements for generating a suitable magnetic field, such as an electromagnet or a permanent magnet. The magnet may be spatially adjustable. The magnet may be associated with a moveable magnetic shield capable of blocking or interfering with the magnetic field of the permanent magnet in the droplet operations gap in a first position, and not blocking or interfering with the magnetic field of the permanent magnet in the droplet operations gap in a second position. The droplet actuator may include an agitator arranged to agitate a sample fluid in the reservoir, and the method may include agitating the sample in the reservoir. The droplet actuator may include a sonicator arranged to apply sound energy to a sample fluid in the reservoir, and the method may include sonicating the sample in the reservoir.

The droplet actuator may also include a second magnet associated with one or more of the electrodes. The substances may include one or more target analytes for which the beads have affinity. In one embodiment, the target analyte includes cells, and the method includes lysing or otherwise breaking up the cells. For example, lysing the cells may be achieved by adding a lysis reagent to the droplet including the cells. As an example, adding a lysis reagent may include combining the sample droplet in the droplet operations gap including magnetically responsive beads with a lysis droplet including a cell lysis reagent. The combined droplet may be sonicated or otherwise agitated or shaken to cause mixing. The method may sometimes include reapplying the magnetic field to immobilize the magnetically responsive beads. The method may include transporting the droplet away from the immobilized magnetically responsive beads. The method may include transporting a portion of the droplet away from the magnetically responsive beads. The method may include combining the droplet or portion of the droplet transported away with a droplet including beads having affinity for the one or more target analytes. The method may include conducting a washing protocol to wash beads having affinity for the one or more target analytes yielding a droplet having beads with substantially purified target analyte. The method may include conducting an analytical protocol using the droplet having beads with the substantially purified target analyte. The analytical protocol step may be accomplished in the droplet operations gap or outside the droplet operations gap. The analytical protocol step may be accomplished on the droplet actuator, on another droplet actuator or without the use of the droplet actuator. For example, the droplet with beads and the substantially purified target analyte may be removed from the droplet operations gap prior to conducting the analytical protocol. The method may include removing the having beads with substantially purified target analyte from the droplet operations gap. The method may include eluting the one or more target analytes from the beads. The eluting may include combining the droplet including beads with substantially purified target analyte with a droplet including an elution buffer, yielding a droplet with the beads and the eluted one or more target analytes. The method may include removing the beads from the droplet with the beads and the eluted one or more target analytes to yield a droplet with substantially purified target analyte and substantially lacking beads. The removing may, for example, be effected using a magnetic field and/or a physical barrier. The method may include removing the droplet with substantially purified target analyte and substantially lacking beads from the droplet operations gap. The method may include conducting an analytical protocol using the droplet with substantially purified target analyte and substantially lacking beads. The protocol may be effected on or off the droplet actuator, in or out of the droplet operations gap. Any of the assay protocols described here may include providing an output indicative of results of the analytical protocol. One or more of the method steps may be executed by a system including the droplet actuator and a processor programmed to execute the one or more of the method steps. The method may include outputting a user readable output indicative of results of the analytical protocol. The target analyte may include a nucleic acid, protein or peptide, antibody, small organic molecule, etc. The droplet operations gap may be filled with a liquid filler fluid.

The invention provides a method of operating a droplet actuator. The method may include providing a droplet actuator device with one or more substrates configured to form an interior droplet operations gap. The method may include providing a liquid filler fluid in the droplet operations gap. The method may include executing a droplet protocol in the filler fluid in the droplet operations gap. The method may include replacing the filler fluid in the droplet operations gap. Once the filler fluid is replaced, the method may include executing another droplet protocol in the filler fluid in the droplet operations gap. The invention provides for multiple droplet protocols to be executed on a common droplet actuator with replacement of the filler fluid in between instances of droplet protocol execution. Thus, for example, the invention may include a fill-execute-refill pattern of usage, where execute-refill is repeated numerous times, e.g., 2, 5, 10, 20, 50, 100 or more times. Similarly, the invention may include a fill-execute-execute-refill pattern of usage, where execute-execute-refill is repeated numerous times, e.g., 2, 5, 10, 20, 50, 100 or more times. Replacing the filler fluid in the droplet operations gap may include flushing filler fluid through the droplet operations gap. The flushing of filler fluid through the droplet operations gap may continue until a predetermined amount of flushing is achieved. The flushing of filler fluid through the droplet operations gap may continue until an indicator of cleaning (e.g., a contaminant measured in the removed filler fluid) reaches a predetermined level. The amount of flushing may be automated. The droplet protocol may, for example, include a protocol for measuring the presence and/or quantity of a target analyte. For example, the protocol may be a diagnostic protocol. To name a few specific examples, the droplet protocol may be a nucleic acid amplification protocol, nucleic acid sequencing protocol, immunoassay protocol, and/or an enzymatic assay protocol. In some embodiments, liquid filler fluid may be tested for contamination during replacement of filler fluid, and the execution of another protocol may be conducted after a predetermined level of contamination reduction has been achieved. This process may be automated. Replacing the filler fluid in the droplet operations gap may include flowing the liquid filler fluid from a liquid filler fluid source, through the droplet operations gap, and out of the droplet operations gap. Replacing the filler fluid in the droplet operations gap may include flowing a cleaning fluid through the droplet operations gap prior to replacing the filler fluid in the droplet operations gap. Replacing the filler fluid in the droplet operations gap may include flowing filler fluid through the droplet operations gap prior to replacing the filler fluid in the droplet operations gap. Replacing the filler fluid in the droplet operations gap may include flowing heated cleaning liquid through the droplet operations gap prior to replacing the filler fluid in the droplet operations gap. The heated cleaning liquid may have a temperature which is selected to degrade a contaminant. For example, in various embodiments, the temperature ranges from about 30° C. to about 125° C., or from about 60° C. to about 115° C., or from about 75° C. to about 105° C., or greater than about 90° C., or greater than about 100° C., or greater than about 125° C., or greater than about 150° C. The temperature will typically be less than a temperature at which one or more components of the droplet actuator would sustain undue damage, i.e., damage that would render the droplet actuator unfit for its intended use. A cooling liquid, such as a filler fluid, may be flowed through the droplet actuator gap to establish an appropriate or operational temperature following heated cleaning. The heated cleaning liquid may, for example, include filler fluid, an oil, a solvent, and/or an aqueous cleaning liquid. The cleaning liquid may include a component in which lipophilic substances may be soluble and a component in which hydrophilic substances may be soluble. Replacing the filler fluid in the droplet operations gap may include flowing a gas through the droplet actuator gap to dry the droplet actuator gap prior to replacing the filler fluid in the droplet operations gap. The gas may include air or another gas. The gas may be heated or cooled, relative to the temperature of the cleaning liquid. The gas may, for example, have a temperature greater than about 50° C., greater than about 75° C., greater than about 100° C., greater than about 125° C. or greater than about 150° C. The temperature will typically be less than a temperature at which one or more components of the droplet actuator would sustain undue damage, i.e., damage that would render the droplet actuator unfit for its intended use. Replacing the filler fluid in the droplet operations gap may include flowing a cleaning liquid through the droplet actuator gap prior to flowing the gas through the droplet actuator gap. Replacing the filler fluid in the droplet operations gap may include replacing at least about 50% of the filler fluid present in the droplet operations gap, or at least about 75% of the filler fluid present in the droplet operations gap, or at least about 90% of the filler fluid present in the droplet operations gap, or at least about 95% of the filler fluid present in the droplet operations gap, or at least about 99% of the filler fluid present in the droplet operations gap during, or at least about 99.9% of the filler fluid present in the droplet operations gap, or substantially all of the filler fluid present in the droplet operations gap. One or more surfaces of the droplet operations gap may include a coating, and the cleaning liquid may be selected to remove a layer of the coating. Replacing the filler fluid in the droplet operations gap may include flowing a cooling liquid through the droplet operations gap to establish a predetermined temperature prior to replacing the filler fluid in the droplet operations gap. The cleaning fluid may include a solvent. The cleaning fluid may include an aqueous solution. The cleaning fluid may include one or more components that dissolve lipophilic compounds and one or more components that dissolve hydrophilic compounds. The invention provides a computer readable medium with a program having instructions for conducting the method filler fluid replacement methods of the invention. The invention provides a system with a droplet actuator device including one or more substrates configured to form an interior droplet operations gap, an opening into the droplet operations gap fluidly coupled to a liquid filler fluid source, one or more valves and/or pumps configured to control flow of filler fluid from the filler fluid source through the opening and into the droplet operations gap, and a processor controlling one or more of the pumps and/or valves and programmed to execute any of the filler fluid replacement and/or cleaning methods of the invention.

The invention provides a droplet actuator with one or more substrates forming a droplet operations gap. The droplet operations gap may include a thermal cycling path and one or more barriers establishing at least two temperature control reservoirs fluidly joined by a liquid path, and electrodes associated with one or both substrates and configured for transporting a droplet between the temperature control reservoirs. The droplet actuator may include two or more of such thermal cycling paths.

The invention provides a method of inhibiting cross-contamination between droplets on a droplet actuator. The method may include providing a droplet actuator with one or more substrates forming a droplet operations gap, electrodes associated with the one or more substrates establishing a plurality of substantially parallel droplet transport paths, and a liquid filler fluid substantially filling the droplet operations gap. The method may include transporting multiple assay droplets on a first subset of the plurality of substantially parallel droplet transport paths. The method may include transporting one or more buffer droplets on a second subset of the plurality of substantially parallel droplet transport paths, each droplet transport path of the second subset may be between two droplet transport paths of the first subset. The transporting of assay droplets and wash droplets may be synchronized. Two or more wash droplets may be provided/transported on each droplet transport path of the second subset. The wash droplet may be provided in the form of a droplet or a droplet slug (elongated droplet). The method may include transporting one or more buffer droplets on the droplet transport paths of the first subset. The method may include transporting one or more buffer droplets on the droplet transport paths of the first subset. The method may include transporting one or more buffer droplets on the droplet transport paths of the first subset on an opposite side of the assay droplet relative to the first wash droplet. The assay droplet may include a nucleic amplification droplet. The method may include transporting the assay droplet between two thermal zones to effect amplification.

The invention also provides a droplet actuator with one or more substrates arranged to provide a droplet operations gap, electrodes associated with the one or more of substrates establishing a plurality of substantially parallel droplet transport paths, a liquid filler fluid substantially filling the droplet operations gap, and barriers between each of the droplet transport paths and preventing filler fluid associated with one droplet operations path from contacting filler fluid associated with other droplet operations paths. The droplet actuator may include an assay droplet on two or more of the droplet transport paths. The assay droplet may include reagents and sample for amplifying nucleic acid.

The invention provides method of reducing cross contamination between droplets on a droplet actuator. The method may include providing a droplet actuator may include an interior droplet operations gap and an oil-based filler fluid in the droplet operations gap, and providing an aqueous droplet in the droplet operations gap. The droplet may be at least partly surrounded by the oil-based filler fluid. The droplet may include a surfactant-enzyme complex, the complex may include a surfactant coupled to an enzyme selected to degrade a potentially contaminating substance. To provide a few non-limiting examples of suitable enzymes: nucleases, endonucleases, exonucleases, and/or proteinases. With respect to the surfactant, any suitable surfactant may be used. Examples include polyalkalene (PAG)-alkyl surfactant, such as polyethylene (PEG)-alkyl surfactants. The surfactant-enzyme complex may include an enzyme-PAG-alkyl complex. The surfactant may, for example, be coupled at an amino moiety of the enzyme. The surfactant-enzyme complex may be present in the droplet in an amount which may be sufficiently low to render it substantially inactive in the droplet and sufficiently high to be active in a minidroplet, microdroplet, or nanodroplet, that may be formed from the droplet. In some cases, the quantity is selected for activity in minidroplets having an average volume which may be less than about 10 µL, or less than about 1 µL, or less than about 0.01 µL, or less than about 0.001 µL. In some cases, the ratio of average droplet size to average minidroplet size may be about 1000 to less than about 1, or about 1000 to less than about 0.1, or about 1000 to less than about 0.01, or about 1000 to less than about 0.001. The potentially contaminating substance may, for example, include a protein, a nucleic acid, or a reagent. In certain embodiments, substantially all of the surfactant-enzyme complex may be trapped at a surface of the droplet. The filler fluid may include an oil, such as a silicon oil. The droplet may be partially surrounded by the filler fluid. The droplet may be substantially surrounded by the filler fluid. The droplet may be completely surrounded by the filler fluid.

The invention provides a digital amplification method. The method may include providing a sample droplet with a target nucleic acid, and optionally including amplification reagents. The method may include dispensing sub-droplets from the sample droplet, and if amplification reagents may be not present in the sample droplet, combining each sub-droplet with amplification reagents to yield an amplification-ready droplet. The method may include subjecting each sub-droplet to a thermal cycling protocol selected to amplify the target nucleic acid. The method may include detecting amplified product in each sub-droplet. The method may include determining the number of sub-droplets that contain a sample portion from which said amplified product may be formed. Typically, at least one of said sub-droplets includes at least one target nucleic acid molecule. The amplification reagents may include at least one probe that hybridizes to amplified target molecules and has a fluorescence property that changes upon hybridization or as a consequence of hybridization. The method may include determining the number of sub-droplets that contain a sample portion from which said amplified product is formed. The determining may, in some cases, include detecting the fluorescence change consequence to hybridization of said at least one probe. Determining the number of sub-droplets that contain a sample portion from which said amplified product may be formed may include imaging all sub-droplets together. Determining the number of sub-droplets that contain a sample portion from which said amplified product may be formed may include transporting droplets one at a time or in sub-groups through a detection window. The sub-droplets may have volumes less than about 1 µL, or ranging from greater than about 1 µL to about 1000 µL, or ranging from greater than about 100 µL to about 500 µL. One or more of the stems of this and other methods of the invention may be performed in a droplet operations gap of a droplet actuator. The sub-droplets may be compressed into a flattened or disk-shaped conformation between two substrates in the droplet operations gap. The droplet operations gap may have a height ranging from about 50 µm to about 1000 µm, or from greater than about 100 µm to about 500 µm. Thermal cycling may be effected by transporting droplets from one thermal zone to another. In certain embodiments, the droplet actuator lacks sample chambers. In certain embodiments, the droplet actuator lacks a flow-through channel. In certain embodiments, the dispensing of sub-droplets from the sample droplet may be effected without a displacing fluid displacing sample from a flow-through channel. In certain embodiments, the sample droplet including a target nucleic acid may also may include amplification reagents. In certain embodiments, amplification reagents may be not present in the sample droplet, and the method may include combining each sub-droplet with amplification reagents to yield an amplification-ready droplet. In certain embodiments, detecting amplified product in each sub-droplet may include combining the amplified droplet with a droplet including one more detection reagents prior to subjecting the droplet to detection.

These aspects of the invention and many others will be apparent from the remaining sections of the instant specification and the appended claims.

DEFINITIONS

As used herein, the following terms have the meanings indicated.

"Activate" with reference to one or more electrodes means effecting a change in the electrical state of the one or more electrodes which, in the presence of a droplet, results in a droplet operation.

"Bead," with respect to beads on a droplet actuator, means any bead or particle capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator or otherwise configured with respect to a droplet actuator in a manner which permits a droplet on the droplet actuator to be brought into contact with the bead, on the droplet actuator and/or off the droplet actuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay reagent. Examples of suitable magnetically responsive beads are described in U.S. Patent Publication No. 2005-0260686, entitled, "Multiplex flow assays preferably with magnetic particles as solid phase," published on Nov. 24, 2005, the entire disclosure of which is incorporated herein by reference for its teaching concerning magnetically responsive materials and beads. The fluids may include one or more magnetically responsive and/or non-magnetically responsive beads. Examples of droplet actuator techniques for immobilizing magnetically responsive beads and/or non-magnetically responsive beads and/or conducting droplet operations protocols using beads are described in U.S. patent application Ser. No. 11/639,566, entitled "Droplet-Based Particle Sorting," filed on Dec. 15, 2006; U.S. Patent Application No. 61/039,183, entitled "Multiplexing Bead Detection in a Single Droplet," filed on Mar. 25, 2008; U.S. Patent Application No. 61/047,789, entitled "Droplet Actuator Devices and Droplet Operations Using Beads," filed on Apr. 25, 2008; U.S. Patent Application No. 61/086,183, entitled "Droplet Actuator Devices and Methods for Manipulating Beads," filed on Aug. 5, 2008; International Patent Application No. PCT/US2008/053545, entitled "Droplet Actuator Devices and Methods Employing Magnetic Beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator. For examples of droplet fluids that may be subjected to droplet operations using the approach of the invention, see International Patent Application No. PCT/US2006/47486, entitled, "Droplet-Based Biochemistry," filed on Dec. 11, 2006. In various embodiments, a droplet may include a biological sample, such as whole blood, lymphatic liquid, serum, plasma, sweat, tear, saliva, sputum, cerebrospinal liquid, amniotic liquid, seminal liquid, vaginal excretion, serous liquid, synovial liquid, pericardial liquid, peritoneal liquid, pleural liquid, transudates, exudates, cystic liquid, bile, urine, gastric liquid, intestinal liquid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids.

"Droplet Actuator" means a device for manipulating droplets. For examples of droplet actuators, see U.S. Pat. No. 6,911,132, entitled "Apparatus for Manipulating droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. Nos. 6,773,566, entitled "Electrostatic Actuators for Microfluidics and Methods for Using Same," issued on Aug. 10, 2004 and 6,565,727, entitled "Actuators for Microfluidics Without Moving Parts," issued on Jan. 24, 2000, both to Shenderov et al.; Pollack et al., International Patent Application No. PCT/US2006/047486, entitled "Droplet-Based Biochemistry," filed on Dec. 11, 2006; and Roux et al., U.S. Patent Pub. No. 20050179746, entitled "Device for Controlling the Displacement of a Drop Between two or Several Solid Substrates," published on Aug. 18, 2005; the disclosures of which are incorporated herein by reference. Certain droplet actuators will include a substrate, droplet operations electrodes associated with the substrate, one or more dielectric and/or hydrophobic layers atop the substrate and/or electrodes forming a droplet operations surface, and optionally, a top substrate separated from the droplet operations surface by a droplet operations gap. One or more reference electrodes may be provided on the top and/or bottom substrates and/or in the droplet operations gap. In various embodiments, the manipulation of droplets by a droplet actuator may be electrode mediated, e.g., electrowetting mediated or dielectrophoresis mediated or Coulombic force mediated. Examples of other methods of controlling liquid flow that may be used in the droplet actuators of the invention include devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and optoelectrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed in droplet actuators of the invention.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles.

"Filler fluid" means a liquid associated with a droplet operations substrate of a droplet actuator, which liquid is sufficiently immiscible with a droplet phase to render the droplet phase subject to electrode-mediated droplet operations. The filler fluid may, for example, be a low-viscosity oil, such as silicone oil. Other examples of filler fluids are provided in International Patent Application No. PCT/US2006/047486, entitled, "Droplet-Based Biochemistry," filed on Dec. 11, 2006; International Patent Application No. PCT/US2008/072604, entitled "Use of additives for enhancing droplet actuation," filed on Aug. 8, 2008; and U.S. Patent Publication No. 20080283414, entitled "Electrowetting Devices," filed on May 17, 2007; the entire disclosures of which are incorporated herein by reference. The filler fluid may fill the entire gap of the droplet actuator or may coat one or more surfaces of the droplet actuator. Filler fluid may be conductive or non-conductive. A "filler material" is a solidified or hardened filler fluid, such as a solidified or hardened wax, fat or oil.

"Immobilize" with respect to magnetically responsive beads, means that the beads are substantially restrained in position in a droplet or in filler fluid on a droplet actuator. For example, in one embodiment, immobilized beads are sufficiently restrained in position to permit execution of a splitting operation on a droplet, yielding one droplet with substantially all of the beads and one droplet substantially lacking in the beads.

"Liquid Path" means a path suitable for conducting or flowing a liquid. A liquid path may be established in a substrate, such as a lumen path in a tube substrate (e.g., a capillary tube), or a channel, canal, duct, hole, opening, furrow or groove path in a solid substrate. A liquid path may be open (e.g., a furrow or groove in a surface through which liquid may flow) or closed (e.g., a tube). Often a liquid path will be established to flow liquid from one chamber to another, such as from a liquid reservoir through the liquid path and into a droplet operations gap of a droplet actuator, or from a liquid reservoir, through a liquid path, and into a second liquid path.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, $CoO$, $NiO$, $Mn_2O_3$, $Cr_2O_3$, and $CoMnP$.

"Washing" with respect to washing a magnetically responsive bead means reducing the amount and/or concentration of one or more substances in contact with the magnetically responsive bead or exposed to the magnetically responsive bead from a droplet in contact with the magnetically responsive bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Examples of suitable washing techniques are described in Pamula et al., U.S. Pat. No. 7,439,014, entitled "Droplet-Based Surface Modification and Washing," granted on Oct. 21, 2008, the entire disclosure of which is incorporated herein by reference.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid may be either in direct contact with the electrode/array/matrix/surface, or may be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

DESCRIPTION

Figure 1:
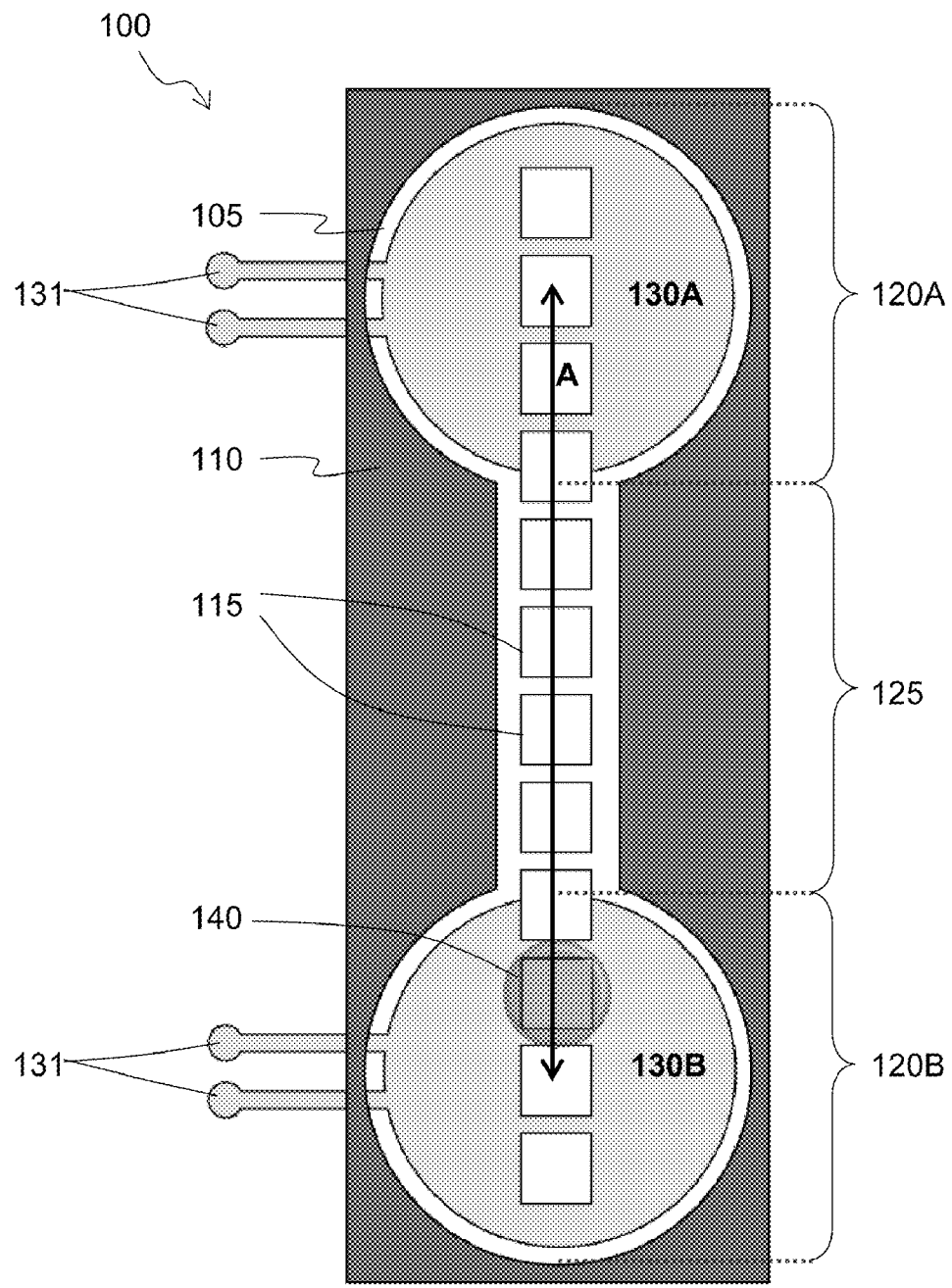
FIG. 1 illustrates a thermal cycling path on a droplet actuator substrate.

The invention provides droplet actuator devices, techniques and systems for making and using droplet actuators. Embodiments of the invention are useful for conducting droplet operations. Embodiments of the invention are useful for conducting assays employing thermal cycling of droplets, such as thermal cycling of droplets to amplify nucleic acids. The diverse thermal cycling protocols of the invention have various advantages relative to the state-of-the-art. In some cases, the protocols do not require that the heaters or the droplet actuator are thermally cycled. In other cases, it is not necessary for the nucleic acid amplification and the detection to occur at the same time or in the same location. In still other cases, it may not be necessary for a detection reagent to be present in the reaction during thermal cycling, e.g., the detection reagent may be added after thermal cycling, such as by combining the thermal cycled droplet with a droplet including detection reagent. In some embodiments, it is not necessary for the detection to occur during thermal cycling, i.e., detection may occur upon completion of thermal cycling or after thermal cycling. In still other cases, it is not necessary for the signal from an individual reaction to be measured more than once. Further, it may not be necessary for the signal associated with any particular number of cycles to be determined in any particular order. Any particular thermal cycling protocol of the invention may have one or more of these and other advantages.

The invention provides droplet actuators and improved methods of performing nucleic acid analyses, such as PCR, on a droplet actuator. For example, the invention provides methods of manipulating magnetically responsive beads in order to improve detection of an amplified target (e.g., nucleic acid). The invention also provides for the use of polar fluorophores in a droplet actuator-driven amplification protocol in order to improve detection of an amplified target. The invention also provides methods (e.g., passivation) for substantially reducing and/or eliminating loss of nucleic acid targets and PCR reagents during droplet operations. The invention also provides for a droplet actuator that has increased gap size in order to improve droplet stability during droplet operations. The invention also provides a method of reducing carry-over and cross-contamination between amplification reaction droplets. The invention further provides methods for concentrating and collecting target nucleic acid from a sample fluid.

In certain embodiments, multiple droplets including substantially identical compositions may be subjected to thermal cycling protocols in which different droplets or different sets of droplets are subjected to different numbers of cycles. When a droplet or set of droplets has completed a predetermined number of cycles, the droplet may be subjected to detection to determine the quantity of amplified product present in the droplet. A curve may be generated based on the detection of droplets at different thermal cycling endpoints and used to quantify a target present in an original sample. Numerous alternatives are possible within the scope of the invention in light of the invention as disclosed herein.

The devices, techniques and systems of the invention have numerous advantages relative to the state of the art, including but not limited to reduction or elimination of cross contamination between droplets on a droplet actuator and other droplets, filler fluids, and/or droplet actuator surfaces; cleaning of a droplet actuator between uses to diminish or eliminate contamination.

7.1 Reducing Cross-Contamination

The invention provides droplet actuator devices and methods for conducting droplet operations. The invention may substantially reduce or eliminate cross-contamination and carry-over between droplets on a droplet actuator and other droplets, filler fluids, and/or droplet actuator surfaces. The invention may provide for cleaning of a droplet actuator between uses to diminish or eliminate contamination. The invention is generally described with reference to nucleic acid amplification reactions like PCR, but it will be appreciated that the methods are suitable for any type of assay in which cross-contamination or carry-over between droplets is an issue.

FIG. 1 illustrates a thermal cycling path 100 on a droplet actuator substrate. Thermal cycling path 100 includes a droplet operations region 105. Droplet operations region 105 is established on a first substrate and may also include a second substrate arranged in a generally parallel fashion with respect to the first substrate to create a droplet operations gap therebetween for conducting droplet operations. Droplet operations region 105 is bounded by gasket 110 to prevent contaminants from entering or leaving droplet operations region 105. Where first and second substrates are present, gasket 110 may be provided in the droplet operations gap. Gasket 110 may serve as a seal for retaining filler fluid in droplet operations region 105 and/or as a spacer for establishing a droplet operations gap height of the droplet operations region 105.

Where gasket 110 retains a liquid filler fluid in droplet operations region 105, gasket 110 prevents contaminants in the filler fluid from contaminating other droplet operations regions on the droplet actuator substrate. Thus, where first and second substrates are present, gasket 110 may be provided in the droplet operations gap and arranged such that the filler fluid in droplet operations region 105 is completely bounded by the first and second substrates and the gasket. Various ports may be provided along any path from the droplet operations gap to an exterior of the droplet actuator or to another region of the droplet actuator for loading/unloading fluids to/from droplet operations region 105.

As illustrated, droplet operations region 105 includes two temperature control zones 120A and 120B, as well as a transition zone 125. Temperature control zones 120 are associated with temperature control elements 130A and 130B. Temperature control elements 130 are elements which control the temperature of filler fluid in their vicinity. Temperature control elements 130 may be electrically coupled to electrical contacts 131 for supplying electricity to the temperature control elements 130. Examples of suitable temperature control elements 130 include heaters and heat sinks. As illustrated, two temperature control zones 120A and 120B are present; however, it will be appreciated that any number of temperature control zones 120 may be included.

Temperature control zones 120 are connected by transition zone 125. Electrodes 115 in transition zone 125 may be utilized to shuttle droplets between temperature control zones. Transition zone 125 may in some embodiments be narrower than temperature control zones 120 in order to minimize fluid circulation between temperature control zones 120. As illustrated, a single transition zone 125 connects two temperature control zones 120; however, it will be appreciated that the temperature control zones 120 may have multiple transition zone 125 connections. Further, any number of temperature control zones 120 may be connected by any number of transition zones 125.

Droplet operations region 105 includes electrodes 115 associated with one or both of the first and second substrates. Electrodes 115 are configured for conducting one or more droplet operations. Electrodes 115 may, for example, be used to shuttle a droplet 140 back and forth between temperature zones 120A and 120B, e.g., in the direction illustrated by arrow A.

Figure 2:
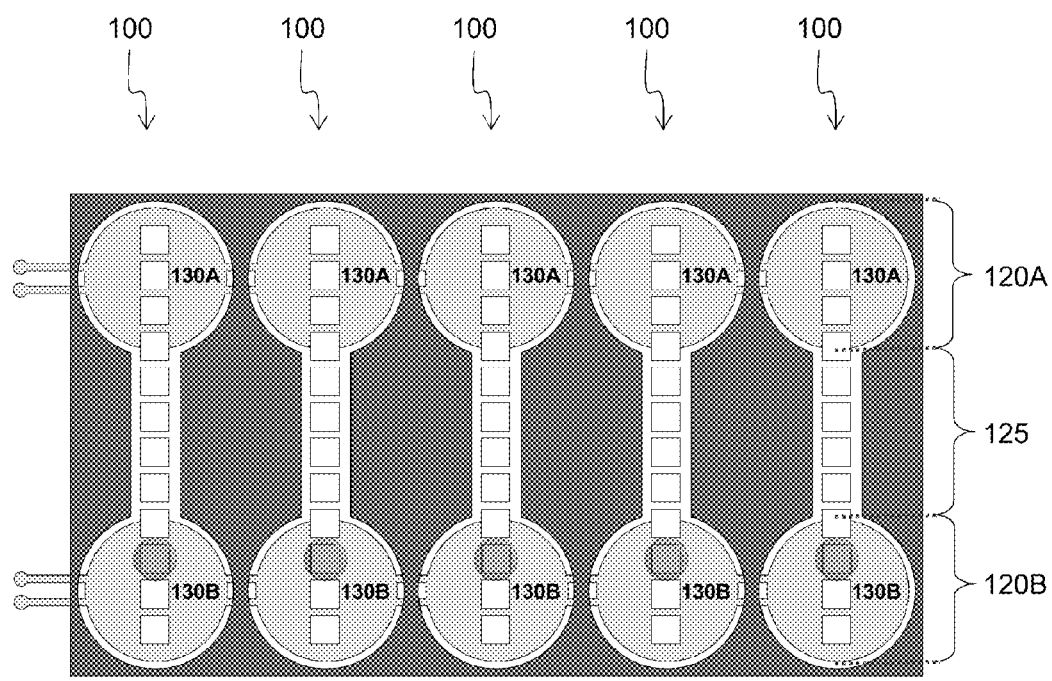
FIG. 2 illustrates a series of thermal cycling paths established on a droplet actuator substrate.

FIG. 2 illustrates a series of thermal cycling paths 100 established on a droplet actuator substrate. Temperature control elements 130 are illustrated as a series of generally disc-shaped heaters electrically coupled together in a series. However, it will be appreciated that temperature control elements 130 may be coupled in parallel to an electrical source or to separate electrical sources. Further, temperature control elements 130 may be combined. For example, elements 130A may be replaced by a single temperature control elements 130 associated with each temperature control zone 120A. Similarly, elements 130B may be replaced by a single temperature control elements 130 associated with each temperature control zone 120B.

Figure 3:
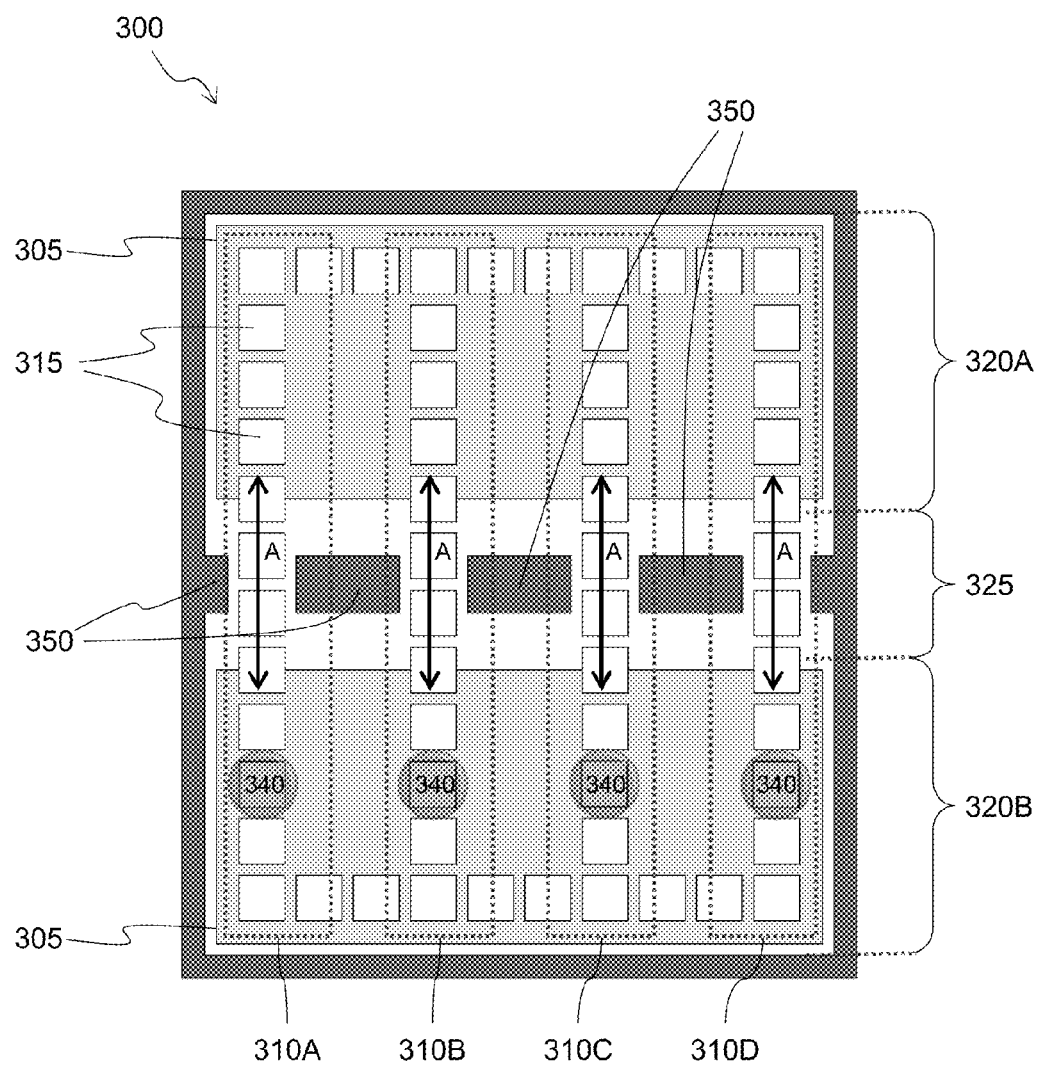
FIG. 3 illustrates another thermal cycling layout for a droplet actuator.

FIG. 3 illustrates another thermal cycling layout 300 for a droplet actuator. Thermal cycling layout 300 is similar to layout establishing thermal cycling paths 100 in FIGS. 1 and 2. However, thermal control elements 305 establishes temperature control zones 320A and 320B across multiple droplet shuttling paths 310A-310B. Droplet shuttling paths 310 are composed of droplet operations electrodes 315 configured to conduct one or more droplet operations, generally as described with reference to FIG. 1. In particular, droplet shuttling paths 310 employ droplet operations electrodes 315 to shuttle droplets 340 between thermal zones 320A and 320B in the direction illustrated by arrows A. Thermal cycling layout 300 may also include physical barriers configured to reduce filler fluid circulation between thermal zones 320A and 320B.

Figure 4:
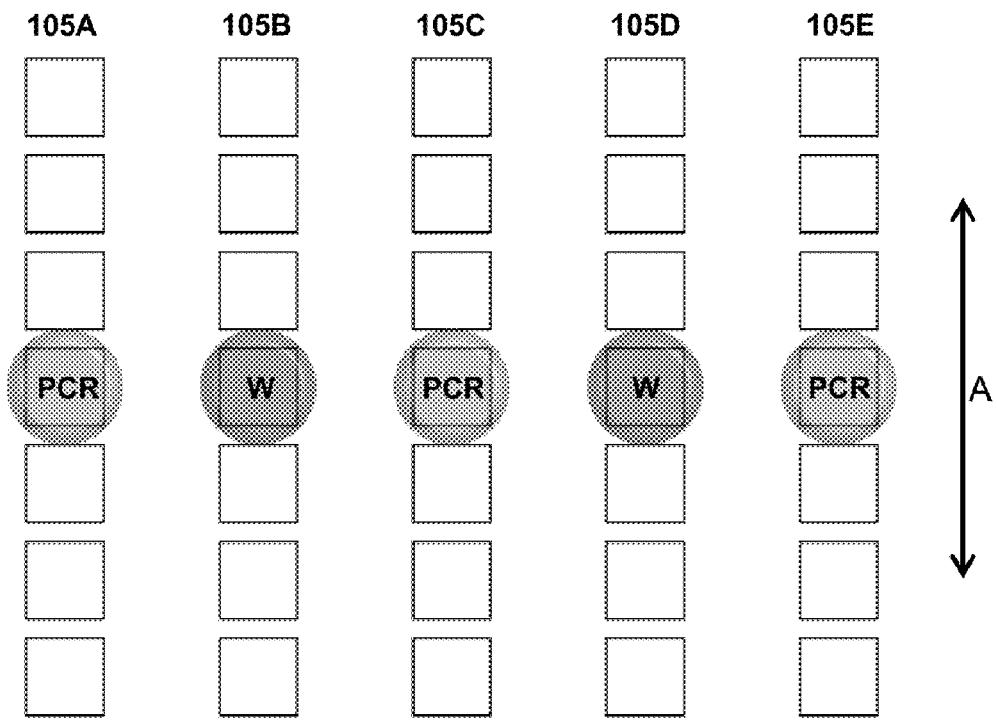
FIG. 4 illustrates a technique for reducing or eliminating cross contamination between droplets.

FIG. 4 illustrates a technique for reducing or eliminating cross contamination between droplets. Droplet shuttling paths 105A, 105B, 105C, 105D and 105E are provided on a droplet actuator substrate. Droplets are shuttled between thermal zones (not shown) in the direction indicated by arrow A. Paths 105A, 105C and 105E include sample droplets, illustrated here as PCR droplets. Wash droplets W are interposed on paths 105B and 105D between paths including sample droplets. As sample droplets are shuttled between temperature zones, wash droplets are shuttled between sample droplet paths. Wash droplets W may include compounds that degrade contaminants, such as DNA degrading enzymes. Wash droplets W may include components that bind to contaminants, such as DNA-binding beads. Wash droplets W may be shuttled in the same direction or in opposite directions relative to the sample droplets. They may be shuttled in positions immediately adjacent to sample droplets and/or in positions which are offset relative to sample droplets. Wash droplets W may optionally include nucleic acid amplification reagents so that they also function as negative reaction controls where the detection of amplified nucleic acid within a wash droplet provides an indication that contamination was detectable within a wash droplet.

Figure 5:
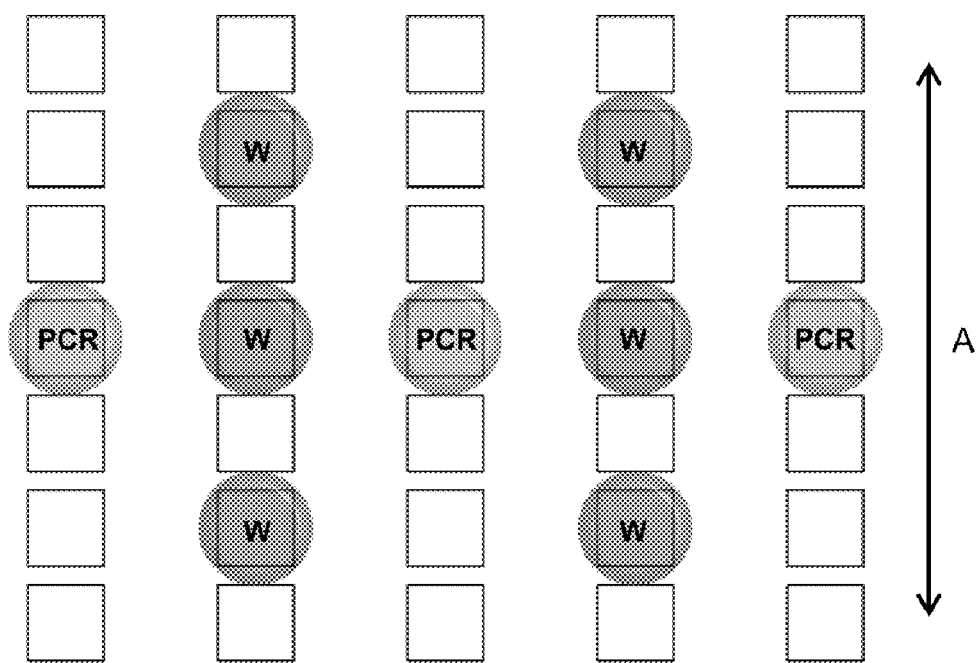
FIG. 5 illustrates a technique substantially similar to the technique illustrated in FIG. 4, except that multiple wash droplets are interposed on paths between sample droplets.

FIG. 5 illustrates a technique substantially similar to the technique illustrated in FIG. 4, except that multiple wash droplets are interposed on paths between sample droplets. In an alternative embodiment, multiple wash droplet paths are interposed between sample droplet paths, with one or more wash droplets in each wash droplet path.

Figure 6:
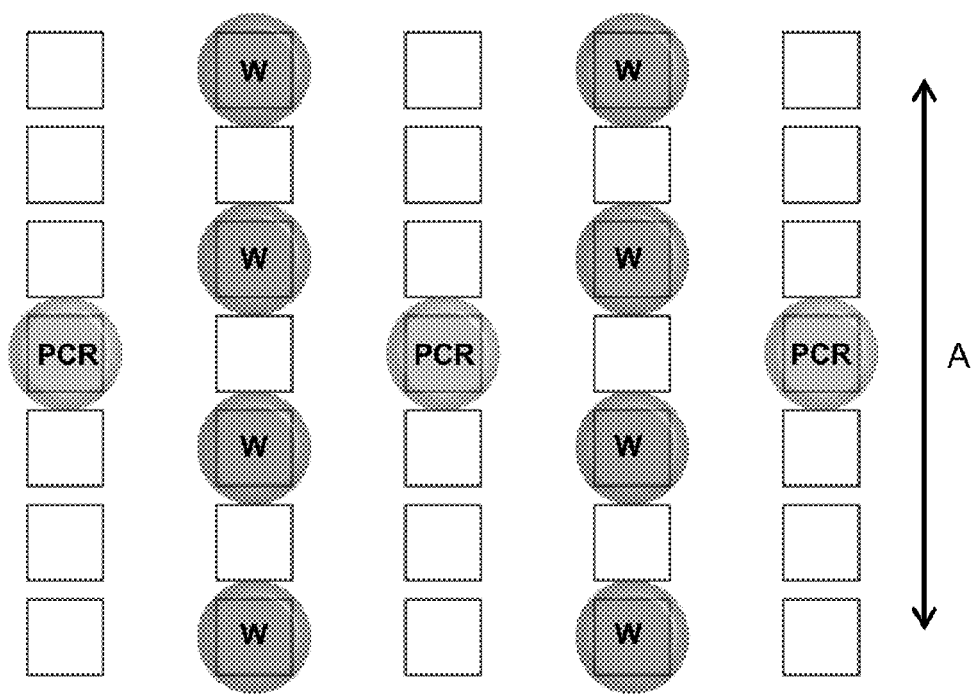
FIG. 6 illustrates a technique substantially similar to the technique illustrated in FIG. 5, except that the wash droplets are offset by one electrode relative to the sample droplets.

FIG. 6 illustrates a technique substantially similar to the technique illustrated in FIG. 5, except that the wash droplets are offset by one electrode relative to the sample droplets.

Figure 7:
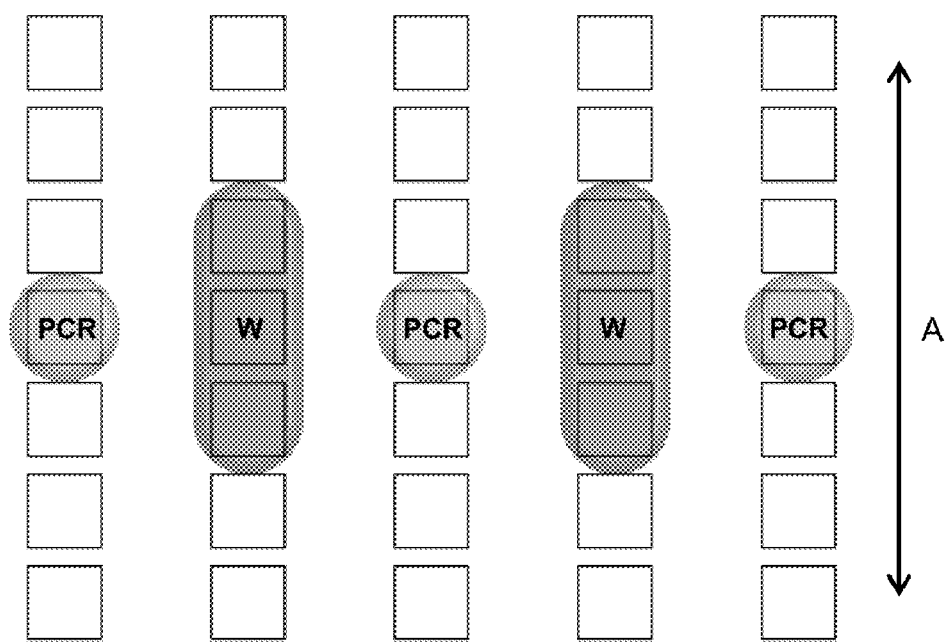
FIG. 7 illustrates a technique substantially similar to the technique illustrated in FIGS. 4 and 5, except that the wash droplets are replaced by elongated slug-shaped wash droplets.

FIG. 7 illustrates a technique substantially similar to the technique illustrated in FIGS. 4 and 5, except that the wash droplets are replaced by elongated slug-shaped wash droplets.

Figure 8:
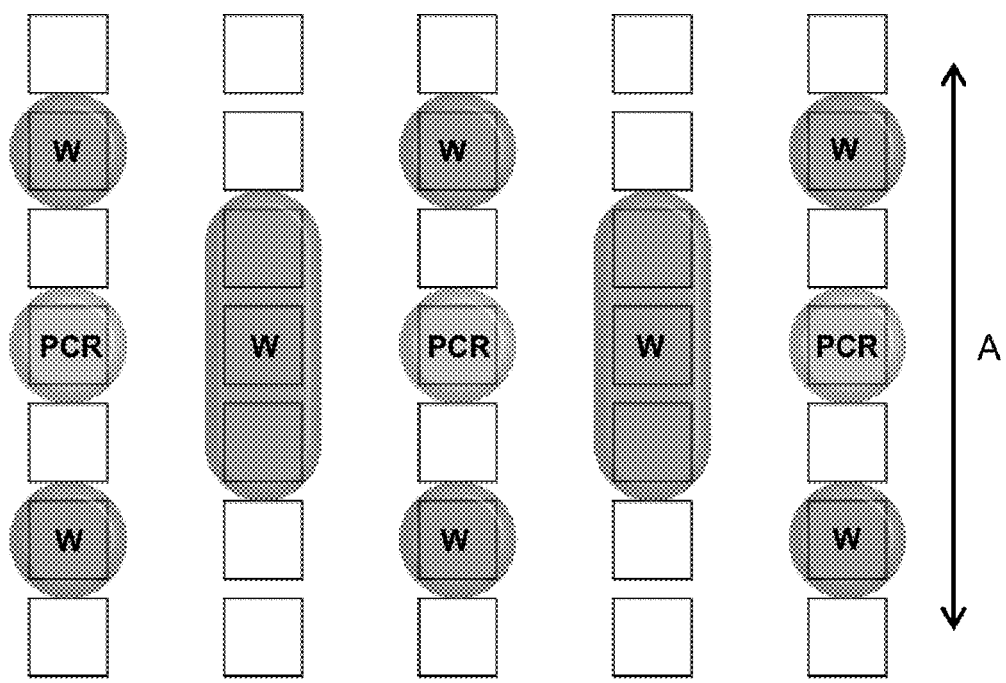
FIG. 8 illustrates a technique substantially similar to the technique illustrated in FIG. 7, except that the elongated wash slugs are further supplemented with wash droplets in the sample droplet paths before and after the sample droplets.

FIG. 8 illustrates a technique substantially similar to the technique illustrated in FIG. 7, except that the elongated wash slugs are further supplemented with wash droplets in the sample droplet paths before and after the sample droplets. Similarly, wash droplets in the sample droplet paths before and after the sample droplets may also be included in any of the preceding figures.

Figure 9:
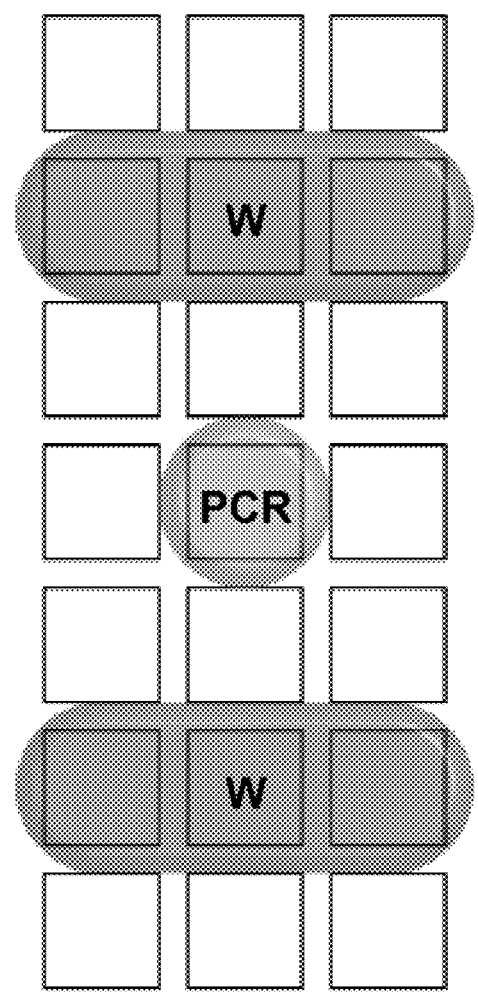
FIG. 9 illustrates a technique substantially similar to the preceding techniques, except that the wash droplets are provided as horizontal shaped wash droplets before and after the sample droplets.

FIG. 9 illustrates a technique substantially similar to the preceding techniques, except that the wash droplets are provided as horizontal shaped wash droplets before and after the sample droplets. In a similar embodiment, the wash droplet slugs may be replaced with 2×, 3×, 4×, 5×, 6×, 7×, 8×, 9× or larger droplets of any shape.

Figure 10:
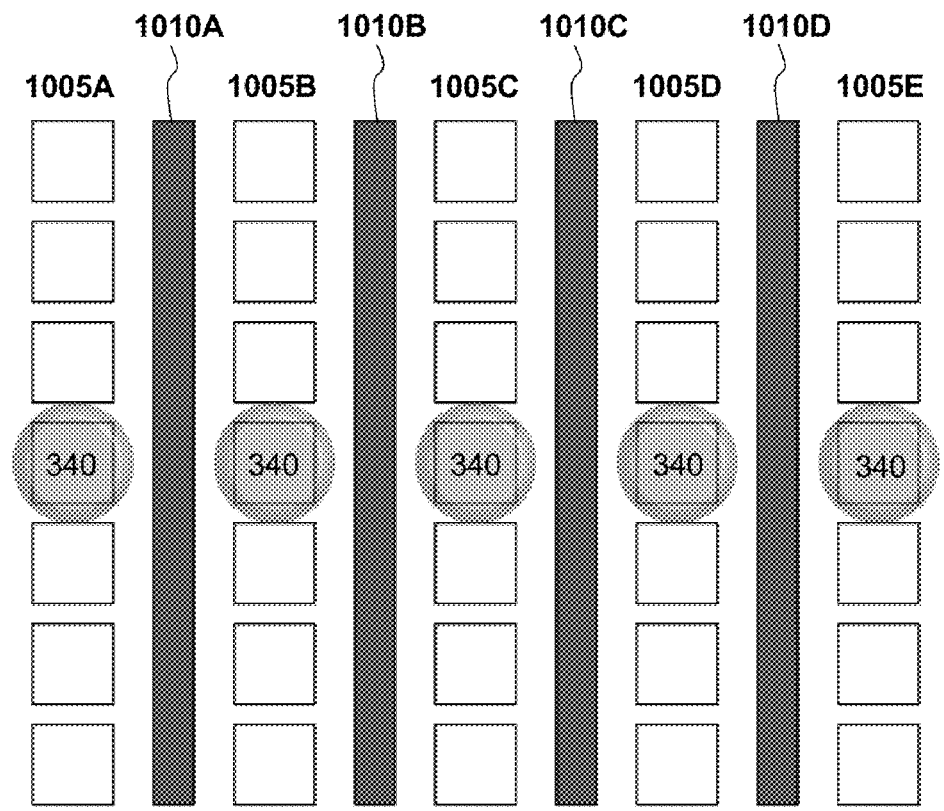
FIG. 10 illustrates an embodiment that is similar to the embodiment illustrated in FIG. 2 except that elongated physical barriers are included between sample paths preventing exchange of filler fluid or filler fluid constituents between paths.

FIG. 10 illustrates an embodiment that is similar to the embodiment illustrated in FIG. 2 except that elongated physical barriers 1010A, 1010B, 1010C and 1010D are included between sample paths 1005A, 1005B, 1005C, 1005D, and 1005E, preventing exchange of filler fluid or filler fluid constituents between paths or regions.

Figure 11:
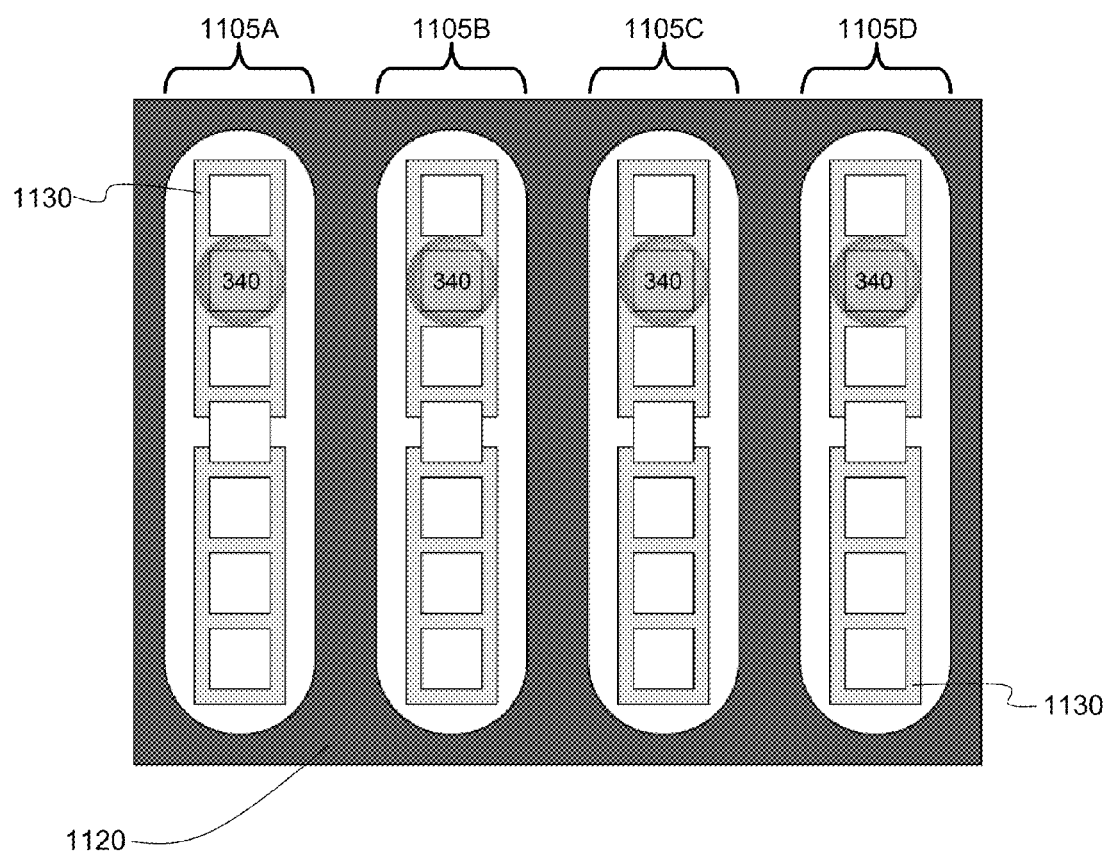
FIG. 11 illustrates an embodiment in which the filler fluid is provided as a substance that substantially solidifies at storage temperature and melts in the vicinity of heaters at temperatures required for operation.

FIG. 11 illustrates an embodiment in which the filler fluid is provided as a substance that substantially solidifies at storage temperature and melts in the vicinity of heaters at temperatures required for operation. Heaters 1130 are provided having a shape which generally corresponds to the shape of the desired droplet operations paths 1105. Four droplet operations paths 1105A, 1105B, 1105C and 1105D are illustrated here, but it will be appreciated that any number of paths may be provided. Upon heating the substantially solidified filler material, a portion the filler material melts to form fluid filled droplet operations paths 1105 surrounded by filler material that remains substantially solid, thereby serving as a barrier 1120 to contaminants passing via liquid filler fluid from one droplet operations path 1105 to another. In one embodiment, the filler material is selected to remain solid at temperatures below those temperatures required for conducting nucleic acid amplification and to melt at temperatures required for conducting nucleic acid amplification.

Figure 12A:
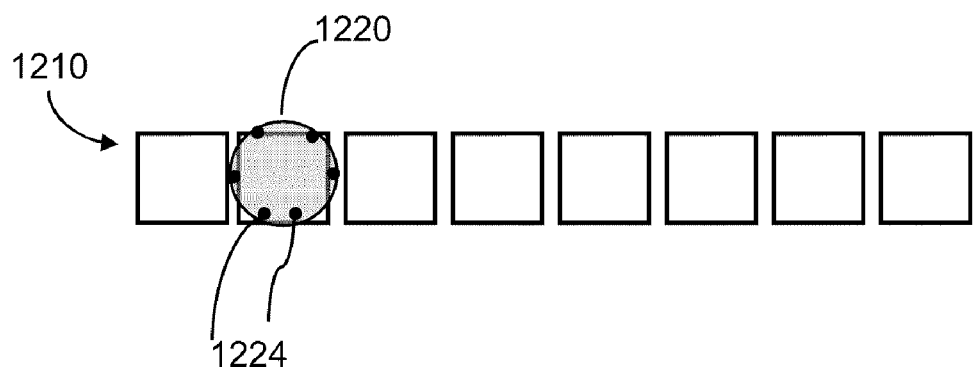
FIGS. 12A and 12B illustrate another technique for reducing or eliminating cross contamination between droplets.
Figure 12B:
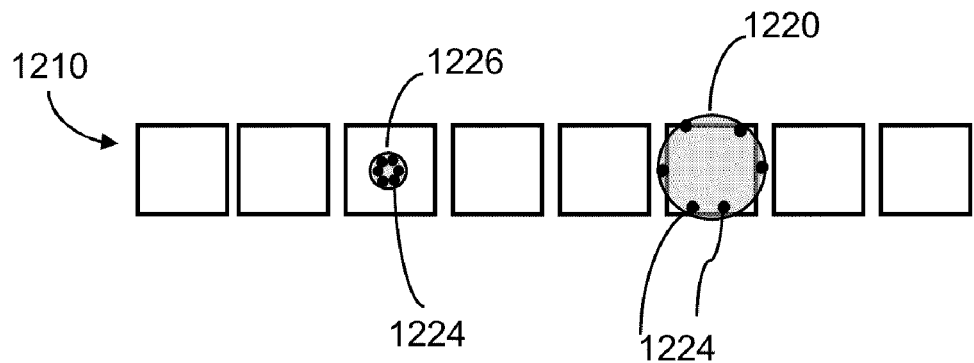

FIGS. 12A and 12B illustrate another technique for reducing or eliminating cross contamination between droplets. A path or array of droplet operations electrodes 1210 is provided on a droplet actuator substrate. Droplet operations electrodes 1210 are configured for conducting one or more droplet operations. As shown in FIG. 12A, droplet operations electrodes 1210 may, for example, be used to transport a droplet 1220. Droplet 1220 may be any droplet that potentially includes a contaminating substance, i.e., a substance may contaminate another droplet. For example, droplet 1220 may be an assay droplet, such as a droplet used in an immunoassay, sequencing assay, nucleic acid amplification assay, and/or enzymatic assay droplet. The contaminating substance may, for example, be a target substance, such as a nucleic acid in a nucleic acid amplification reaction; a non-target substance, such as a non-target protein in an immunoassay sample; and/or a reagent, such as an enzyme.

Droplet 1220 may contain a quantity of surfactant-enzyme complex 1224. In one example, complex 1224 may be a surfactant-DNase complex (i.e., a DNA degrading complex). Because of the surfactant moiety, substantially all of complex 1224 is trapped at the surface of droplet 1220. A quantity of complex 1224 may be selected such that the concentration of the enzyme moiety (e.g., DNase) is sufficiently low and, therefore, substantially inactive in droplet 1220.

Transport of droplet 1220 along droplet operations electrodes 1210 may result in the formation of a minidroplet 1226 that may be left behind on a certain droplet operations electrode 1210, as shown in FIG. 12B. Minidroplet 1226 may include all the components of droplet 1220, such as DNA and complex 1224. As a result, minidroplet 1226 may become a source of DNA contamination in subsequent droplet operations that may occur along droplet operations electrodes 1210.

Minidroplet 1226 may, for example, be 1/100 of the diameter of droplet 1220. The smaller diameter of minidroplet 1226 provides for a substantially higher surface area to volume ratio, e.g., 100× higher. An increased surface area to volume ratio may provide for a higher concentration of complex 1224 in minidroplet 1226 (e.g., 100× higher). However, because of the increased concentration of complex 1224 in minidroplet 1226, rapid degradation of DNA in minidroplet 1226 may be achieved, substantially preventing or reducing cross-contamination caused by minidroplet 1226.

As an example, the enzyme may be conjugated to a polyalkalene glycol (PAG) moiety (e.g., polyethylene glycol (PEG), polypropylene glycol, etc.) of a PAG-alkyl polymer. A variety of methods are known in the art for accomplishing such conjugation: U.S. Pat. No. 4,088,538 describes an enzymatically active polymer-enzyme conjugate of an enzyme covalently linked to PEG; U.S. Pat. No. 4,496,689 describes a covalently attached complex of α-1 protease inhibitor with a polymer such as PEG or methoxypoly(ethylene glycol); Abuchowski et al., J. Biol. Chem. 252: 3578 (1977) describes the covalent attachment of mPEG to an amine group of bovine serum albumin; U.S. Pat. No. 4,414,147 describes conjugating an interferon to the anhydride of a dicarboxylic acid, such as poly(ethylene succinic anhydride); and International Patent Publication No. WO/1987/00056 describes conjugation of PEG and poly(oxyethylated) polyols to such proteins as interferon-β, interleukin-2 and immunotoxins. The entire disclosure of each of these documents is incorporated herein by reference.

Another mode of attaching PEG to the enzyme is by oxidation of glycosyl residues on a peptide. The oxidized sugar is utilized as a locus for attaching a PEG moiety to the peptide. For example: International Patent Pub. No. WO/1994/05332) describes the use of a hydrazine- or amino-PEG to add PEG to a glycoprotein. The glycosyl moieties are oxidized to the corresponding aldehydes, which are subsequently coupled to the amino-PEG; International Patent Pub. No. WO/1996/40731 describes coupling of a PEG to an immunoglobulin molecule by enzymatically oxidizing a glycan on the immunoglobulin and then contacting the glycan with an amino-PEG molecule. The surfactant is coupled at one or more moieties of the enzyme at which conjugation does not unduly inhibit the activity of the enzyme.

Figure 13:
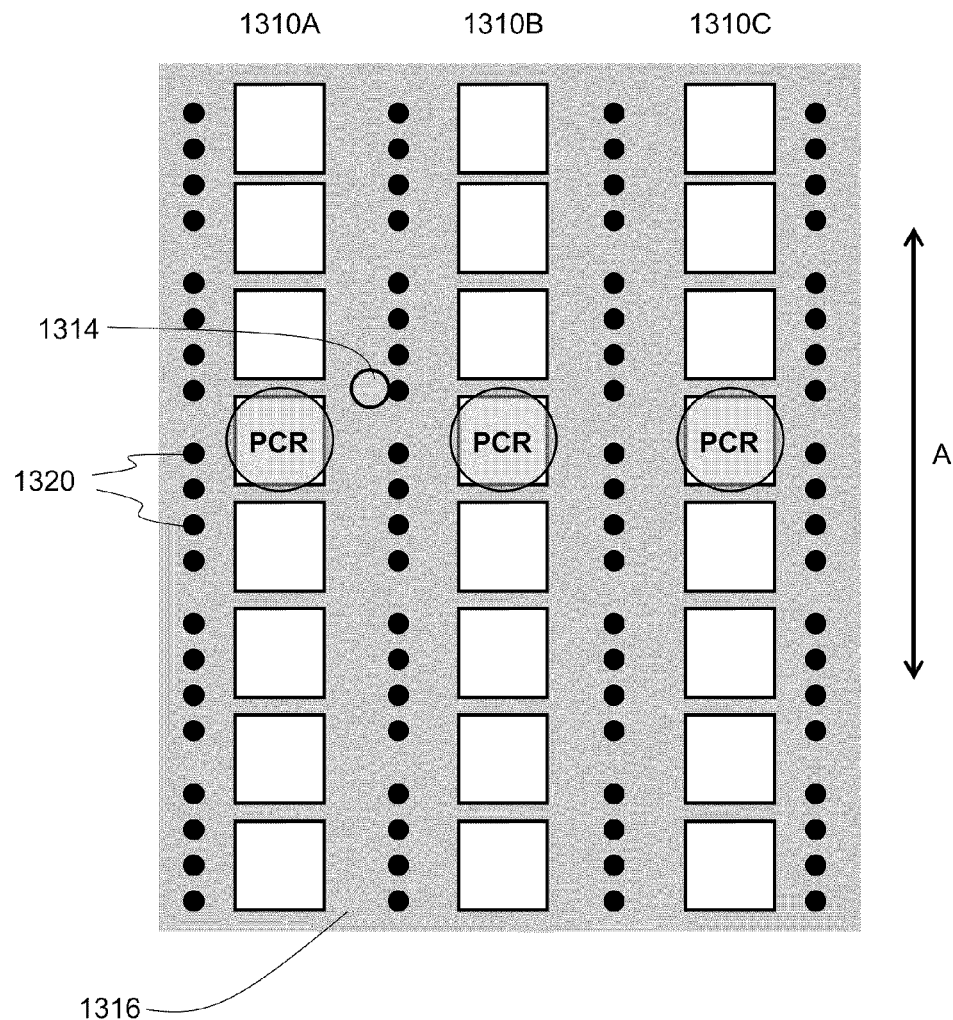
FIG. 13 illustrates another technique for reducing or eliminating cross contamination between droplets.

FIG. 13 illustrates another technique for reducing or eliminating cross contamination between droplets. In this embodiment, droplet operation paths 1310A, 1310B, and 1310C are provided on a droplet actuator substrate. Three droplet operations paths 1310A, 1310B, and 1310C are illustrated here, but it will be appreciated that any number of paths may be provided. Paths 1310A, 1310B, and 1310C include sample droplets, illustrated here as PCR droplets. Droplets are shuttled between thermal zones (not shown) in, for example, the direction indicated by arrow A. Shuttling of droplets may result in the formation of minidroplet 1314 that may be dispersed into filler fluid 1316. Minidroplet 1314 may contain DNA and, therefore, become a source of contamination to other droplet operation paths.

Filler fluid 1316 includes a quantity of surfactant-enzyme complexes 1320. In this example, complexes 1320 may be a surfactant-DNase complex used to degrade DNA. Complexes 1320 provide a barrier between paths 1310A, 1310B, and 1310C such that complexes 1320 degrade the DNA in minidroplet 1314 and substantially prevent or reduce cross-contamination between paths.

In an alternative embodiment, the examples illustrated in FIGS. 12A, 12B, and 13 may be applied to reduce cross-contamination of other materials in a droplet actuator. For example, a surfactant-protease complex may be used to substantially prevent or reduce protein carry-over during droplet operations.

Figure 14:
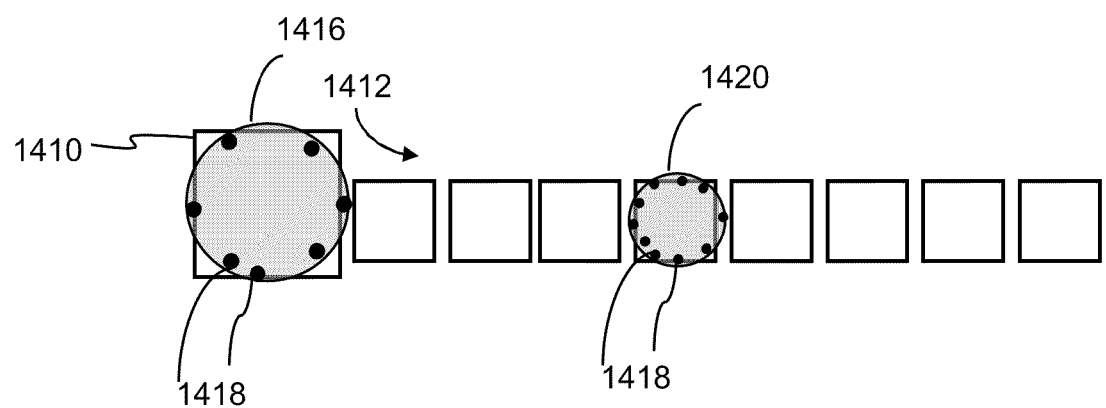
FIG. 14 illustrates an embodiment that uses the principle of surface area to volume ratio and surface-active enzyme complexes that is illustrated in FIGS. 12A and 12B to initiate a reaction on a droplet actuator.

FIG. 14 illustrates an embodiment that uses the principle of surface area to volume ratio and surface-active enzyme complexes that is illustrated in FIGS. 12A and 12B to initiate a reaction on a droplet actuator.

In this example, a reservoir electrode 1410 and a path or array of droplet operations electrodes 1412 are provided on a droplet actuator substrate. A quantity of sample fluid 1416 that contains a quantity of surfactant-enzyme complexes 1418 is provided at reservoir electrode 1410. Because of the surfactant moiety, substantially all complex 1418 are trapped at the surface of sample fluid 1416. A quantity of complex 1418 may be selected such that the concentration of the enzyme moiety is sufficiently low and, therefore, substantially inactive in sample fluid 1416.

Reservoir electrode 1410 is configured to dispense unit sized droplets 1420 onto droplet operations electrodes 1412. Droplet operations electrodes 1412 are configured for conducting one or more droplet operations for processing the unit sized droplets 1420.

The volume of sample fluid 1416 on reservoir electrode 1410 is substantially greater than the volume of unit sized droplet 1420. For example, the volume of sample fluid 1416 may be about 10 to about 1,000 times greater than the volume of unit sized droplet 1420. The smaller volume of unit sized droplet 1420, relative to sample fluid 1416, provides for a substantially higher surface area to volume ratio. An increased surface area to volume ratio may provide for a higher concentration of complex 1418 in unit sized droplet 1420. Increased concentration of complex 1418 in unit sized droplet 1420 is sufficient to initiate a reaction.

In an alternative embodiment, reservoir electrode 1410 is replaced with other droplet operations electrodes 1412. In this example, a sample droplet containing a quantity of surfactant-enzyme complexes may be split using droplet operations to vary its surface area to volume ratio and initiate a reaction.

In some embodiments, the droplet actuator is configured for replacement of filler fluid. In some applications, it will be useful to provide for repeated uses of a droplet actuator. Where contamination of filler fluid is a problem, it may be useful to replace some portion or all of the filler fluid in a droplet actuator between assay runs. The technique may be useful with a wide variety of droplet protocols, including for example, protocols for amplification, sequencing, immunoassays, enzymatic assays, and others. In one embodiment, the filler fluid is substantially completely replaced. Replacement may be automated. Filler fluid may be tested following each run, and filler fluid may be replaced when a predetermined level of contamination is detected. Replacement may be automatic. In some cases, replacement may occur periodically, e.g., after every 1, 2, 3, 4, 5 or more runs.

Figure 15:
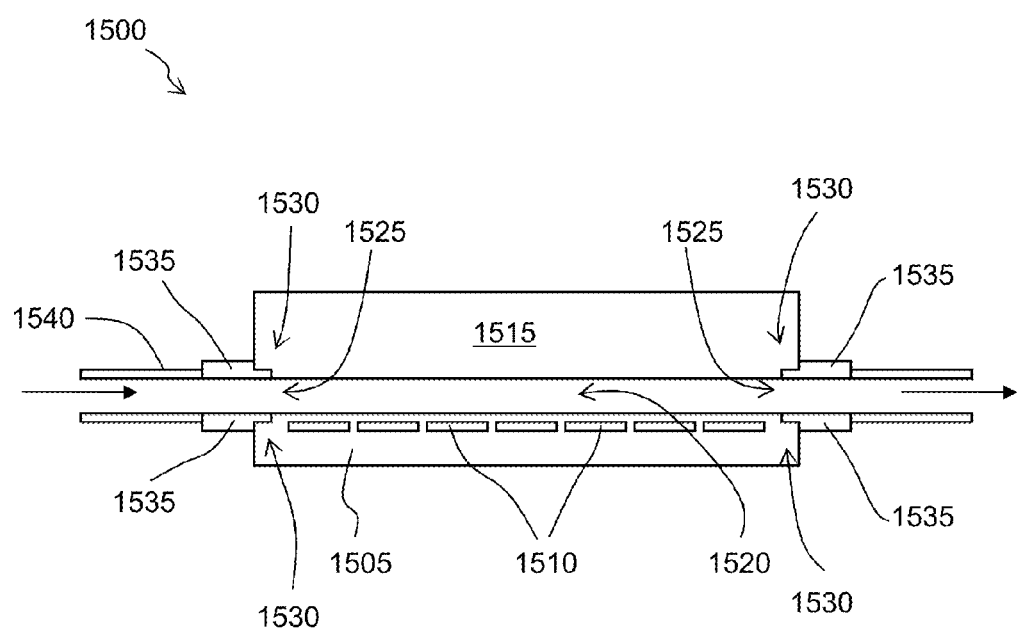
FIG. 15 illustrates a sectional side view of droplet actuator configured for flow-through replacement of filler fluid.

FIG. 15 illustrates a sectional side view of droplet actuator 1500 configured for flow-through replacement of filler fluid. Droplet actuator 1500 includes base substrate 1505 including electrodes 1510 configured for conducting one or more droplet operations. Droplet actuator 1500 also includes top substrate 1515 separated from base substrate 1505 to yield droplet operations gap 1520. Droplet actuator 1500 includes lateral openings 1525 for flowing filler fluid through droplet operations gap 1520. Lateral openings 1525 may include fittings 1530 configured to mate with one or more corresponding fittings 1535 on an external filler fluid source or filler fluid destination. Fittings 1535 may be associated with a conduit 1540 establishing a liquid path from an external filler fluid source (not shown), through conduit 1540, through fittings 1530 and 1535 and into droplet operations gap 1520. Fittings 1535 may be associated with a conduit establishing a liquid path from droplet operations gap 1520, through fittings 1530 and 1535, through conduit 1540, and into an external filler fluid destination (not shown).

Figure 16:
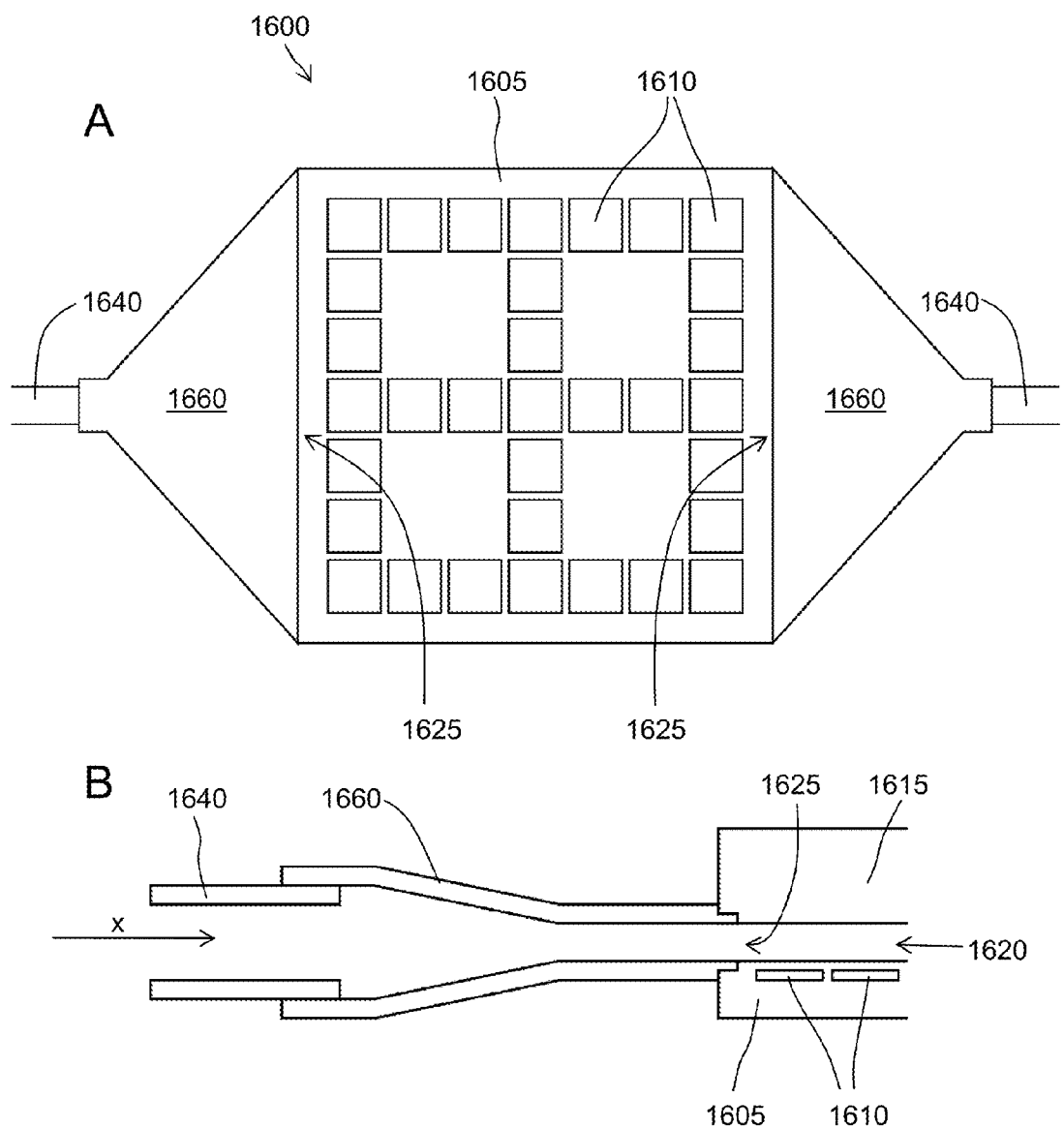
FIG. 16 shows a top view (FIG. 16A) and a sectional side view (FIG. 16B) of droplet actuator similar to the one illustrated in FIG. 15 configured for flow-through replacement of filler fluid.

FIG. 16 shows a top view (FIG. 16A) and a sectional side view (FIG. 16B) of a similar droplet actuator, 1600 configured for flow-through replacement of filler fluid. Droplet actuator 1600 includes base substrate 1605 including electrodes 1610 configured for conducting one or more droplet operations. Droplet actuator 1600 also includes top substrate 1615 separated from base substrate 1605 to yield droplet operations gap 1620. Droplet actuator 1600 includes lateral openings 1625 for flowing filler fluid through the droplet operations gap. Lateral openings 1625 may be associated with a manifold 1660 configured to flow liquid from conduit 1640 into the droplet operations gap and/or from the droplet operations gap into conduit 1640. Manifold 1660 may be configured with conduit 1640 and a liquid filler fluid source (not shown) to establish a liquid path from the external filler fluid source through conduit 1640, through manifold 1660, and into the droplet operations gap. Manifold 1660 may be configured with conduit 1640 and a liquid filler fluid destination (not shown) to establish a liquid path from the droplet operations gap, through manifold 1660, through conduit 1640, and into a liquid filler fluid destination. Manifold 1660 may include an opening 1662 suitable for coupling directly or indirectly to conduit 1640. Manifold 1660 may include an opening 1664 suitable for coupling directly or indirectly to the droplet actuator. Ideally, opening 1664 and opening 1625 have a shape which is substantially similar to a cross-section of the droplet operations gap 1620 in order to facilitate complete replacement of filler fluid in droplet operations gap 1620. One or more vents may be present in a substrate of droplet actuator 1600 and/or between the substrates (e.g., in a gasket) to permit escape of air bubbles which may be introduced in droplet operations gap 1620 during refilling. Arrow x indicates the direction of flow through conduit 1640, manifold 1660 and into droplet operations gap 1620.

Figure 17:
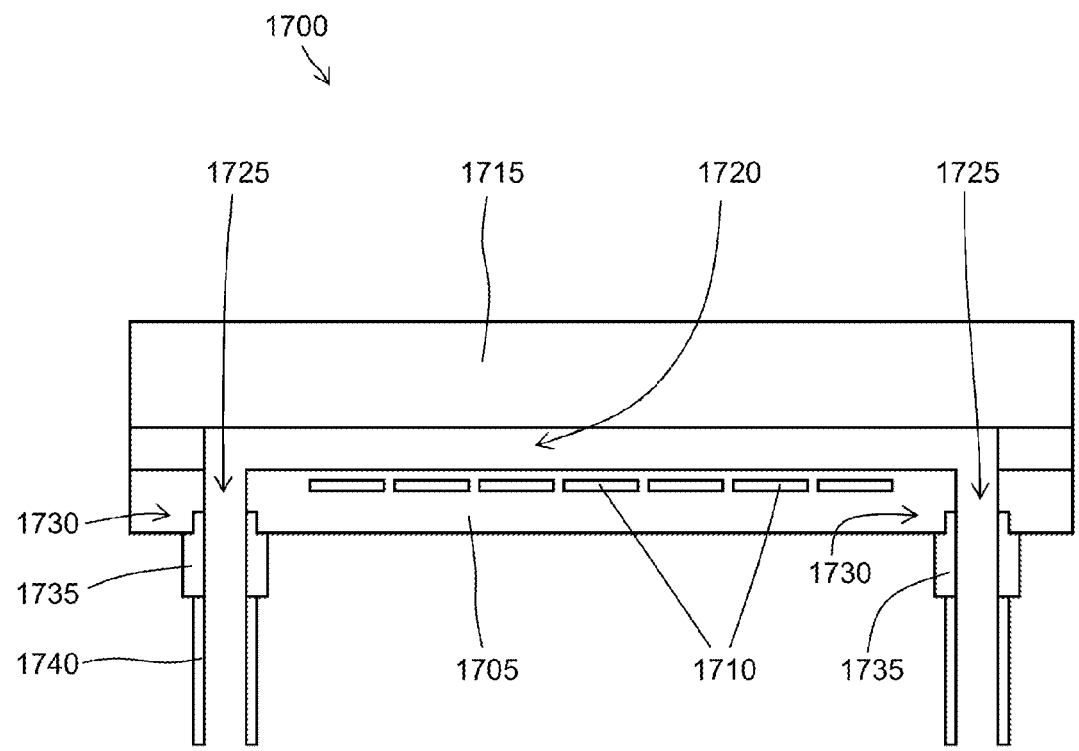
FIG. 17 illustrates a sectional side view of droplet actuator configured for flow-through replacement of filler fluid.

FIG. 17 illustrates a sectional side view of droplet actuator 1700 configured for flow-through replacement of filler fluid. Droplet actuator 1700 is like droplet actuator 1500 except that the openings for flowing fluid through the droplet actuator are located on the bottom of the droplet actuator. This arrangement may be useful for easy mounting of the droplet actuator in a system which includes components for flowing liquids through the droplet operations gap. Droplet actuator 1700 includes base substrate 1705 including electrodes 1710 configured for conducting one or more droplet operations. Droplet actuator 1700 also includes top substrate 1715 separated from base substrate 1705 to yield droplet operations gap 1720. Gasket 1707 seals the droplet operations gap. Droplet actuator 1700 includes bottom openings 1725 for flowing filler fluid through droplet operations gap 1720. Bottom openings 1725 may include fittings 1730 configured to mate with one or more corresponding fittings 1735 associated with a liquid path for an external filler fluid source and/or filler fluid destination. As an example, suitable chip-to-tubing connections include NANOPORT™ assemblies (IDEX Corporation, Oak Harbor, Wash.). One or more fittings 1735 may be associated with a conduit 1740 establishing a liquid path from an external filler fluid source (not shown), through conduit 1740, through fittings 1730 and 1735 and into droplet operations gap 1720. One or more fittings 1735 may be associated with a conduit establishing a liquid path from droplet operations gap 1720, through fittings 1730 and 1735, through conduit 1740, and into an external filler fluid destination (not shown).

In various aspects of the invention, filler fluid may thus flow from filler fluid source through a liquid path through droplet operations gap and out of droplet operations gap into a second liquid path to a liquid filler fluid destination. In this manner, the filler fluid may be at least partially replaced. Flowing filler fluid through a droplet operations gap may substantially replace the filler fluid originally present in the droplet operations gap. In some cases, the filler fluid may be flowed into the droplet operations gap in an amount which is sufficient to replace the filler fluid in the droplet operations gap. In other cases, the filler fluid may be flowed through the droplet operations to flush the droplet operations gap. Upon completion of flushing, the droplet operations gap remains filled with filler fluid and ready for operation. In certain embodiments, the filler fluid used to flush the droplet operations gap may be heated in order to enhance cleaning in the droplet operations gap. In another embodiment, contamination in the droplet operations gap may be monitored during flushing of the filler fluid, and flushing may be stopped when a suitable level of cleaning has been achieved.

The methods of the invention may be used to replace at least about 50% of the filler fluid originally present in the droplet operations gap. The methods of the invention may be used to replace at least about 75% of the filler fluid originally present in the droplet operations gap. The methods of the invention may be used to replace at least about 90% of the filler fluid originally present in the droplet operations gap. The methods of the invention may be used to replace at least about 95% of the filler fluid originally present in the droplet operations gap. The methods of the invention may be used to replace at least about 99% of the filler fluid originally present in the droplet operations gap.

In other aspects of the invention, a cleaning fluid may be flowed through the droplet operations gap to clean the droplet actuator. Following cleaning, fresh filler fluid may be flowed into the droplet operations gap. For example, a solvent may be flowed through the droplet operations gap to clean the droplet actuator prior to flowing fresh filler fluid into the droplet operations gap. A solvent may be selected which is suitable for removing filler fluid without unduly damaging the surfaces of the droplet operations gap. In some cases, it may be desirable to dry the droplet actuator gap prior to reloading the droplet operations gap with filler fluid. In some cases, a gas, such as air, may be flowed through the droplet operations gap in order to dry the droplet operations gap prior to reloading the droplet operations gap with filler fluid.

A variety of liquids may be used as cleaning fluids in the methods of the invention. In one aspect, cleaning liquids may be selected in which both oil and water are soluble with low boiling point would be good cleaning agents. High boiling point cleaning fluids or cleaning fluid components may also be used. In one embodiment, a high boiling point cleaning fluid is used, followed by a lower boiling point rinse. A cooling fluid may be flowed through the droplet operations gap prior to loading filler fluid in order to bring the droplet actuator back to operational temperature.

Examples of suitable cleaning liquids include polar liquids such as acetone, isopropyl alcohol, ethanol, methanol, tetrahydrofuran, acetonitrile, and mixtures including one or more of these components. Mixtures of these solvents may also be used. Water soluble silicone oil derivatives can also be used. Water based cleaning liquids can also be used; preferably the cartridge is dried before refilling following use of water based cleaning liquids. Multicomponent mixtures may also be used. In one embodiment, the cleaning liquid includes one or more components having solubility in water and one or more components should have solubility in oil. Cleaning fluids may also include various catalysts or enzymes. For example, enzymes that degrade specific contaminants may be included. In some cases, oil is displaced with air or water and then the droplet operations gap is reloaded with filler fluid.

In flash assays, it may be useful to use wash droplets that include the trigger solution to clean droplet transport paths. Electrode paths that have been used to transport the substrate may be washed by transporting one or more wash droplets across some portion or all of the same area. The wash droplets may include the flash enzyme. For example, the wash droplet (s) may include luciferase or luciferase and ATP. As an example, acridinium ester (AE) may be used as a chemiluminescent label in a flash assay of the invention. The AE signal quickly rises to a high value, typically in less than about 10, 9, 8, 7, 6, 5, 4, 3, 2 or 1 seconds upon addition of the trigger solution. The signal decays to very low values, typically in less than about 60, 30, 20, or 10 seconds. This may eliminate contamination on the detection loop and the detection spot. However, contamination may still be present on the wash paths and the incubation region by free secondary antibody bound with AE which can potentially affect the subsequent assays performed on the same path. Transporting 1, 2, 3, 4, 5, 6, 7, 8, 9, 10, or more droplets of the AE trigger solution over the electrodes that are contaminated with antibody bound with AE would produce chemiluminescence which would decay quickly, substantially eliminating AE contamination.

Cleaning fluids may in various cases be acidic or basic, e.g., sodium hydroxide or potassium hydroxide in ethanol for high pH, or acetic acid or dilute HCl for low pH. In one embodiment, a multistep washing procedure is provided, starting with a solvent which has solubility in water followed by a liquid which has solubility in the first solvent.

Heated solvents can be used as cleaning fluids. The temperature may be selected to enhance cleaning without causing undue damage to the droplet actuator. Preferred temperatures will vary depending on materials used. In some cases, the temperature ranges from about 30° C. to about 125° C., preferably about 60° C. to about 115° C., more preferably about 75° C. to about 105° C. Preferred temperatures will vary depending on materials used. Where a polycarbonate top substrate is used, maximum temperatures will be close to 100° C. currently. Where a glass top substrate is used, maximum temperatures may be much higher, e.g., greater than 150° C.

In some cases, one or more droplet actuator surfaces include a coating, and the cleaning liquid is selected to remove a very thin layer of the coating during cleaning. For example, one or more droplet actuator surfaces include a hydrophobic coating, and the cleaning liquid is selected to remove a very thin layer of the hydrophobic coating during cleaning. Thus, a liquid in which the hydrophobic coating has a very slight solubility may be selected for use as a cleaning liquid. For example, the hydrophobic coating may include a fluorinated polymer. The cleaning liquid may include a fluorinated solvent, such as a fully fluorinated solvent or a partially fluorinated solvent. The cleaning liquid may include a fully fluorinated solvent dispersed in another solvent at very low concentration. The cleaning liquid may include a partially fluorinated liquid which has solubility in other organic solvents. The cleaning liquid may also be selected to deposit an additional thin hydrophobic coating over the existing hydrophobic coating. Whether the cleaning liquid modifies the hydrophobic coating by removing a thin layer or by depositing an additional amount of thin layer, the effect in either case is to "renew" the hydrophobic coating to its original condition.

7.2 Parallel Flow-Through

Figure 18:
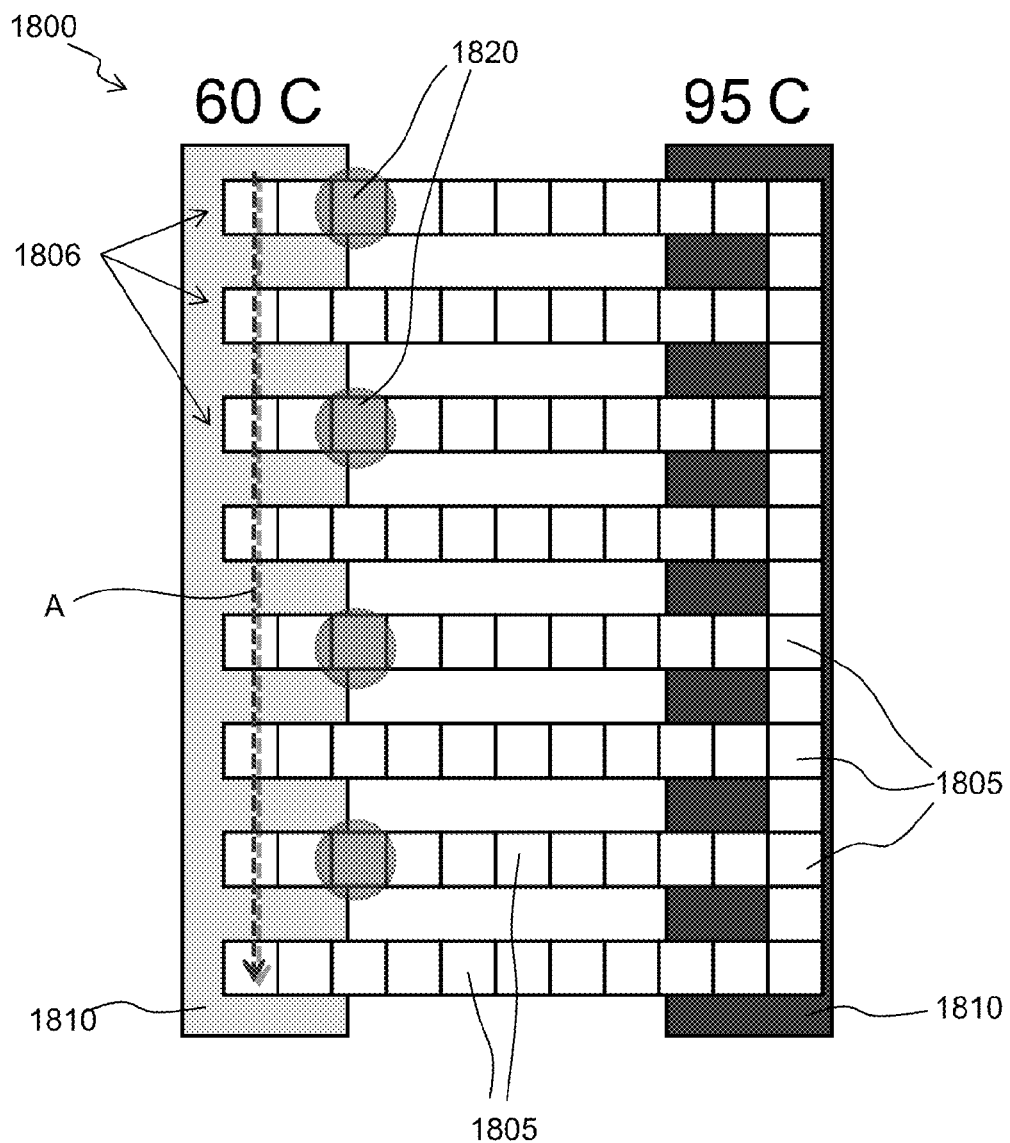
FIG. 18 illustrates an electrode configuration of a droplet actuator of the invention including electrode paths arranged for cycling droplets between thermal zones.

FIG. 18 illustrates an electrode configuration 1800 of a portion of a droplet actuator of the invention. Electrode configuration 1800 includes electrodes 1805, which are configured for conducting droplet operations on a surface of the droplet actuator. Electrode configuration 1800, like all electrode configurations of the invention, may be provided as part of a more extensive electrode configuration and/or a more extensive microfluidics network. The droplet actuator may be used to dispense and conduct other droplet operations on the droplet operations surface using a series of identical reaction droplets 1820, e.g. by dispensing the identical subsample droplets from a single-sample droplet (not shown) or another liquid source. Droplet operations electrodes 1805 may be configured to provide a series of droplet transport paths 1806. Droplet operations electrodes 1805 may be used to transport reaction droplets 1820 to one of the several droplet transport paths 1806.

Electrode configuration 1800 may also be associated with one or more temperature control elements 1810, such as heaters and/or heat sinks. Temperature control elements 1810 may be configured in any manner suitable for heating and/or cooling droplets on the droplet actuation surface. Temperature control elements 1810 may be used to establish temperature zones at the droplet operations surface. Where the droplet actuator includes two substrates separated to form a droplet operations gap for conducting droplet operations, temperature control elements 1810 may be configured to establish temperature zones in the droplet operations gap. Where the droplet operations gap is filled with a liquid filler fluid, temperature control elements 1810 may be configured to establish temperature zones within various regions of the filler fluid in the droplet operations gap. In the droplet operations transport paths 1806, droplets may be transported, using droplet operations mediated by droplet operations electrodes 1805, among temperature zones established by one or more temperature control elements 1810.

Any embodiments of the invention may be configured as part of a system. For example, a system may include a computer which controls droplet operations on the droplet actuator by controlling activation of electrodes of any of the electrode configurations of the invention. A system including the droplet actuator of FIG. 18 may be programmed to cycle droplets in each path for a different predetermined number of cycles. The detection may be accomplished on the thermal cycling paths themselves or the droplets may be transported elsewhere for detection. In the embodiment illustrated, droplets may be parked in the path marked A for detection by scanning a sensor across the droplets. Detection may be accomplished as the thermal cycling in each path is completed. Alternatively, some are all of the droplets may be parked following thermal cycling, and the sensor may scan the droplets one after another along the path marked A. Other suitable detection approaches are described herein.

Figure 19:
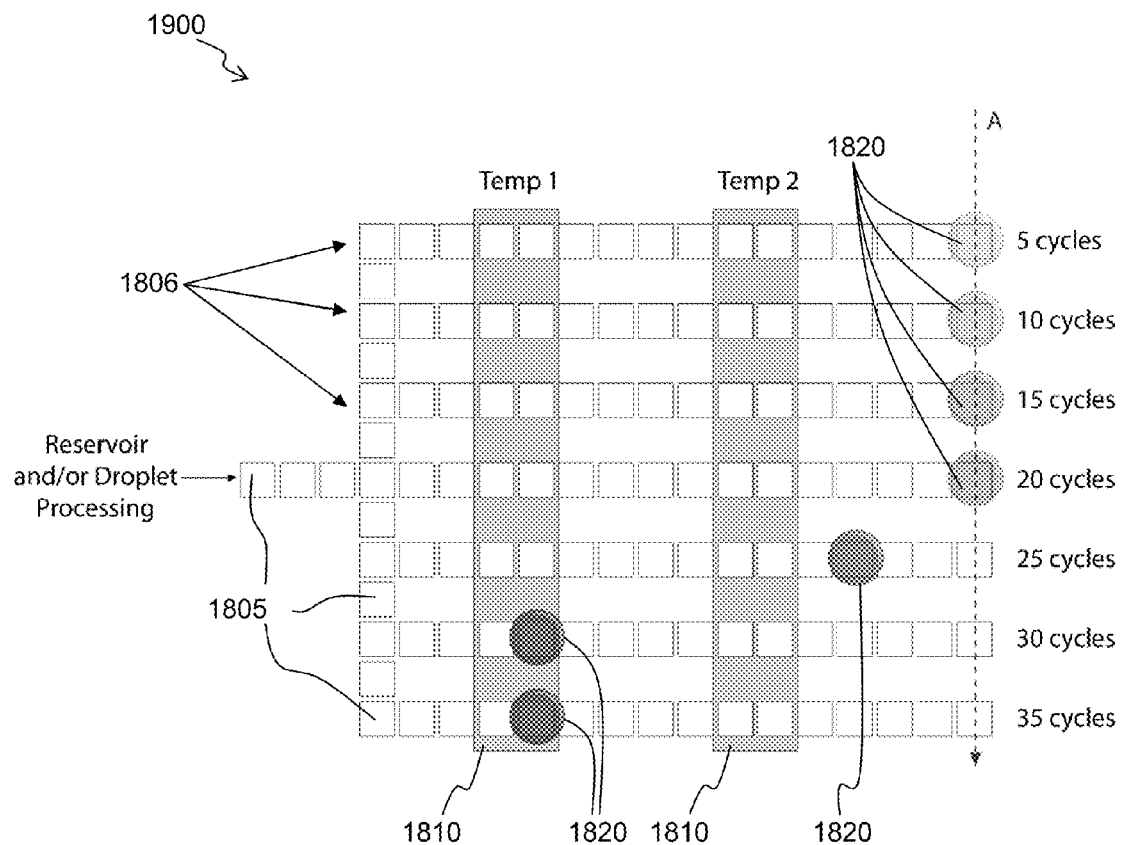
FIG. 19 illustrates an electrode configuration of a droplet actuator of the invention, which is similar to the electrode configuration shown in FIG. 18, except that certain paths are extended so that droplets may be parked away from temperature control elements.

FIG. 19 illustrates an electrode configuration 1900 of a droplet actuator of the invention. Configuration 1900 is similar to configuration 1800 and FIG. 18, except that paths 1806 are extended so that droplets may be parked away from temperature control elements 1810. In the example illustrated, droplets in the top path are subject to 5 cycles, droplets in the next path are subject to 10 cycles, and so on to the bottom path, in which droplets are subjected to 35 cycles. Any number of paths may be provided, and droplets 1820 in each path 1806 may be subjected to any number of cycles of transport between the temperature zones. Upon completion of a predetermined number of cycles, each droplet may be transported to a position in its respective path 1806 along the path marked A, where it may be subjected to detection. The detection may, for example involve sensing of a signal from the droplet. The signal strength may be used to quantify amplified nucleic acid in the droplet. Each droplet may be subjected to detection promptly upon completion of its predetermined number of cycles. Alternatively, the droplets may be parked and scanned at a later time by a sensor for detection.

Figure 20:
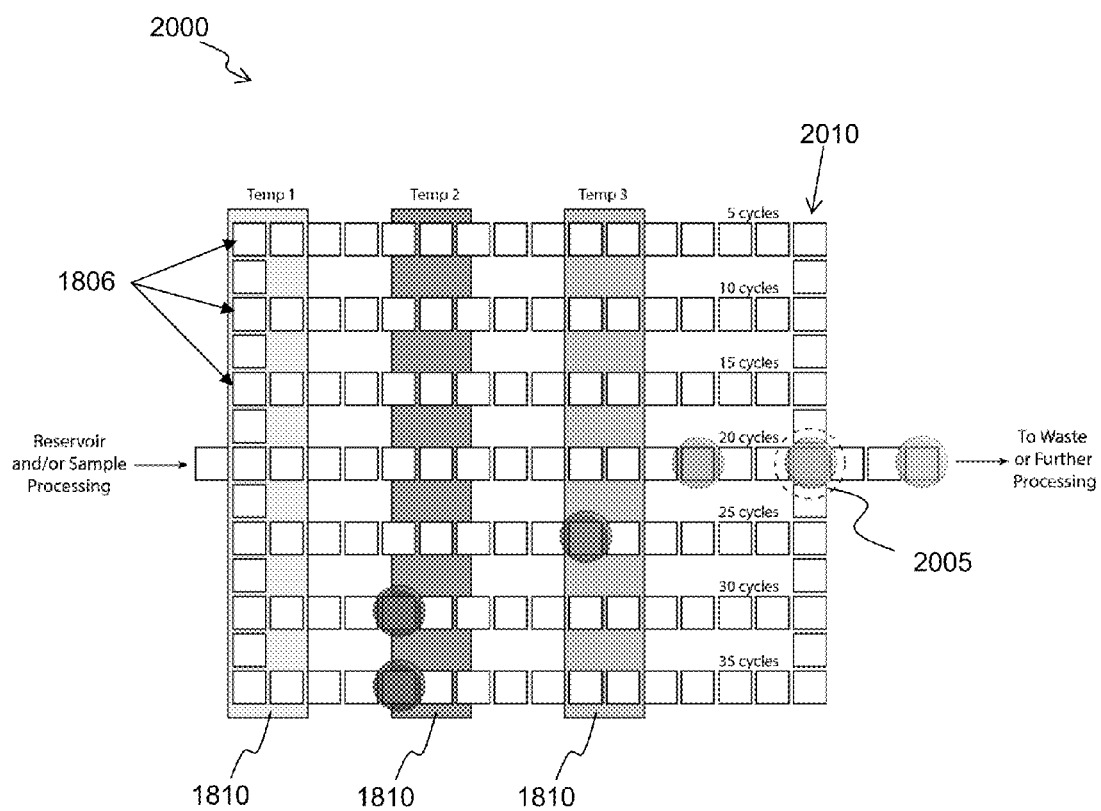
FIG. 20 illustrates an electrode configuration of a droplet actuator of the invention which is like the configuration illustrated in FIG. 19, except that a detection window is provided along with an electrode path arranged to permit droplets to be transported into the presence of the detection window.

FIG. 20 illustrates an electrode configuration 2000 of a droplet actuator of the invention. Electrode configuration 2000 is generally identical to configuration 1900 illustrated in FIG. 19, except that a detection window 2005 is provided along with an electrode path 2010 arranged to permit droplets from each path 1806 to be transported into the presence of the detection window. The detection window may be arranged on any of the electrode paths or in any location to which a droplet may be transported for detection. FIG. 20 is also illustrative of an embodiment including three temperature control elements 1810. Of course, any number of temperature control elements may be used.

In operation, when each droplet completes its predetermined number of cycles, the droplet is transported into the detection window for detection. In a similar embodiment, when each droplet completes its predetermined number of cycles, the droplet is parked. Parking involves transporting the droplet to a location and storing the droplet at the location. The location may be in a separate region of the droplet actuator relative to the thermal cycling region. Subsequently, each droplet is transported into the detection window for detection. A sensor may be arranged to detect signal from droplets located in the detection window. The sensor may be suitable for quantifying one or more signals of each droplet. The detection window need not be a physical window. In its simplest form, it is simply a region in the vicinity of a sensor in which a droplet located partially or completely in the window is susceptible to detection by the sensor.

In one example, the temperature zones are established for conducting thermal cycling of a nucleic acid amplification mix, such as a PCR mix. The amplification droplets include a nucleic acid sample along with reagents suitable for amplifying a target nucleic acid potentially present in the sample. Each path is subjected to thermal cycling for a different number of cycles. When the droplet has reached a predetermined number of cycles, the droplet may be subjected to detection, e.g., according to the various schemes described herein. For example, the droplets may be transported into the presence of a sensor for detection of amplification product.

In some cases, sets of droplets are thermal cycled sequentially, one set after another. In other cases, droplets within a set a thermal cycled sequentially and droplets outside a set are thermal cycled in parallel. Each set may include one or more droplets. The thermal cycling reactions are ended when suitable data has been collected to quantify the amplification product present in the starting sample with a predetermined acceptable degree of certainty. Thermal cycling may be stopped when it is statistically certain that the target nucleic acid is not present in the sample or is not being amplified. A new set of subsample droplets may be obtained from the sample so that the amplification reaction can be run again, e.g., using different reagents or a different droplet actuator. In other cases, if a set of thermal cycling endpoints from a set of thermal cycling droplets indicates a satisfactory curve, but shows lack of product in one or more subsample droplets that should (according to the curve) include product, new subsample droplets may be dispensed, and the thermal cycling protocol may be repeated for some or all data points.

The assay as illustrated in FIGS. 18-20 as a parallel assay, in which multiple droplets are thermal cycled in parallel. In other words, all subsample droplets in a particular group are in the same thermal zone at the same time. However, it will be appreciated that in a simpler embodiment, all or one or more subsets of the droplets may be thermal cycled sequentially. In some cases, each member of a subset is amplified following completion of amplification of a previous member of the subset, while different subsets are thermal cycled in parallel.

For example, a single-path thermal cycler may be provided. A first droplet may be thermal cycled on the path five times, then subjected to detection; a second droplet may be thermal cycled 10 times, then subjected to detection; etc. The process may be repeated until a sufficient set of data points is obtained to establish a curve from which the quantity of target nucleic acid in the sample may be calculated. Similarly, a first droplet may be thermal cycled 35 times, a second droplet 30 times, a third droplet 25 times, and so on to a first droplet which is cycled five times. Alternatively, all droplets may be parked and subjected to serial or simultaneous detection at a later time. A curve may be created from the data points, and the quantity of target nucleic in the sample may be calculated based on the curve. In one embodiment, it may be useful to conduct the lengthier cycles first, proceeding to the reduced cycle droplets only if target nucleic acid is detected in the first droplet.

In a similar embodiment, a number of thermal cycling paths may be provided which is less than the total number of droplets selected for thermal cycling. The subsample droplets may be processed in sets. Each droplet in a set may be thermal cycled generally in parallel, while the multiple sets may be thermal cycled sequentially. For example, a droplet actuator with five paths may be used to process 35 subsample droplets, 1, 2, 3 . . . 35, in sets of five. For example, a first set of five droplets might include subsample droplets for one cycle, 2 cycles, 3 cycles, 4 cycles, and 5 cycles; a second set of five droplets might process subsample droplets for 6 cycles, 7 cycles, 8 cycles, 9 cycles, and 10 cycles; and subsequent sets may process subsample droplets for 11-15 cycles, 16-20 cycles, 21-25 cycles, 26-30 cycles, etc.

In an alternative embodiment, a first set of five droplets might include subsample droplets for 5, 15, 25, 35, and 40 cycles; a second set of five droplets might include subsample droplets for 8, 10, 20, 30, and 38 samples. Other sets may fill in cycle numbers in between the numbers previously executed. Furthermore, data may be analyzed between sets, and the cycling may be terminated when sufficient data has been obtained to quantify the target nucleic acid in the sample to a predetermined range of statistical certainty. Similarly, the cycling may be terminated when it becomes clear that the target nucleic acid is not present or is not being amplified in the subsample droplets. In the latter case, the thermal cycling may be repeated, e.g., using a different droplet actuator and/or different reagents.

In parallel flow-through cycling techniques, all paths may be loaded with subsample droplets. The droplets may be moved in unison, though moving the droplets in exact unison is not required. Some droplets may be moved in opposite directions, for example. The amplification reactions in the droplets are generally stopped at different times, though it will be appreciated that some droplets may be duplicates which are cycled the same number of times and stopped simultaneously. Reactions may be stopped in a temperature control region (e.g. as illustrated in FIG. 18), or may be transported away from the temperature control regions (e.g. as illustrated in FIGS. 19 and 20). When droplets are transported across a detection zone, it may be useful to transport droplets undergoing lower cycle numbers first, followed by droplets undergoing higher cycle numbers. This approach will help to prevent or alleviate the results of cross-contamination, which may be more likely to be caused by droplets with higher concentrations of target nucleic acid.

In various embodiments of the parallel flow-through thermal cycling technique, droplets may be loaded and parked. Then thermal cycling may be started simultaneously and ended in series as each droplet for each subset of droplets finishes its predetermined number of cycles. In another embodiment, droplets may be loaded and parked, and thermal cycling for each droplet or each subset of droplets may be started in series and ended simultaneously. Protocols in which one or more subsets of droplets are started together as subsets and ended in series while other subset(s) of the droplets are started in series and complete their thermal cycling together as subset(s) are also possible within the scope of the invention. In yet another embodiment, droplets or subsets of droplets may be loaded in series and started in series as the droplets are loaded and ended as the droplets complete the thermal cycling, e.g., in series or in groups. In yet another embodiment, droplets are dispensed and loaded in parallel.

In another embodiment, droplets may begin thermal cycling simultaneously and complete different numbers of cycles simultaneously. This approach involves adjusting transport speeds and/or dwell times within thermal zones or between thermal zones so that droplets complete their different numbers of cycles simultaneously. In a similar embodiment, various subsets of droplets complete their different numbers of cycles simultaneously. For example, cycle numbers 1-5 may be completed simultaneously; cycle numbers 6-10 may be completed simultaneously; etc.

In yet another embodiment, dwell times may be different at different cycle numbers within an individual droplet's thermal cycling profile. For example, initial cycles may be slower, while later cycles may be more rapid, or vice versa. To illustrate further, a droplet may be cycled 35 times, and each cycle may be slightly faster than the preceding cycle. Or as another example, a droplet may be cycled 35 times, and cycles 1-10 may proceed at a first speed, while cycles 10-20 proceed at a second speed, etc.

In another embodiment, multiple cycles may be distributed among paths for efficient path usage. For example, in a thermal cycling droplet actuator with four available paths, droplets may be cycled as follows:

Path 1: 7
Path 2: 1, 6
Path 3: 2, 5
Path 4: 3, 4

Thus, in path 1, a single droplet is cycled seven times. In path two, a first droplet is cycled once, followed by a second droplet which is cycled six times. In path three, a first droplet is cycled two times in the second droplet is cycled five times. Finally, in path four, a first droplet is cycled three times, in the second droplet is cycled four times. Each path conducts exactly 7 cycles, making efficient usage of the path space and minimizing the total time required to cycle all of the droplets. Further, in the illustration, droplets undergoing lower cycle numbers are processed first, followed by droplets undergoing higher cycle numbers. In this manner, droplets with lower numbers of copies precede droplets of higher number of copies on the same droplet actuator real estate. This approach reduces the possibility of cross-contamination caused by residue left behind by the first droplets. Of course, this is a simple example, and any number of paths may be used with any number of droplets and combined similarly, as will be appreciated by those of skill in the art in light of the present specification.

7.3 Meandering Flow Through

Figure 21:
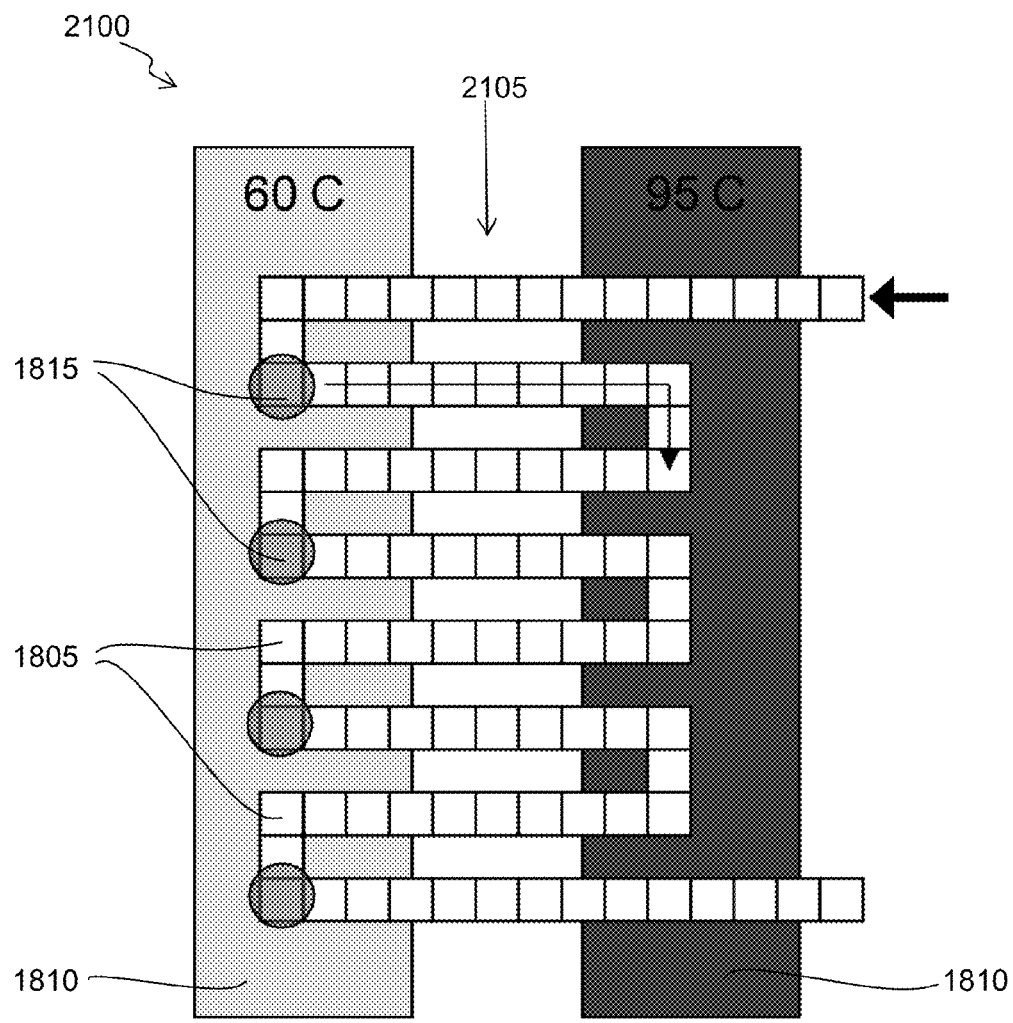
FIG. 21 illustrates an electrode configuration of a droplet actuator of the invention including a meandering electrode path that snakes through two or more thermal zones.

FIG. 21 illustrates electrode configuration 2100 of a droplet actuator of the invention. Electrode configuration 2100 includes electrode path 2105 including electrodes 1805 configured in a manner which permits droplets 1815 from a source (not shown) to be transported along the electrode paths back and forth between two or more temperature zones. As with previous examples, the temperature zones are established by temperature control elements 1810, such as heaters or heat sinks. Droplets 1815 are snaked along meandering or winding electrode path 2105 back and forth between temperature zones established by temperature control elements 1810. As with other embodiments, the droplet actuator may be provided as part of the system which controls the droplet operations. The system may be programmed to transport droplets through the thermal cycling region and into position for detection.

Figure 22:
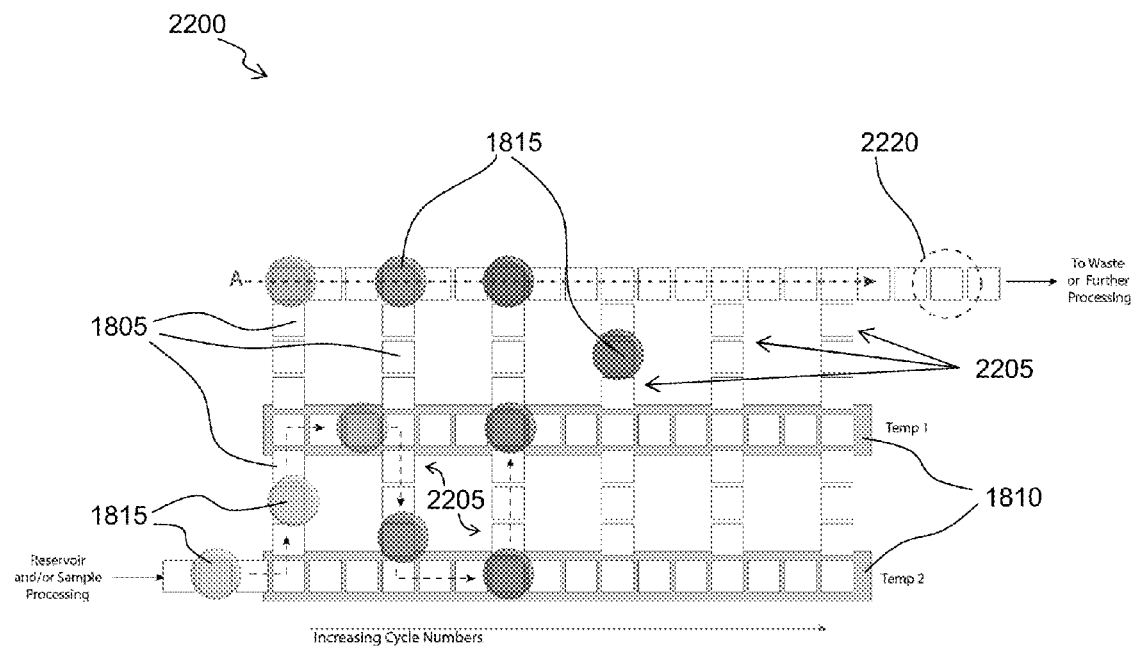
FIG. 22 illustrates an electrode configuration of a droplet actuator of the invention including a meandering electrode path that snakes through two or more thermal zones with additional electrode paths configured for transporting droplets off of the meandering electrode path.

FIG. 22 illustrates electrode configuration 2200 of a droplet actuator of the invention. Electrode configuration 2200 is similar to electrode configuration 2100 of FIG. 21. However, electrode configuration 2200 includes electrode paths 2205 for transporting droplets away from the thermal cycling zone for detection. Electrode paths 2205 are configured for transporting droplets off of the meandering electrode path 2005.

Each droplet may be cycled through temperature zones for predetermined number of cycles, and then transported away for detection. Droplets may be parked, and then scanned by a sensor. For example, droplets may be parked along the line A, and a sensor may scan the droplets. Alternatively, droplets may be transported into a detection window 2220 for detection. A sensor may be arranged to detect droplets positioned in the detection window. The sensor may be suitable for detecting signal from each droplet. In another embodiment, an array detector, such as a CCD camera or an array of LED-Photodiode pairs, may be used to detect multiple droplets simultaneously.

Thus, in one example, droplets 1815 including a nucleic acid amplification mix, such as PCR mix, and a sample potentially including a target nucleic acid may be dispensed and transported along meandering path 2205 established by electrodes 1805. Droplets 1815 may be thermal cycled by transporting droplets droplet 1815 along meandering path 2205, which passes back and forth between temperature zones established by temperature control elements 1810.

Each droplet may be cycled a predetermined number of times, and as each droplet completes its predetermined number of cycles, it may be transported away from the thermal cycling temperature zones for detection. In another embodiment, as each droplet completes its predetermined number of cycles, it may be transported into one of the thermal cycling temperature zones or into another thermal cycling temperature zone having a temperature suitable for maintaining the droplets for detection. In various embodiments, the droplets may be parked and scanned by a sensor. In another embodiment, each droplet may be transported into a detection window. The process produces a set of droplets, each of which has been thermal cycled a predetermined number of times. For example, a first droplet may be thermal cycled five times, a second droplet may be thermal cycled 10 times, a fourth droplet may be thermal cycled 15 times, etc. As with other examples, the process may be stopped when suitable data have been obtained to quantify the target substance.

The meandering path may take any of a variety of shapes which essentially meander or snake back and forth or zigzag between temperature zones. For example, the electrode path may snake back and forth along right angles as illustrated in FIGS. 4 and 6. The path may form a part of a larger array of electrodes from which a meandering or snaking path may be selected. The meandering path may take a zigzag shape or a curvilinear shape. Each turn in the meandering path may be generally the same, or the turns may be differently sized.

Droplets may be continually fed into the meandering path at one end of the path and may pass through to the opposite end. In some embodiments, electrode paths may be arranged to conduct droplets onto or off of the meandering path. For example, in one embodiment every meander or turn of the path includes at least one access electrode path for removing droplets from and/or introducing droplets to the path. In some cases, droplets may be supplied into the path at different points along the path via an access electrode path. In some cases, droplets may be removed from the path at different points along the path via an access electrode path. In other embodiments, droplets may be introduced onto and/or removed from the path via an opening in any droplet actuator substrate, such as the top substrate, the bottom substrate, and/or a lateral opening into the droplet operations gap between the top and bottom substrates.

In some embodiments, it may be useful to synchronize the reactions. In such embodiments, droplets may be supplied at a rate equal to the transport cycle time. In this embodiment, the number of reactions in progress increases by one at each transport cycle. In this embodiment, synchronization means that all droplets are in the same part of the thermal cycle at the same time. Synchronization of droplets enables the transport rate to be variable. Droplets may be stopped and incubated in the same part of the thermal cycle at the same time.

In various embodiments, it may be useful to ensure that no droplet traverses an electrode which was previously occupied by a higher cycle number droplet, i.e., a droplet that may be expected to have a higher concentration of target nucleic acid.

In some embodiments, detection of droplets occurs in place on the meandering path. In other embodiments, droplets are transported elsewhere for detection. In some embodiments, it may be useful to transport the droplets along the meandering path to a point of detection. In such embodiments, once thermal cycling of all droplets is complete, the temperature control elements may be adjusted to permit for the transport of droplets along the meandering electrode path without continued thermal cycling. For example, the nucleic acid denaturation heater may have its temperature reduced to a point below the lowest possible nucleic acid denaturation temperature. In this manner, the droplets may continue to be snaked along the meandering path without continuing the amplification process. If carryover is a concern, it may be useful to reverse the direction of droplet flow, i.e. removing the droplets having lower cycle numbers first, followed by droplets having higher cycle numbers. In this manner, no droplet will pass over an electrode which has previously hosted a higher cycle number droplet.

In another embodiment, the reactions may be inactivated so that they can continue to be transported through the thermal cycling temperatures without amplification. Alternatively, as described above, the droplets may be transported via access electrode paths to another location on the droplet actuator for detection.

Figure 23:
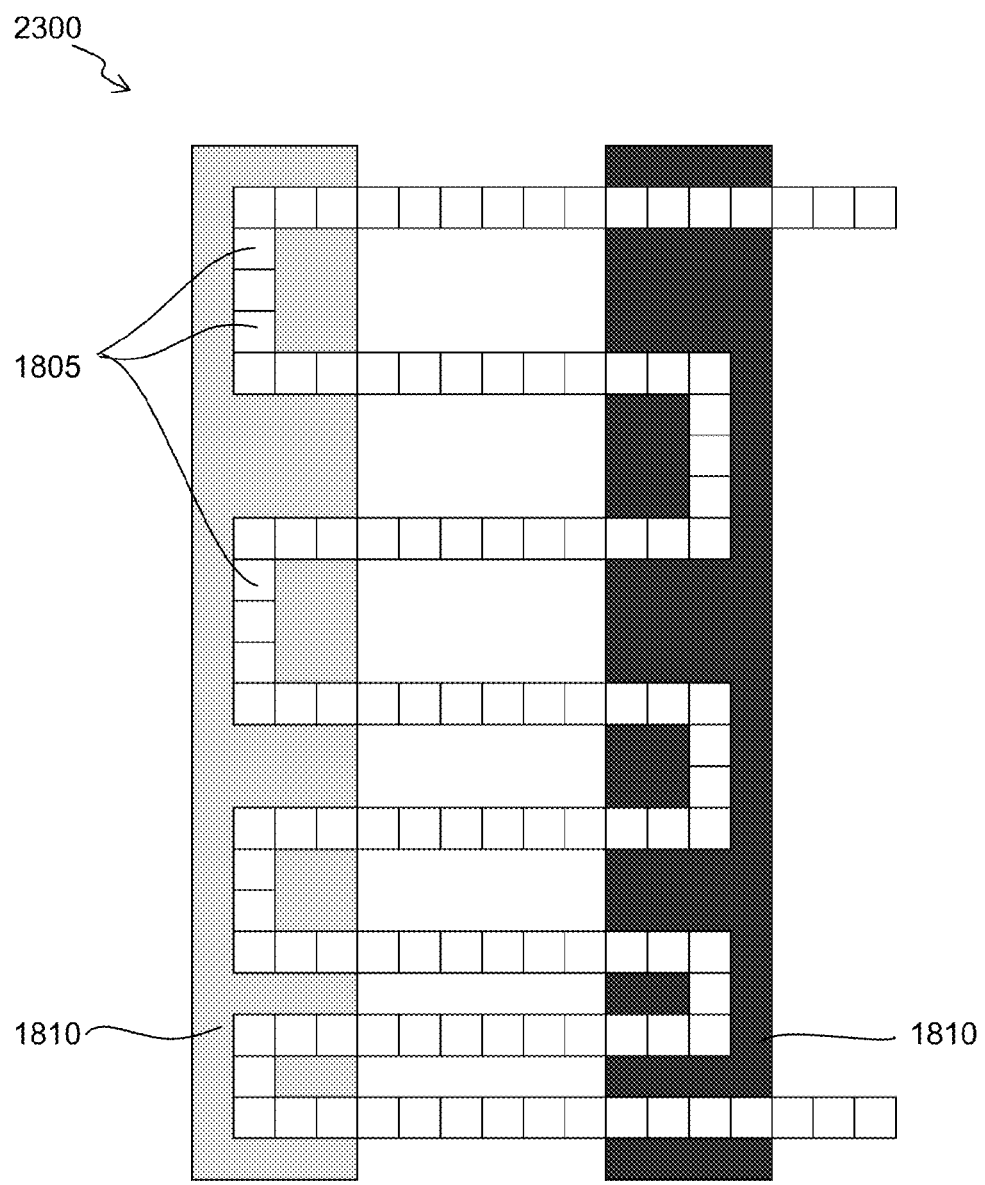
FIG. 23 illustrates an electrode configuration of a droplet actuator of the invention, showing how the meandering electrode path within each thermal zone may be lengthened or shortened in order to lengthen or shorten the residence time of the droplet in that zone.

FIG. 23 illustrates an electrode configuration 2300 of a droplet actuator of the invention. Electrode configuration 2300 illustrates how the meandering electrode path within each thermal zone established by temperature control elements 1810 may be lengthened or shortened in order to lengthen or shorten the residence time of the droplet in that zone.

For example, in one embodiment, the length of the turns of the meandering paths in the thermal zones (i.e., number of electrodes in the thermal zones) may become progressively smaller in the direction of the droplet's progression so that the cycles will speed up as the droplet is transported along the path at a constant rate from electrode to electrode. Similarly, the length of the turns of the meandering paths in the thermal zones (i.e., number of electrodes in the thermal zones) may become progressively larger in the direction of the droplet's progression, so that the cycles will slow down as the droplet is transported along the path at a constant rate from electrode to electrode. In another embodiment, the length of the turns of the meandering paths in the thermal zone (i.e., number of electrodes in the thermal zones) may vary to provide longer incubation times at specific cycle numbers, such as the first cycle.

Thus, droplets may be continually fed into a pathway that meanders between the two temperature zones and be transported at a fixed and uniform rate. Residence time in the temperature zones may be determined by the number of electrodes of the droplet must traverse to pass through the temperature zone. In this embodiment, droplets may not be thermally synchronized in the sense that different droplets may be in different phases of the temperature cycle at the same time. This embodiment may be useful for reducing the size of the droplet actuator by arranging the electrodes on the droplet actuator in a manner which takes up less real estate.

It should also be noted that the meandering electrode configuration or other flow-through configurations described herein, while generally illustrated as having two temperature zones may have any number of temperature zones.

Figure 24:
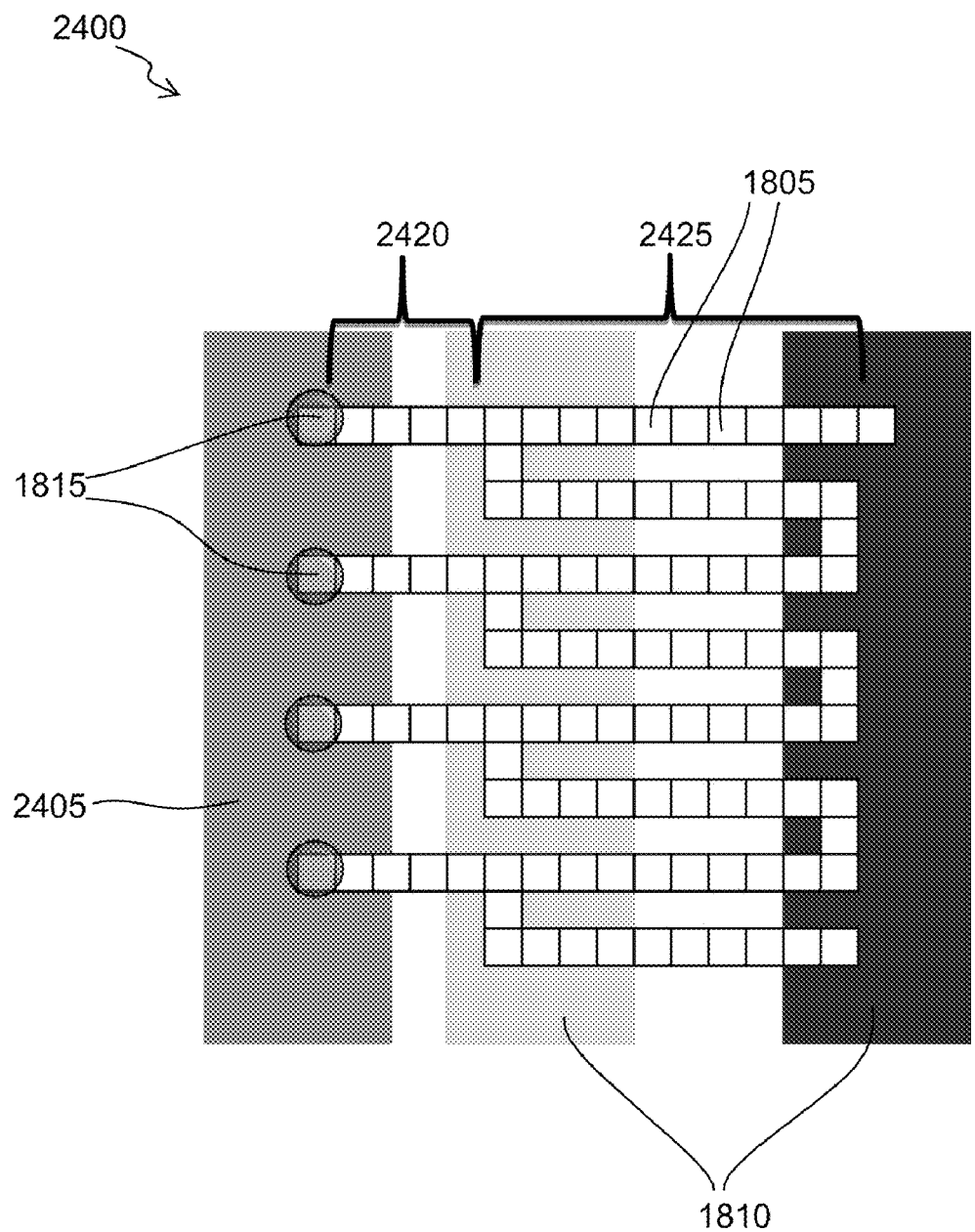
FIG. 24 illustrates an electrode configuration of a droplet actuator of the invention including a meandering path, wherein one or more of the turns of meandering path is associated with an access path.

FIG. 24 illustrates an electrode configuration 2400 of a droplet actuator of the invention. Electrode configuration 2400 illustrates an embodiment including meandering path 2425, wherein one or more of the turns of meandering path 2425 includes an access path 2420. In the embodiment illustrated, access paths 2420 are configured for transporting droplets from meandering path 2425 into a temperature control zone established by temperature control element 2405. Temperature control element 2405 may, for example, be configured to maintain the amplified droplets prior to detection. For example, the droplets may be maintained at room temperature or a temperature selected to preserve droplet components prior to detection. Thus, in operation, a series of droplets may be transported a long meandering path 2425 to transport the droplets between thermal zones 1810. With respect to each droplet, when a predetermined number of cycles has been accomplished, the droplet may be transported off of meandering path 2425 via access path 2420 and transported for detection or into a storage zone for holding pending detection.

Figure 25:
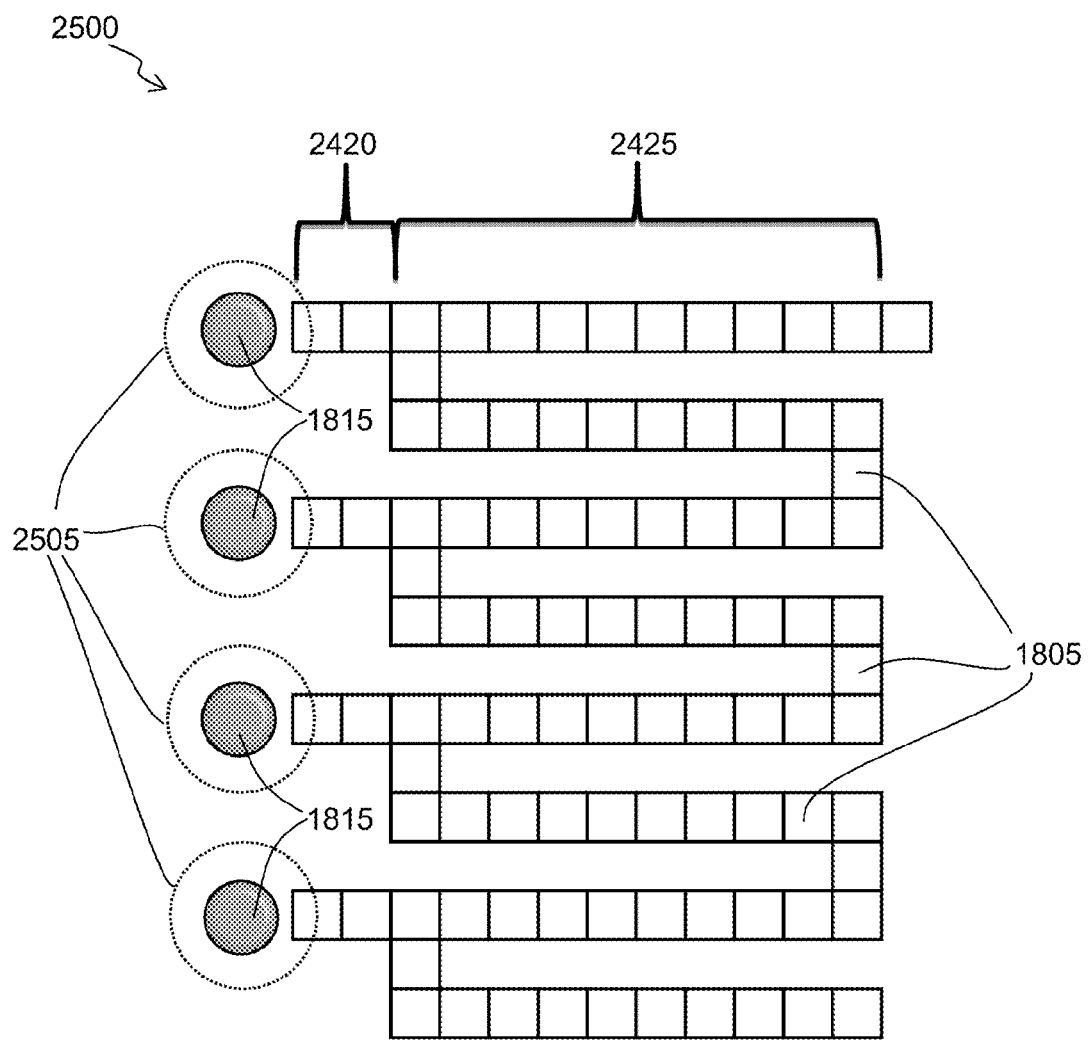
FIG. 25 illustrates an electrode configuration like the electrode configuration of FIG. 25, but also including droplet parking zones for storing droplets prior to detection without requiring electrode activation.

FIG. 25 illustrates an electrode configuration 2500 of a droplet actuator of the invention. Electrode configuration 2500 is like electrode configuration 2400 of FIG. 24, except that configuration 2500 includes parking zones 2505 for storing droplets prior to detection without requiring electrode activation. Parking zones 2505 may, for example be established by a variety of chemical and/or physical features. For example, parking zones 2505 may be established by physical features within the droplet operations gap or on the top substrate or bottom substrate (e.g., barriers, wells, indentations and/or protrusions), as well as chemical features, such as hydrophilic regions. The physical and/or chemical features may cooperate to retain droplets 1815 in place during and/or pending detection. Thus, in operation, a series of droplets may be transported a long meandering path 2425 to transport the droplets between thermal zones (not illustrated). With respect to each droplet 1815, when a predetermined number of cycles has been accomplished, the droplet 1815 may be transported off of meandering path 2425 via access path 2420 and transported into a parking zone 2505 for holding pending detection.

7.4 Loop Flow-Through

Figure 26:
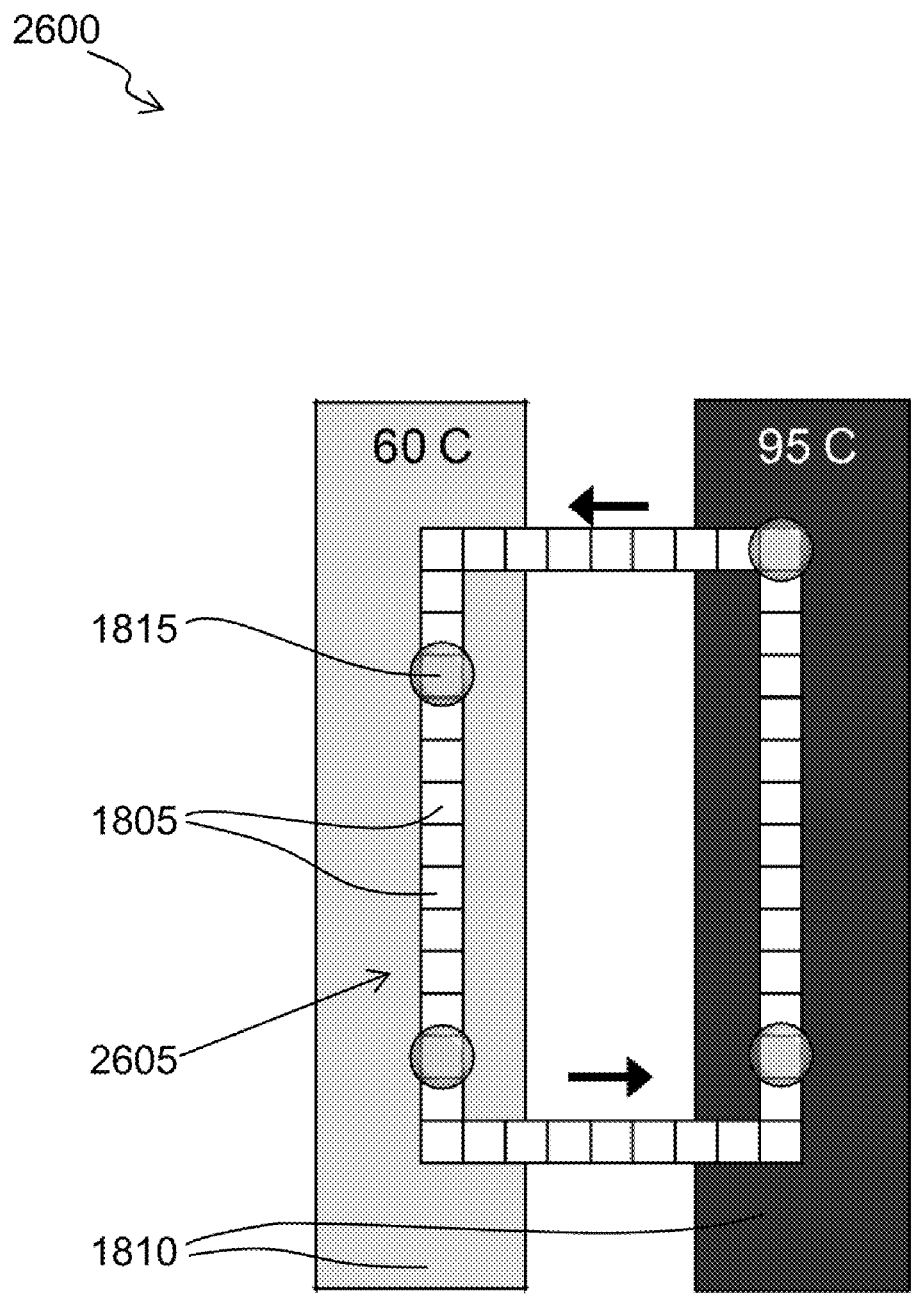
FIG. 26 illustrates an electrode configuration of a droplet actuator of the invention including electrodes arranged to form an electrode path loop for transporting droplets between thermal control zones.

FIG. 26 illustrates an electrode configuration 2600 of a droplet actuator of the invention. Electrode configuration 2600 includes electrodes 1805 arranged to form an electrode loop 2605. Droplets 1815 are transported along an electrode path in a loop through thermal zones to effect thermal cycling. Droplets may enter the loop, pass around the loop a predetermined number of times, and then exit the loop. Entrance and exit may, for example, be provided by access electrode paths (not shown) and/or through one or more openings from an exterior of the droplet actuator (e.g., through a top or bottom substrate or any other route into the droplet actuator).

Transport may be constant, i.e. droplets continually move around the loop at a constant rate or droplets may move at different rates but at a substantially identical average rate. For constant transport embodiments, the electrode layout may be configured to establish the requisite residence time in each thermal zone. Transport may be periodic, i.e., droplets may be retained in a thermal zone for a period of time, then transported to the other thermal zone via the loop.

Loops can efficiently accommodate a range of droplets, and where necessary can be loaded with the maximum number of droplets for some portion of a thermal cycling protocol or for the entire protocol. Transport of droplets around a loop may be unidirectional or may be bidirectional (i.e., droplet transport direction may be reversible). Detection may be accomplished on the loop itself, or droplets may be transported away from the loop for detection. Constant circulation may increase mixing and thermal uniformity within the droplet, and circulating each droplet through the same path may reduce variability due to spatial temperature variations within the thermal zone.

Figure 27:
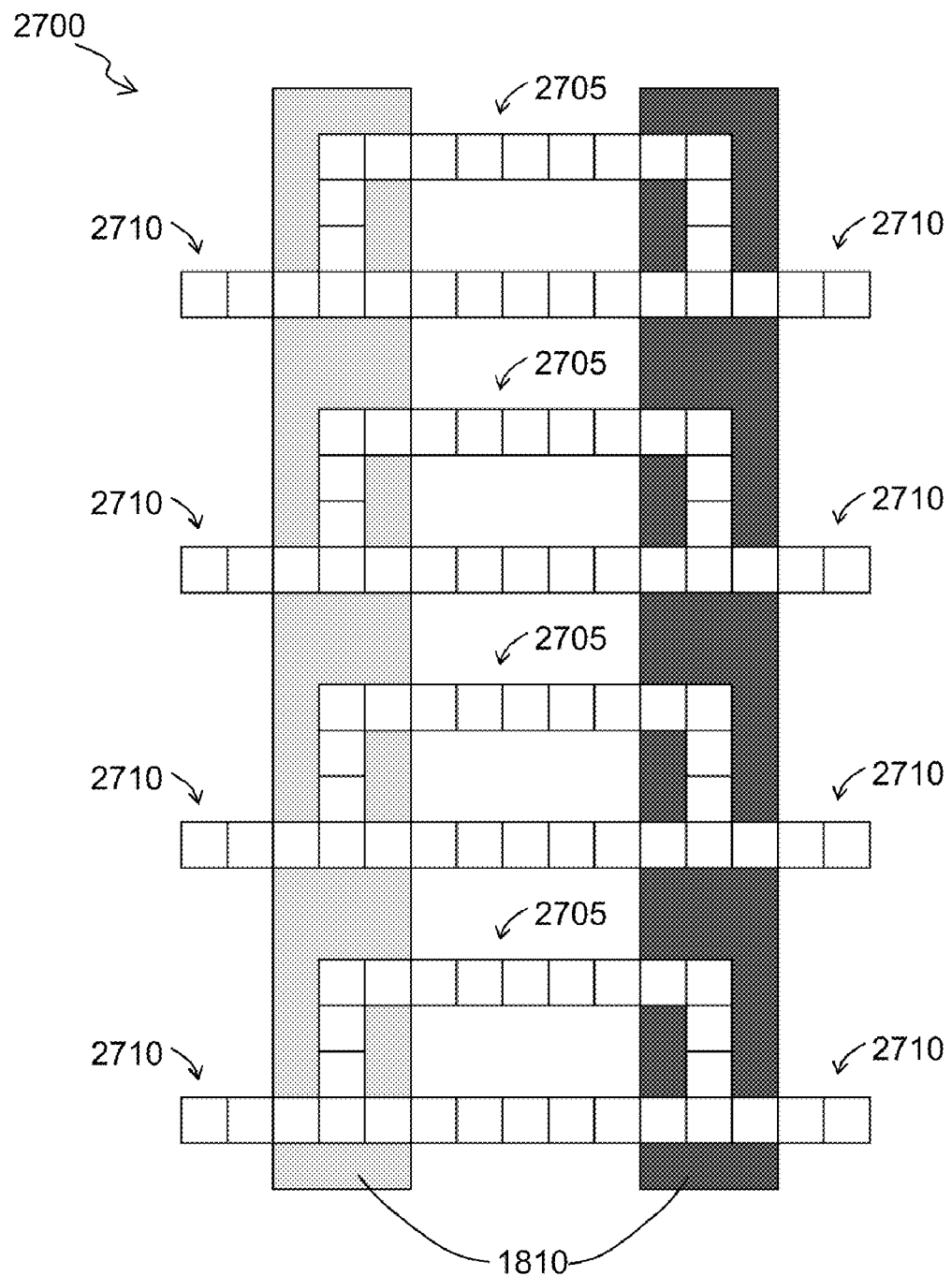
FIG. 27 illustrates an electrode configuration of a droplet actuator of the invention including multiple electrode path loops.

FIG. 27 illustrates an electrode configuration 2700 of a droplet actuator of the invention. Electrode configuration 2700 includes multiple electrode path loops 2705. Electrode configuration 2700 also includes access electrode paths 2710 for transporting droplets onto and/or off of electrode path loops 2705. A thermal cycling protocol may involve one or more of loops 2705. For example, a series of four loops 2705 may be used to conduct a thermal cycling protocol in which multiple droplets are cycled on each loop. Generally speaking, droplets should be separated by 1 or 2 empty electrode positions on the loops, so the maximum number of droplets on each loop is equal to ½ n or ⅓ n, where n is the total number of electrodes in the loop, where n is the number of electrodes in the loop. Detection may be real time or endpoint data from each of the cycles may be used to establish a curve used to quantify product in the sample.

Figure 28:
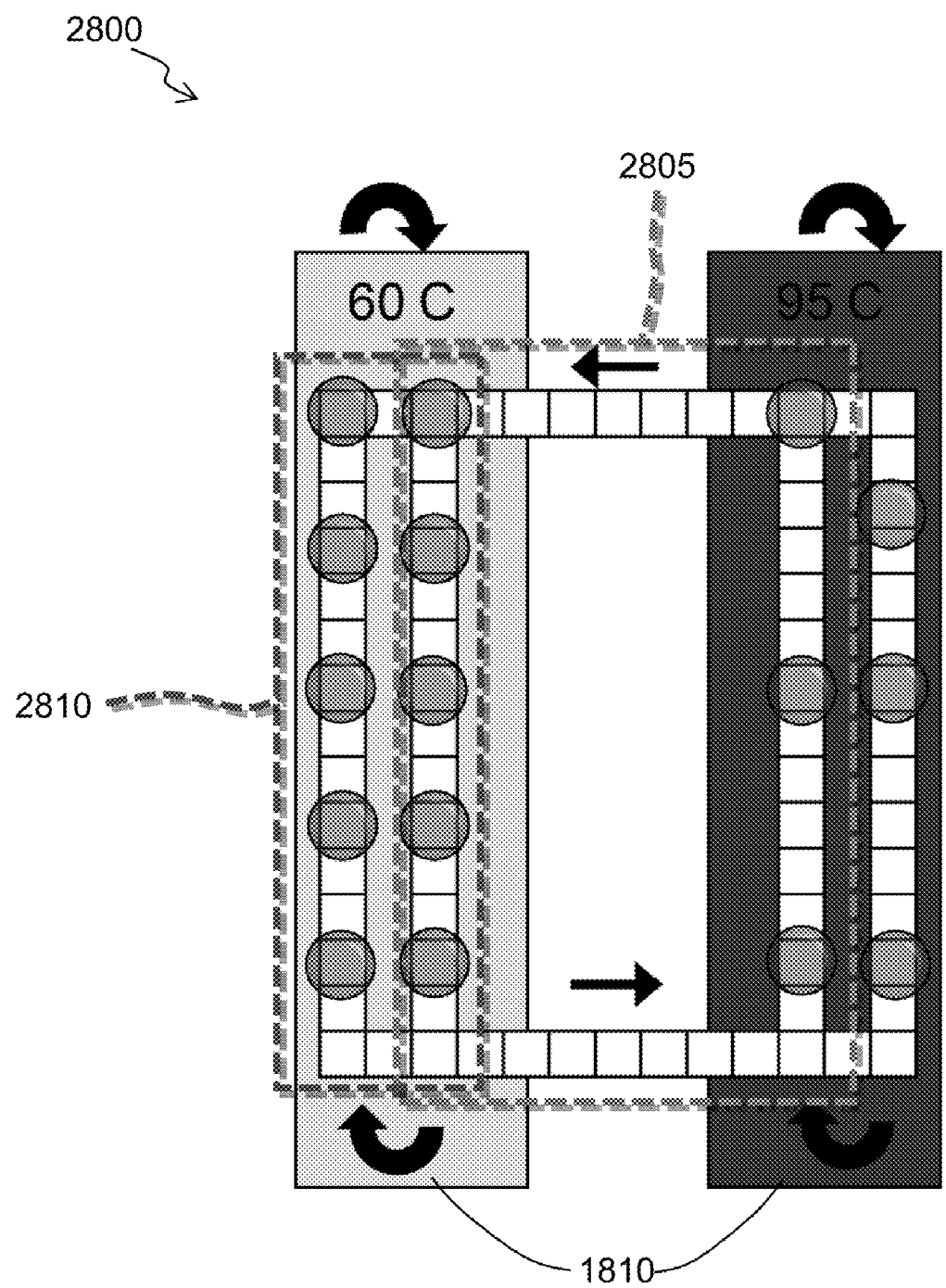
FIG. 28 illustrates an electrode configuration of a droplet actuator of the invention including an electrode path loop and electrode paths sub-loops.

FIG. 28 illustrates an electrode configuration 2800 of a droplet actuator of the invention. Electric configuration 2800 includes an electrode path loop 2805, and electrode paths sub-loops 2810. Electrode path sub-loops 2810 are configured to provide a holding area for droplets in the thermal zones. In configuration 2810 and similar configurations, protocols can be executed in which one or more droplets needs to be maintained in a thermal zone for a period of time which is longer than the effective residence time based solely on the transport rate. It will be appreciated that electrode paths of loops 2810 may be replaced with branching structures or other kinds of loops.

Where a loop is present, storage may be accomplished by rotating droplets around a sub-loop 2810 until a specific droplet is accessed. The specific droplet may then be transported via electrode path loop 2805 to the other thermal zone. In the other thermal zone, the specific droplet may be stored on the loop or passed through the loop and directed back to the starting thermal zone. Movement around electrode path loop 2805 and around electrode path sub-loops 2810 may be unidirectional or may be bidirectional. It will also be appreciated that other embodiments with linear electrode paths, such as those illustrated in FIGS. 18-20, may also include looping electrode paths or branching electrode paths within the thermal zones.

7.5 Aliquoting Flow-Through Cycle

Figure 29:
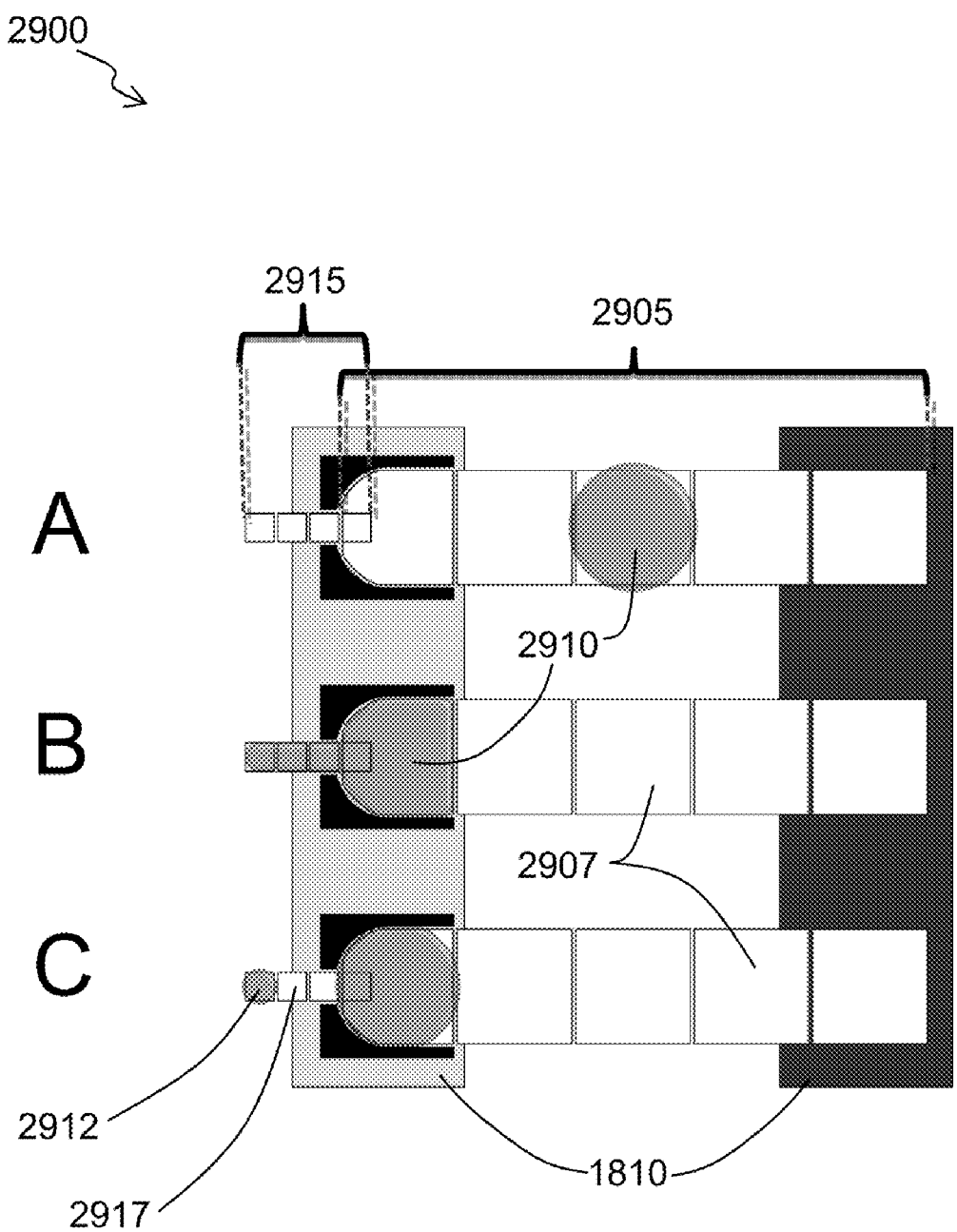
FIG. 29 illustrates an electrode configuration of a droplet actuator of the invention illustrative of a flow-through thermal cycling configuration in which sub-droplets are split off from a larger droplet for detection.

FIG. 29 illustrates an electrode configuration 2900 of a droplet actuator of the invention. Electrode configuration 2900 illustrates a flow-through thermal cycling configuration in which sub-droplets are split off from a larger droplet for detection. Electrode configuration 2900 includes a first electrode path 2905 including electrodes 2907 configured for transporting a thermal cycling droplet 2910 back-and-forth between thermal zones established by thermal control elements 110. It will be appreciated that electrode path 2905 may be replaced with one or more electrode path loops and/or meandering flow-through electrode arrangements, such as those described herein. Electrode configuration 2900 also includes a second electrode path 2915 including electrodes 2917 configured for dispensing a sub-droplet 2912 from thermal cycling droplet 2910. Electrodes 2907 are generally larger than electrodes 2917, and therefore support relatively larger volume droplets 2910, from which may be dispensed multiple smaller volume sub-droplets 2912. Electrode path A illustrates droplet 2910 during thermal cycling being transported between thermal zones established by thermal control elements 1810. Electrode path B illustrates part of a dispensing operation in which droplet 2910 is positioned on an electrode of electrode path 2905 in proximity to electrode path 2915. Electrodes 2917 on electrode path 2915 are activated, thereby causing the formation of an elongated extension out of droplet 2910. Electrode path C illustrates the deactivation of one or more intermediate electrodes 2917 to cause formation of sub-droplet 2912 on electrode path 2915. Sub-droplet 2912 may be subjected to detection where it is formed and/or it may be transported away for detection.

Generally speaking, in an aliquoting flow-through approach, the thermal cycling droplet 2910 size is several times the size of the sub-droplets 2912 that are removed for detection. In some embodiments, a new droplet may be added to the thermal cycling droplet following removal of a sub-droplet for detection. The added droplet may, for example, include buffer or one or more additional reagents for the thermal cycling reaction. In this manner, the thermal cycling droplet may be maintained at a constant volume. In the embodiment illustrated in FIG. 29, electrodes 2917 used to dispense off a sub-droplet from the thermal cycling droplet 2910 are smaller than the thermal cycling electrodes 2907 in order to accommodate smaller sub-droplets 2912. However, in an alternative configuration, droplets used to dispense off sub-droplets may be the same size as droplets used to transport thermal cycling droplets. In some cases, the thermal cycling droplets may be transported as elongated slug-shaped droplets, and the sub-droplets may be dispensed off the end of the slug shaped droplets, e.g., by deactivating an intermediate electrode underlying the slug.

In a related approach, a set of sample droplets is thermally cycled, and a sub-droplet is removed from one member of the set following each cycle. In this approach, if there are n sample droplets in the set, then a sub-droplet may be removed from a droplet every n cycles. This approach has the advantage that it supports a thermal cycling protocol using a smaller range of droplet sizes. For example, 10 parallel reactions of 4× droplets may be used to provide 40 thermal cycling endpoints.

In another related embodiment, a larger droplet may be thermal cycled several times, prior to being divided off into smaller droplets, which may be thermal cycled as described above. This approach may be useful in any of the embodiments described herein which involve thermal cycling of multiple sub-droplets. In this manner, an initial concentration of product (e.g., nucleic acid product) can be established, so that each sub-droplet will include sufficient product to ensure amplification in the sub-droplet. Thus, the invention includes various embodiments in which multiple pads of electrodes are associated with each other in a manner similar to the association of electrode path 2905 and 2915 illustrated in FIG. 29. For example, in one embodiment, three electrode paths are included, a first pass having large electrodes, a second path had the intermediate sized electrodes, and a third pass having small sized electrodes. As another example, a layout may include a first electrode path having large sized electrodes. This first electrode path may be associated with two or more second electrode paths having smaller sized electrodes. Each of the second electrode paths may be associated with one or more third electrode paths having still smaller sized electrodes. A first, large droplet may be thermal cycled on the first electrode path, and then dispensed onto the two or more second electrode paths. From the two or more second electrode paths a droplet may be dispensed onto one or more of the third electrode paths for detection. The droplets on the second electrode paths may be thermal cycled, and following each predetermined number of thermal cycles, sub-droplets may be dispensed onto the one or more third electrode paths for detection.

7.6 Batch Cycling

In one embodiment, the invention provides a serial detection batch thermal cycling technique. In this approach, subsample droplets may be generated from a sample and arrayed in a temperature control zone. A temperature control element may cycle temperatures in the temperature control zone according to a predetermined thermal cycling protocol. One droplet may be detected after every predetermined number of cycles. Thus, for example, in one embodiment a different droplet is detected after each cycle. In this manner, each droplet is subjected to detection only once. The data may be used to generate a curve suitable for quantifying the target substance present in the sample.

Figure 30:
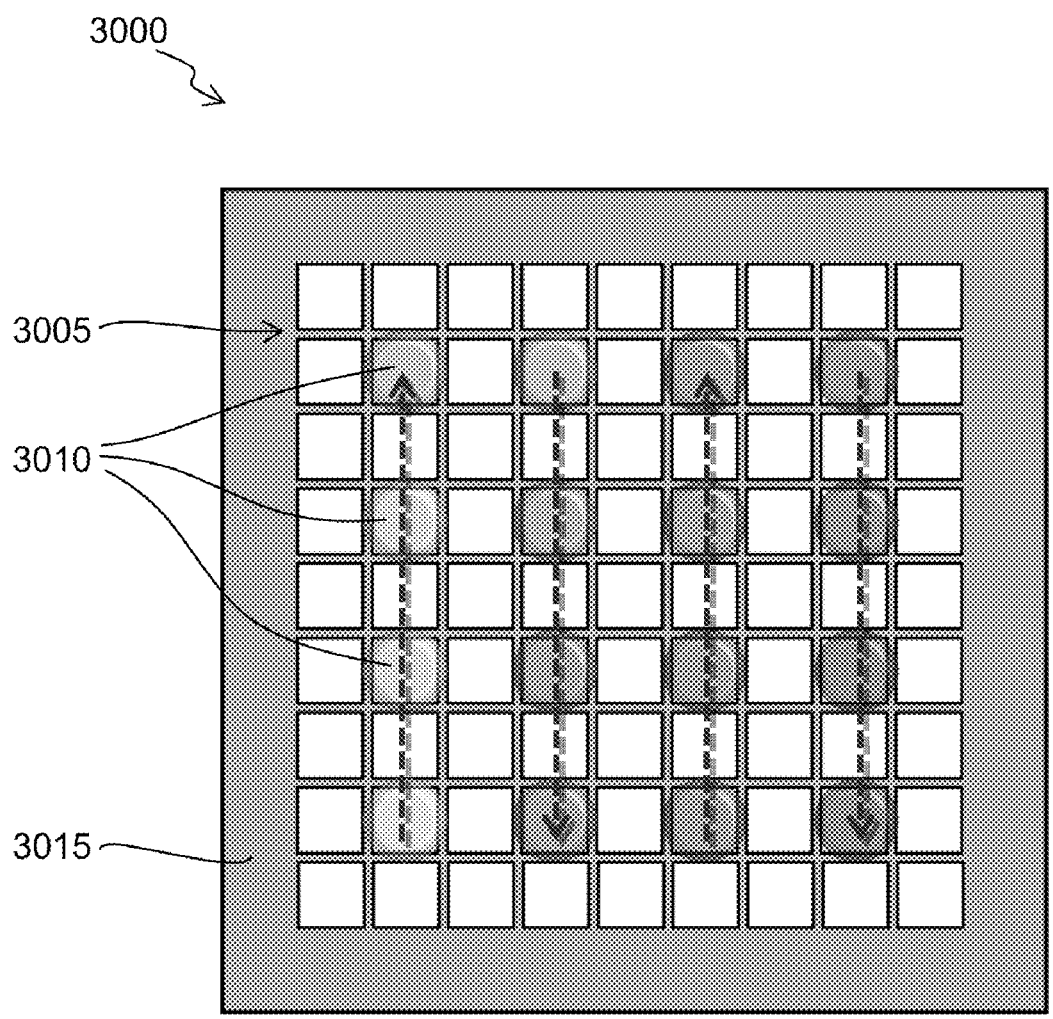
FIG. 30 illustrates an electrode configuration of a droplet actuator of the invention including an electrode array and subsample droplets arrayed upon electrode array.

FIG. 30 illustrates an electrode configuration 3000 of a droplet actuator of the invention. Droplet actuator 3000 includes an electrode array 3005 and subsample droplets 3010 arrayed upon electrode array 3005. Subsample droplets 3010 may be dispensed from a single sample droplet (not shown). Subsample droplets 3010 may be loaded onto electrode array 3005 via an electrode path (not shown) or via one of more openings (not shown) to an exterior of a droplet operations gap (when present).

One or more thermal cycling temperature control elements 3015 is associated with array 3005, e.g., underlies and/or overlies the array. Thermal cycling temperature control element 3015 is heated and actively or passively cooled to thermal cycle droplets 3010 on electrode array 3005. During thermal cycling, a sensor is passed over droplets 3010 to detect signal from droplets 3010. For example, a sensor may be passed over droplets 3010 at a rate sufficient to detect a single droplet following each cycle. Generally speaking, a sensor may be passed over droplets 3010 at a rate sufficient to detect a single droplet every n cycles, where n is the number selected to achieve sufficient endpoints to generate a curve useful for quantifying target product in the droplets at a predetermined level of statistical significance. In an alternative embodiment, two or more sensors may be used. In yet another embodiment, an array detector, such as a CCD camera or an array of LED-Photodiode pairs, may be used to detect multiple droplets simultaneously.

In a similar embodiment, subsample droplets may be generated from a sample in arrayed in a temperature control zone. A temperature control element may cycle temperatures in the temperature control zone according to a predetermined thermal cycling protocol. Following each n rounds of thermal cycling, one or more droplets may be transported away from the temperature control zone for detection. For example, the transport may be conducted by droplet operations along an electrode path. Droplets may be detected as they leave the temperature control zone, or they may be parked for analysis at a later time.

In a related approach, droplets may be sequentially transported onto a thermal cycling unit one or more at a time every n thermal cycles. Then, detection can be conducted following the final cycle. For example, the array of droplets may be imaged sequentially, simultaneously or in subsets following the final cycle, and data from the detection may be used to generate a curve for quantifying target product in the original sample.

Figure 31:
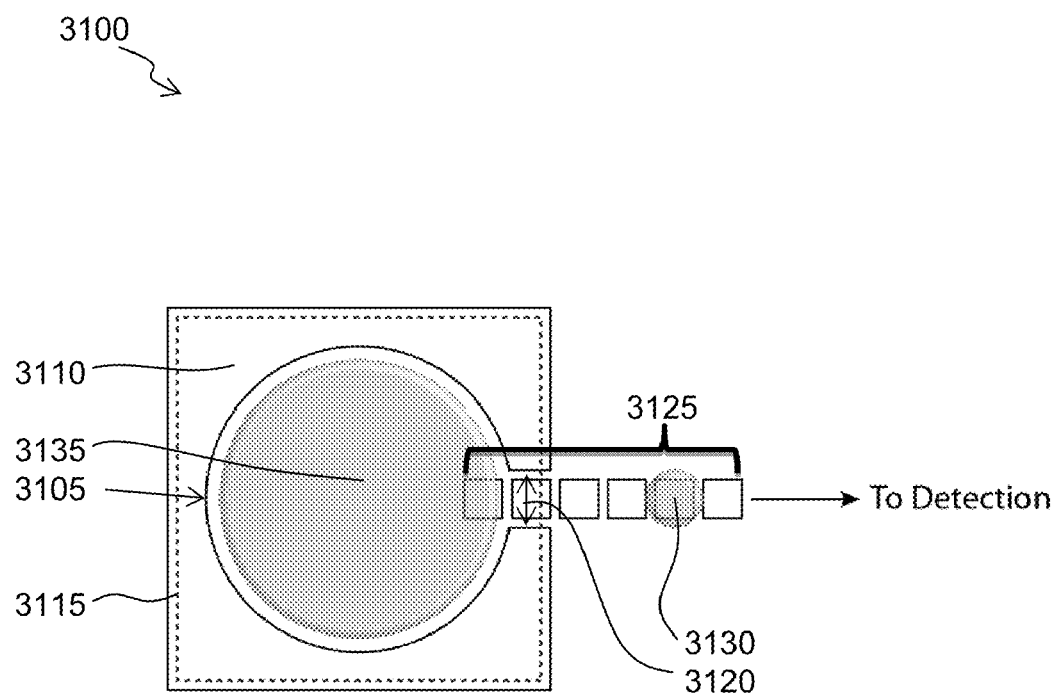
FIG. 31 illustrates an embodiment of the invention in which a sample droplet is thermal cycled, and following every n cycles, a subsample droplet is dispensed and transported away for detection.

FIG. 31 illustrates another of electrode configuration 3100 of the invention in which a sample droplet is thermal cycled, and following every n cycles, a subsample droplet is dispensed and transported away for detection. In the embodiment illustrated, a reservoir 3105 is established by a gasket 3110. A temperature control element 3115 underlies reservoir 3105. An opening 3120 in gasket 3110 provides a liquid path for transporting subsample droplets 3130 away from reservoir 3105. An electrode path 3125 provides a means for dispensing subsample droplets 3130 from sample droplet 3135. Dispensed subsample droplets 3130 may be subjected to detection. For example, they may be subjected to detection right away upon formation, or they may be transported away for detection at a later time.

In a similar embodiment, droplet 3135 may be provided in a reservoir exterior to the droplet operations gap of a droplet actuator. Droplet 3135 may be thermal cycled in the reservoir, and sub-droplets 3130 may be dispensed from the reservoir into the droplet operations gap using any of a variety of droplet dispensing techniques. For example the reservoir may be associated with a liquid path extending from the reservoir into the droplet operations gap into proximity with one or more electrodes. The electrodes may be used to dispense droplets into the droplet operations gap following each n cycles of thermal cycling. The dispensed droplets may then be subject to further assay steps and/or detection.

Figure 32:
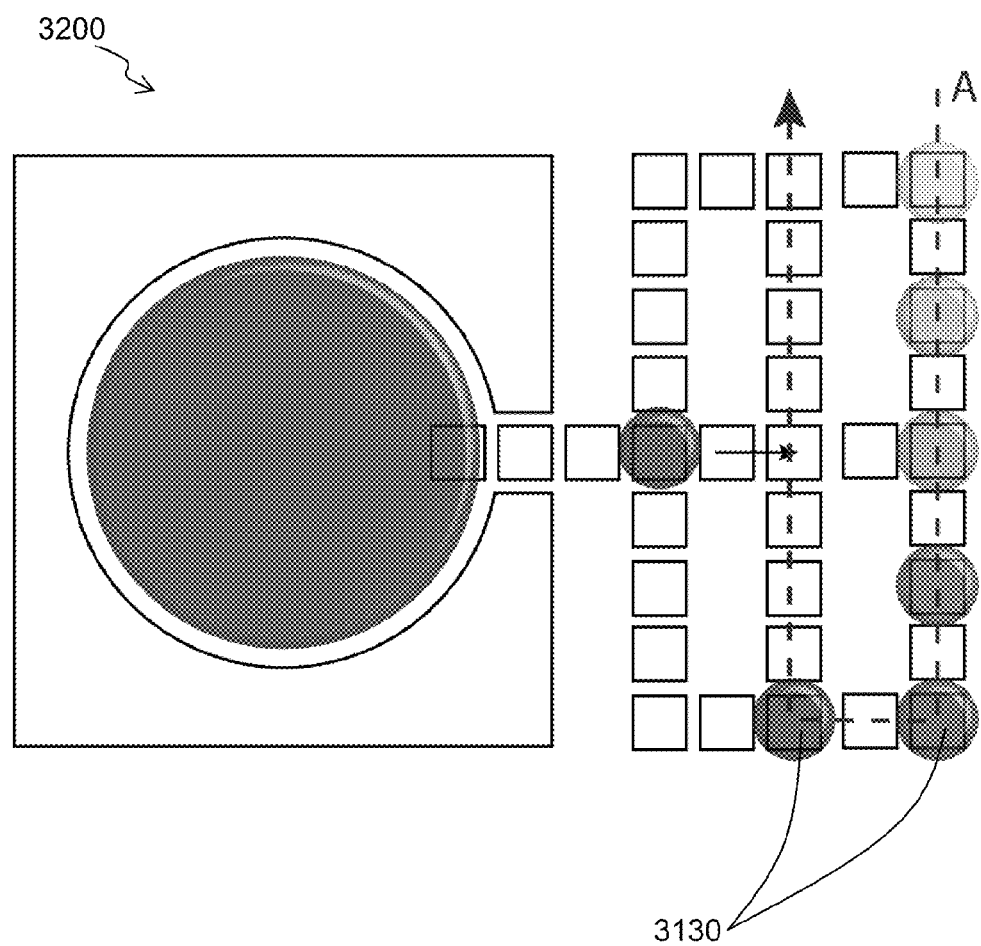
FIG. 32 illustrates an embodiment that shows how sub-droplets may be transported away and arrayed, followed by scanning by a detector.

FIG. 32 illustrates an embodiment that is similar to electrode configuration 3100 of FIG. 31. Electrode configuration 3200 illustrates how sub-droplets 3130 may be transported away and arrayed, followed by scanning by a detector. For example, the detector may detect each droplet sequentially along a path, such as the path marked A. Alternatively, in this and other embodiments described herein, all droplets may be imaged together, using an array detector, such as a CCD camera or an array of LED-Photodiode pairs, for example.

7.7 Reaction Quenching Techniques

Figure 33:
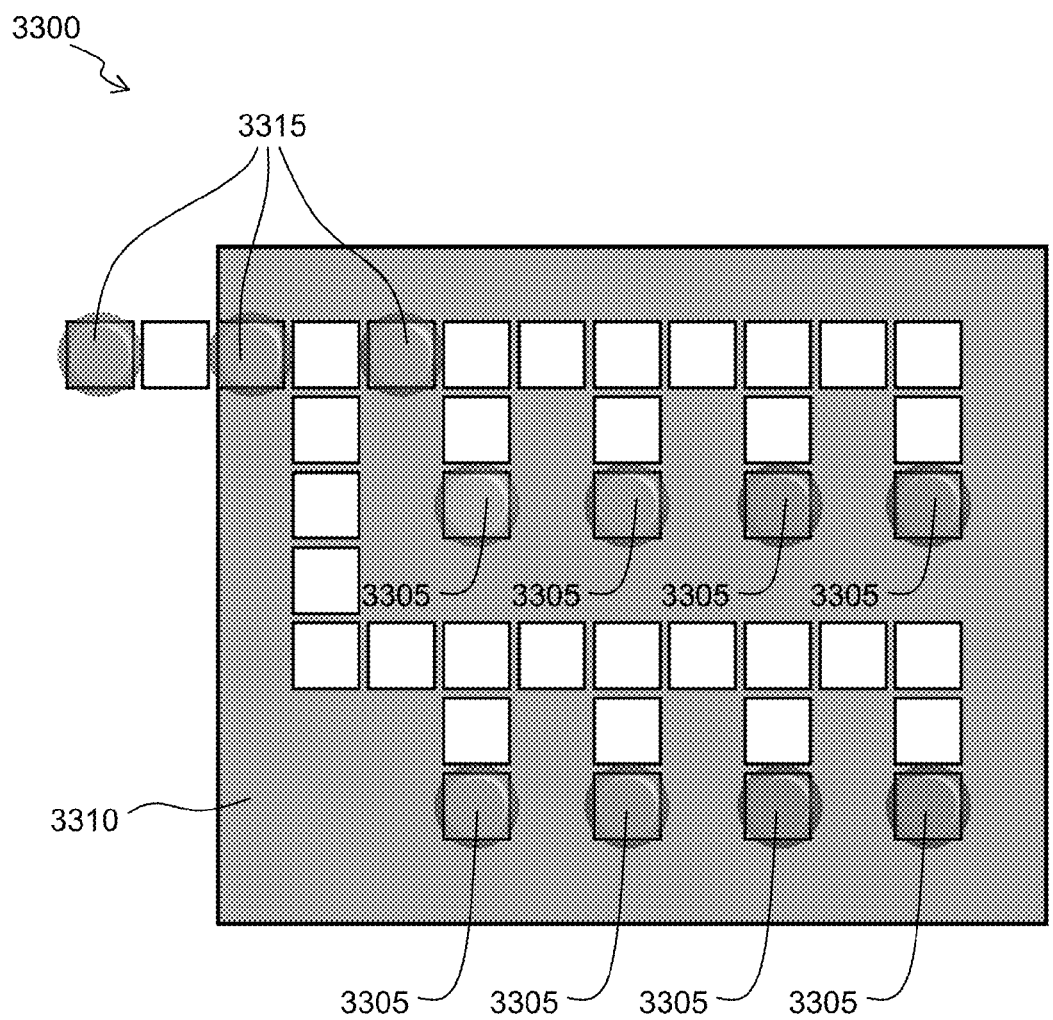
FIG. 33 illustrates an embodiment in which an electrode configuration is used to array reaction droplets.

FIG. 33 illustrates an embodiment in which an electrode configuration 3300 is used to array reaction droplets 3305. Reaction droplets 3305 may be thermal cycling droplets (e.g., amplification-ready droplets), as illustrated in certain other examples herein, or may be some other reaction in which a reaction is occurring over time. A temperature control element 3310 may be provided for thermal cycling or otherwise controlling temperature of reaction droplets 3305. Reaction quenching droplets 3315 may be transported into contact with reaction droplets 3305. Reaction quenching droplets 3315 may include one or more reagents for quenching or substantially quenching the reaction occurring in reaction droplets 3305. In one embodiment, the reactions in reaction droplets 3305 are started substantially simultaneously, and reaction droplets 3305 are combined with reaction quenching droplets 3315 sequentially. Following quenching, the combined droplets may be subject to further assay steps and/or detection for developing a curve indicative of reaction kinetics. In another embodiment, the reactions in reaction droplets 3305 are started sequentially, and reaction droplets 3305 are combined with reaction quenching droplets 3315 substantially simultaneously. Likewise, following quenching, the combined droplets may be subject to further assay steps and/or detection for developing a curve indicative of reaction kinetics. In an intermediate process, reactions are started sequentially and quenched sequentially.

Note that in any of the various embodiments of the invention which reaction droplets are combined with reaction quenching droplets, the reaction droplets may be transported into contact with the reaction quenching droplets, the reaction quenching droplets may be transported into contact with the reaction droplets, and/or the reaction droplets and reaction quenching droplets may be transported into each other. Quenching droplets may be delivered as needed or may arrayed with reaction droplets and combined according to a predetermined timing protocol.

One advantage of this approach in a thermal cycling amplification protocol is that following quenching, droplets can continue to be subject to thermal cycling, but amplification will cease as a result of combination with the quenching droplets.

In a related embodiment, the applicants have discovered that certain reactions, such as nucleic acid amplification, can be quenched using electrostatic fields. For example, a reaction may be stopped by applying a voltage signal to the underlying electrode or to another electrode in the vicinity of the droplet. The voltage signal applied may be selected so as to be sufficient to stop or substantially stop the reaction. For example, the voltage signal required to stop the amplification reaction may simply be a sustained voltage signal relative to the voltage signal required to conduct droplet transport from one electrode to the next. Thus, for example, a nucleic acid amplification reaction may be stopped by stopping the transport of the nucleic acid amplification droplet and retaining the droplet on an activated electrode for a period of time which is sufficient to stop the reaction. Voltage level, cycle, and/or voltage type may also be adjusted until the amplification reaction is substantially stopped. In some cases, an electrode configuration may include a specialized deactivation site at which an electrode is present having characteristics selected to deactivate a reaction at the site. Further, in embodiments in which amplification is conducted using droplets arrayed on electrodes, it may in some cases be helpful to deactivate or otherwise control voltage on the electrode underlying the amplification-ready droplet during amplification, so that the electrode does not cause undue interference with the continued amplification of the droplet.

In another related embodiment, a droplet actuator may include one or more inhibitors located in proximity to droplet operations electrodes. For example, the inhibitors may be dry inhibitor reagents dried on the surface of the droplet actuator. As another example, an inhibitor may be a material such as platinum or nitride which is known to inhibit PCR. For example, the inhibitor may be an exposed platinum pad or wire arranged so that a droplet may be transported into contact with the pad or wire in order to stop the reaction. The inhibitors may, in some embodiments, be arrayed at various electrode locations on the droplet actuator.

In operation, the reaction droplets may be sequentially transported into contact with the inhibitors, and the droplets may be subsequently subjected to further assay steps and/or detection steps in order to develop a curve indicative of the endpoint of the reaction at the time the reaction was stopped. Similarly, the reactions may be started sequentially, and transported simultaneously into contact with an array of inhibitors. In another embodiment, the reactions may be started sequentially, and the droplets may be transported sequentially into contact with the inhibitors. In any event, the droplets will include droplets having undergone different reaction periods or thermal cycles, and reaction products in the droplets can be subjected to further assay steps and/or detection steps in order to develop a curve indicative of the progress of the reaction relative to time or cycles.

7.8 Sampling a Reaction Time Course

The invention provides a related embodiment in which a droplet actuator is provided and a reaction droplet is provided on the droplet actuator. The reaction droplet is characterized in that one or more reactions are taking place in the reaction droplet. For example, the reactions may include chemical reactions, biochemical reactions and/or biological reactions. As the reactions progress, one or more sub-droplets is dispensed from the reaction droplet. Each such sub-droplet may be treated in a manner which stops the reaction. For example, the temperature of a sub-droplet may be adjusted to the temperature in which the reaction is stopped or substantially stopped. As another example, each sub-droplet may be combined with a reagent droplet including a reagent that quenches the reaction. Each sub-droplet may be removed from the parent reaction droplet at a different time, and the sub-droplets may be subjected to further analysis to develop a curve indicating the time-course of the reaction. In a related embodiment, the reactions in the sub-droplets are not quenched, but each sub-droplet is subjected to detection promptly after being dispensed from the parent reaction droplet. In yet another embodiment, a parent droplet may be subdivided into numerous sub-droplets, and the sub-droplets may be subjected to a detection protocol in which each sub-droplet is subjected to detection at a different time. Data gathered may be used to develop a curve indicative of the kinetics of the reaction. In one embodiment, the dispensing of sub-droplets is mediated by electrodes, e.g., electrowetting-mediated dielectrophoresis-mediated droplet dispensing.

In a related embodiment, reaction kinetics are measured by combining droplets on a droplet actuator to start a series of reactions at different times, followed by imaging the droplets at the same time, and using the data to develop a curve indicative of the kinetics of the reaction. In yet another related embodiment, reaction kinetics are measured by combining reagent droplet on droplet actuator to start a series of reactions at different times, followed by scanning the reaction droplets with a sensor at different times, and developing a curve based on the different reaction periods indicative of the kinetics of the reaction. In any of these embodiments, the reaction may or may not be stopped prior to detection, depending on the requirements of the particular reaction in question.

7.9 Additional Thermal Cycling Embodiments

Figure 34:
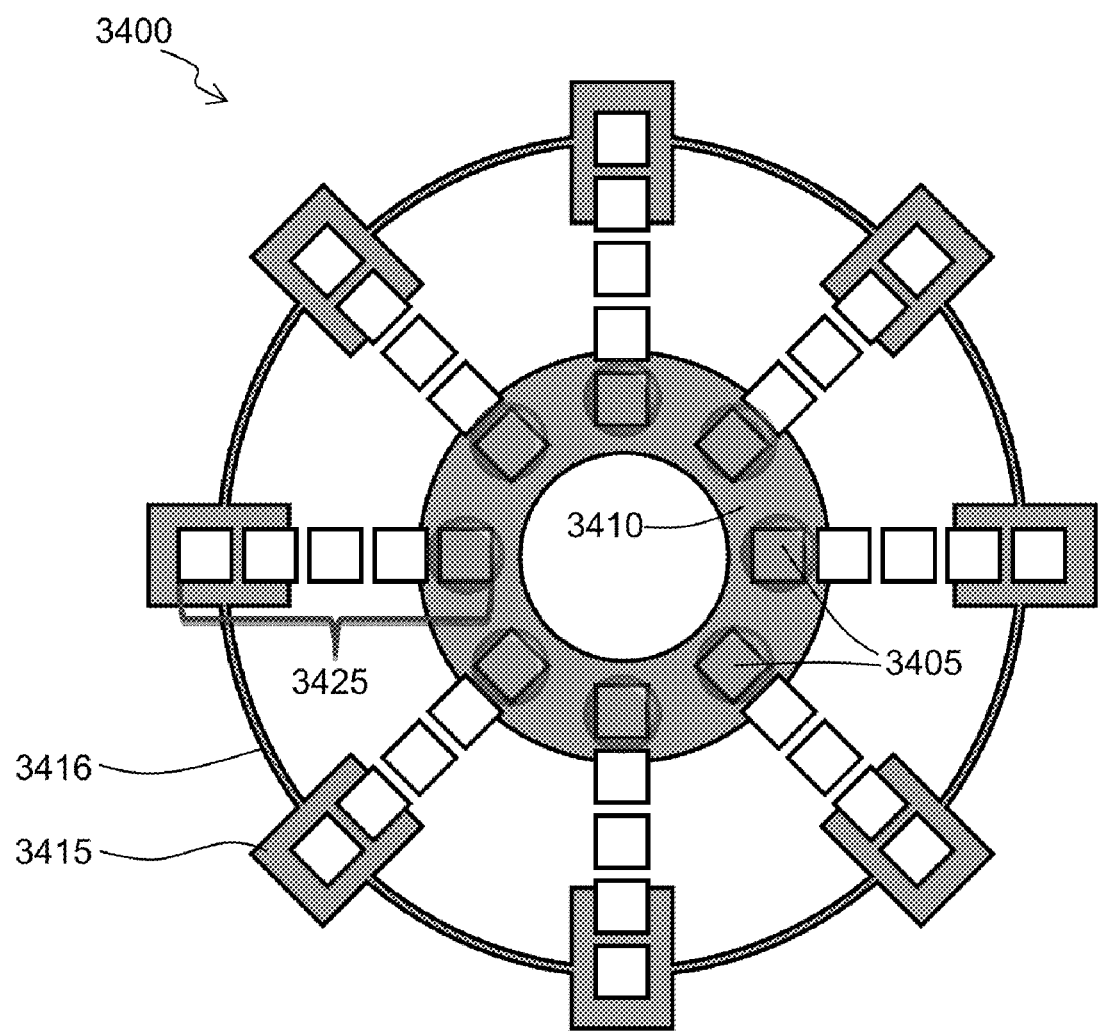
FIG. 34 illustrates an electrode configuration of a droplet actuator of the invention in which thermal cycling paths are arranged radially.

A wide variety of additional embodiments with various attributes are possible within the scope of the invention. A few examples follow:

FIG. 34 illustrates an electrode configuration 3400 of a droplet actuator of the invention in which thermal cycling paths 3425 are arranged radially. A central temperature control element 3410 is ring shaped. Temperature control element 3410 may be the wide variety of alternative shapes, such as disk shaped, hexagonal, octagonal, etc. In the embodiment illustrated, thermal cycling paths 3405 radiate outwardly from temperature control element 3410. Outer temperature control elements 3415 are also provided. Electrode paths 3425 extend from central temperature control element 3410 to outer temperature control elements 3415. Electrode configuration 3400 may be provided as part of a larger electrode configuration. Droplets may be introduced to electrode paths 3425 via openings to the exterior of the droplet actuator and/or via other electrode paths (not shown); or in an open system lacking a top substrate, droplets may simply be deposited on the droplet operations surface. Outer temperature control elements 3415 are illustrated as individual temperature control elements connected by wire 3416. However, it will be appreciated that outer temperature control elements 3415 may be differently shaped; for example, outer temperature control elements 3415 may be replaced by single ring-shaped outer temperature control element, e.g., a ring having a circular, hexagonal, octagonal, or other ring configuration.

Figure 35:
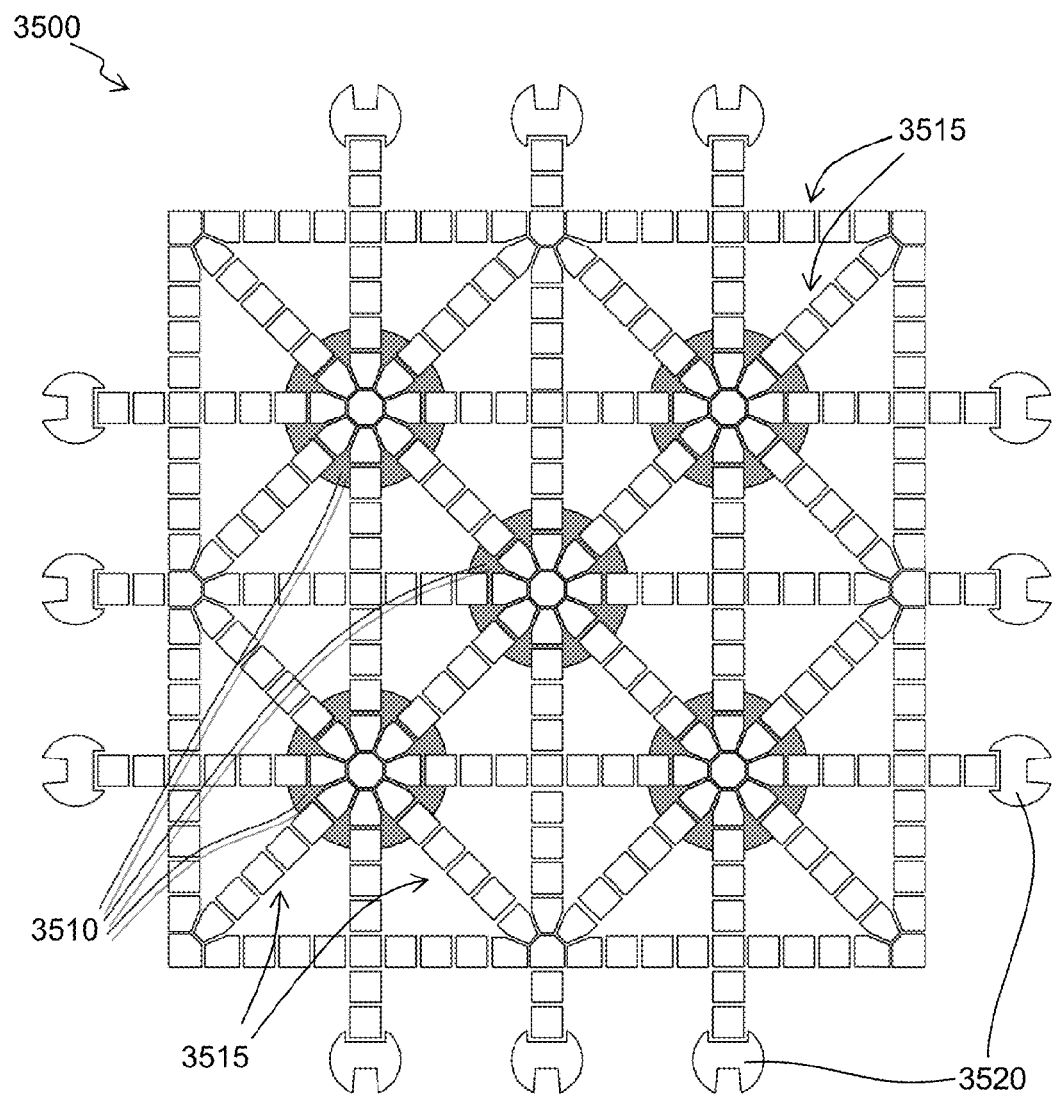
FIG. 35 illustrates electrode configuration having multiple temperature control elements connected by an electrode array having multiple sets of droplet transport paths.

FIG. 35 illustrates electrode configuration 3500 having multiple temperature control elements 3510 connected by an electrode array having multiple sets of droplet transport paths 3515. Reservoir electrodes 3520 are also provided adjacent to droplet transport paths 3515. Temperature control elements 3510 may be the same or different. Temperature control elements 3510 may be used to establish temperature control zones. Temperatures in the temperature control zones may be the same or different.

Figure 36:
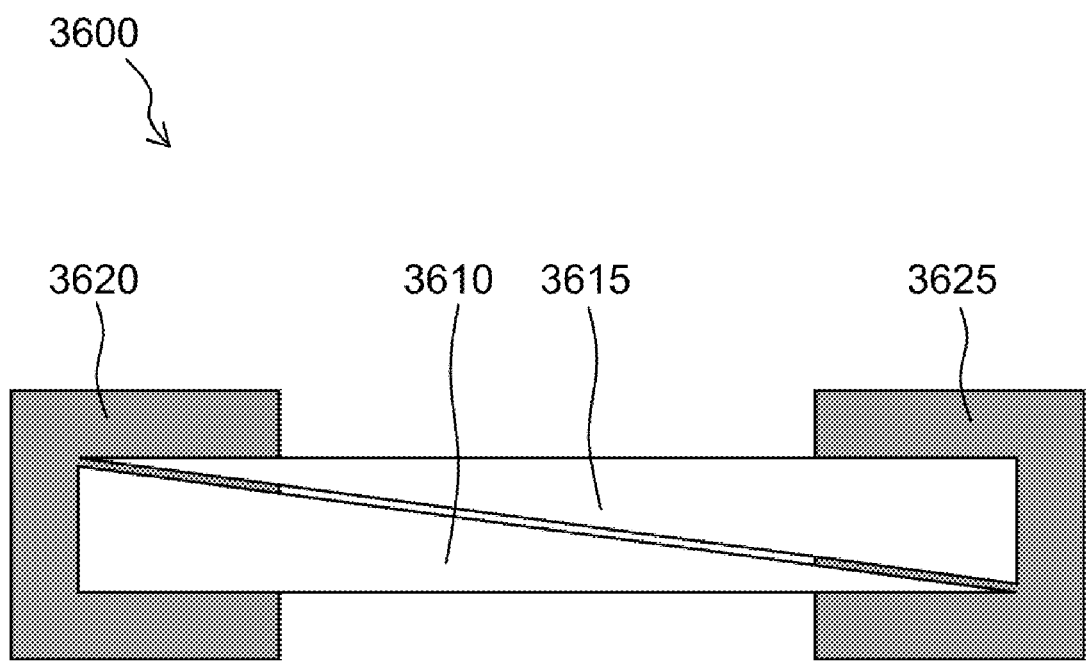
FIG. 36 illustrates an electrode configuration in which tapering electrodes and are used to transport a droplet between temperature control elements.

FIG. 36 illustrates an electrode configuration 3600 in which tapering (e.g., elongated triangular or wedge-shaped) electrodes 3610 and 3615 are used to transport a droplet between temperature control elements 3620 and 3625. Activation of electrode 3610 while electrode 3615 is deactivated will transport a droplet towards temperature control element 3620. Activation of electrode 3615 and the deactivation of electrode 3610 will transport the droplet from temperature control element 3620 back to temperature control element 3625. This kind of electrode configuration or other configurations making use of electric field gradients may also be used, such as those described in International Patent Application No. PCT/US2008/80275, entitled "Droplet Actuator Structures," filed on Oct. 17, 2008, the entire disclosure of which is incorporated herein by reference.

Figure 37:
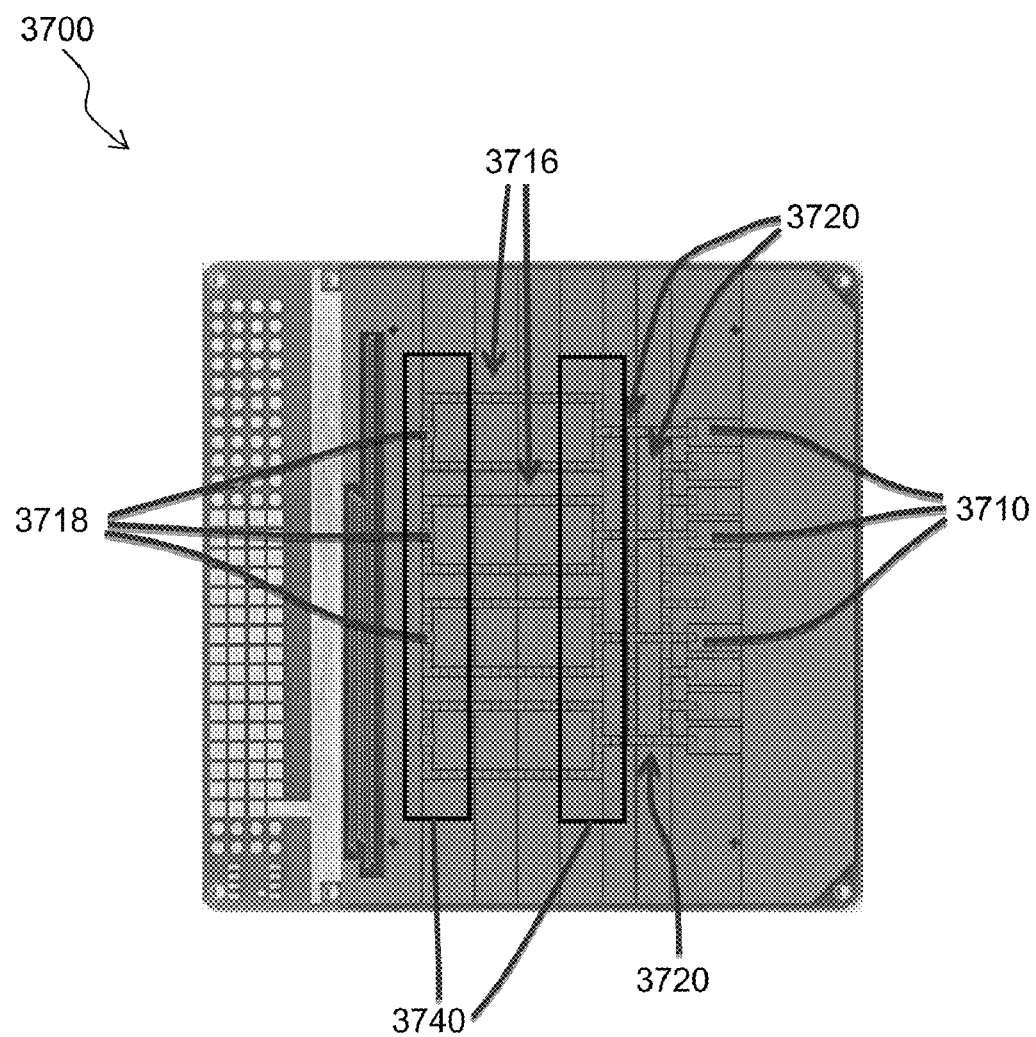
FIG. 37 is a photograph of a bottom substrate of a droplet actuator cartridge of the invention.

FIG. 37 is a photograph of a bottom substrate 3700 of a droplet actuator cartridge of the invention. The layout (copper on a printed circuit board), includes reservoir electrodes 3710 for dispensing sample and reagents. The layout includes electrode loops 3716 for circulating droplets between temperature zones 3740. The layout includes transport paths 3720 for conducting droplet operations using reagent and/or sample droplets. For example, transport paths 3720 may be used for transporting reagent and/or sample droplets between reservoir electrodes 3710 and electrode loops 3716 and/or sample preparation operations or and/or other droplet operations. The layout includes detection electrodes 3718. Detection electrodes 3718 are larger than the other droplet operations electrodes making up the electrode loops 3716 and transport paths 3720. The droplet actuator cartridge may include a top substrate (not shown) covering the electrode arrangement and separated from the bottom substrate to form a droplet operations gap suitable for conducting droplet operations. The top substrate may include a reference electrode or ground electrode electrically exposed to droplets in the droplet operations gap. Examples of suitable top substrates include those described in International Patent App. No. PCT/US2008/075160, entitled "Droplet Actuator with Improved top Substrate," filed on Sep. 4, 3708. The droplet operations gap may be filled with a liquid filler fluid, such as a liquid filler fluid that is immiscible with the droplets being subjected to droplet operations.

Figure 38:
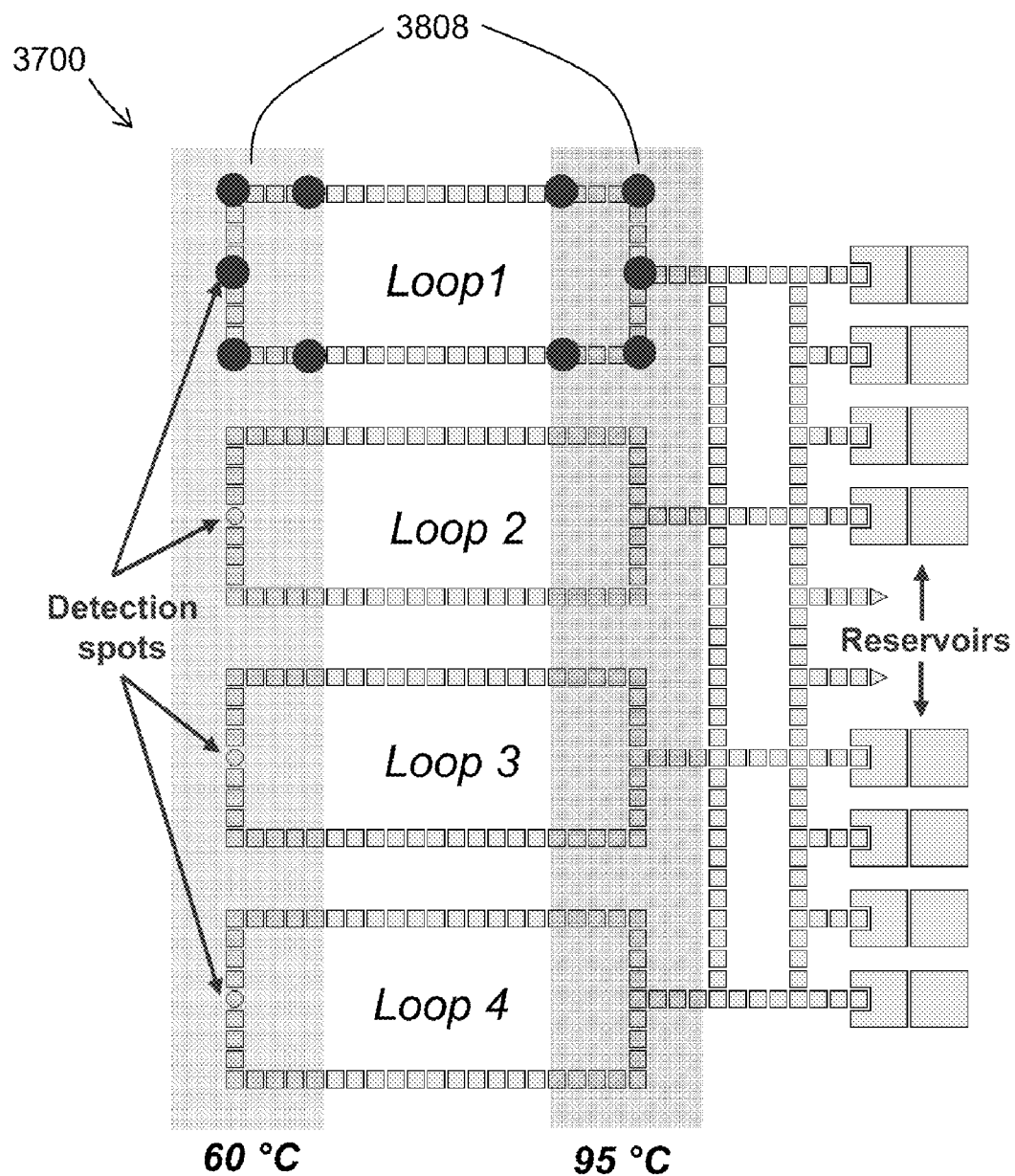
FIG. 38 is a diagram of the layout of the bottom substrate shown in FIG. 37.

FIG. 38 is a diagram of the layout of the bottom substrate 3700 shown in FIG. 37. The diagram illustrates the positioning of heater bars 3808 which are used for creating thermal cycling temperature zones on the cartridge.

FIGS. 39-43 show results of a thermal cycling experiment run using the cartridge layout shown in FIGS. 37 and 38. Experimental details were as follows:
  MRSA/Eva Green System:
    Target: 176 bp fragment of mecA gene (8-10 copies per genome)
    Sample: Methicillin resistant *Staphylococcus aureus* (MRSA) gDNA (ATCC#700699D-5) in buffer
    Quantitation Experiments:
    100,000-1 copies MRSA genome (300 pg-3 fg gDNA in reaction)
    Same amount of DNA was added to 660 mL droplet actuator reaction and BioRad 50 µL reaction (75× concentration difference)
    PCR Mixture:
    Eva Green dye
    Platinum Taq
    Filler Fluid:
    hexadecane
    Thermal Program (Typically):
    Hotstart: 60 s @ 95,
    40 cycles: (10 s 95 C, 20 s @ 60 C)

A comparison experiment was run on the droplet actuator and a commercial real-time PCR system (BioRad IQ5). The amount of input genomic DNA was varied to correspond to the amount of DNA in 1 to 100,000 MRSA cells. $C_T$ values were as follows:

|  | 100,000 | 87,000 | 10,000 | 1,000 | 100 | 10 | 1 | 0 |
|---|---|---|---|---|---|---|---|---|
| Cartridge | — | 14.3 | 16.4 | 20.1 | 23.2 | 27.1 | 29.2 | — |
| Bio-Rad | 20.4 | — | 23.5 | 27.1 | 30.4 | 34.2 | 35.5 | 38.3 |

Figure 39:
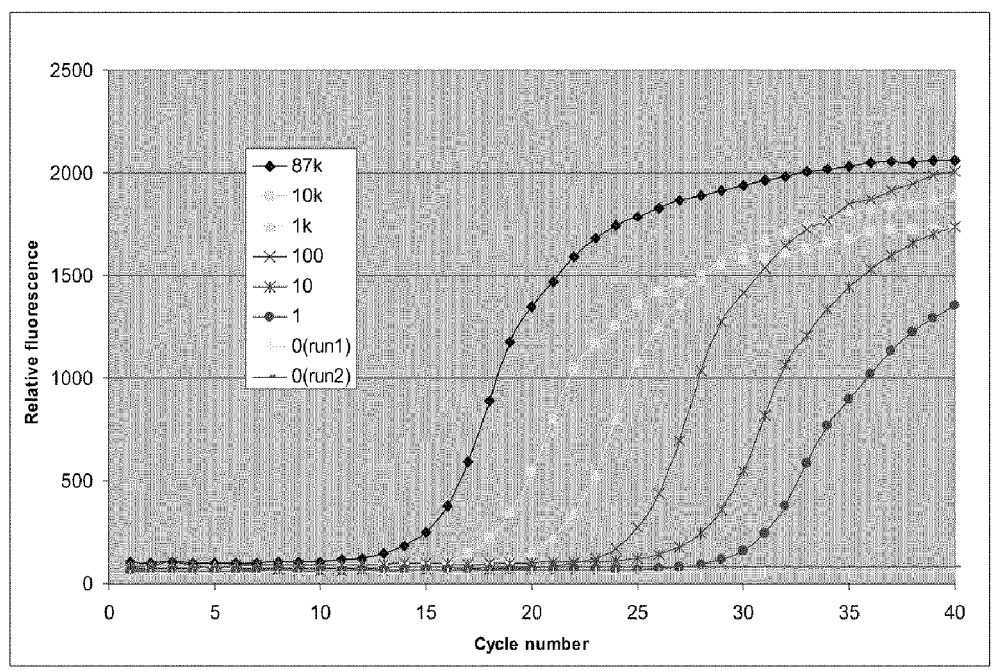
FIG. 39 shows raw data and normalized data for the on-cartridge amplification.
Figure 39:
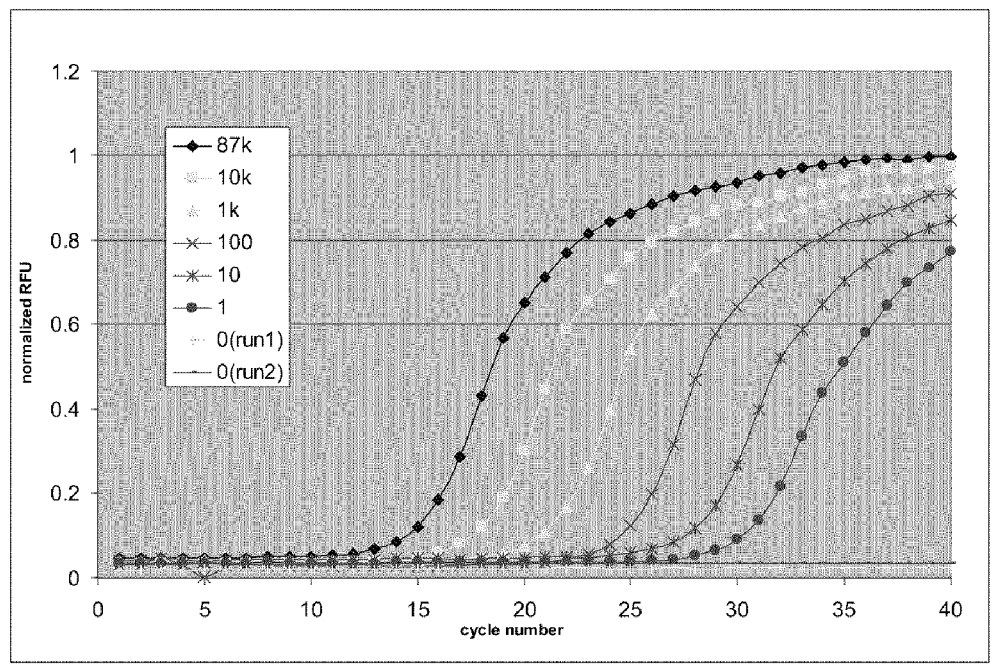

FIG. 39 shows raw data and normalized data for the on-cartridge amplification.

Figure 40:
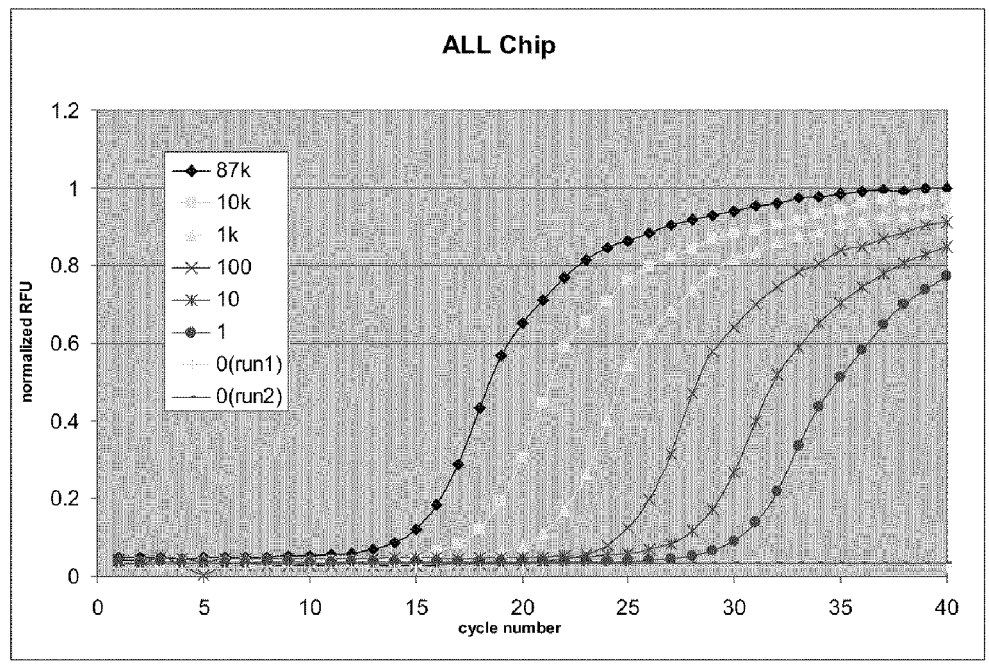
FIG. 40 shows normalized data from the cartridge of the invention compared with normalized data from the Bio-RadIQ5.
Figure 40:
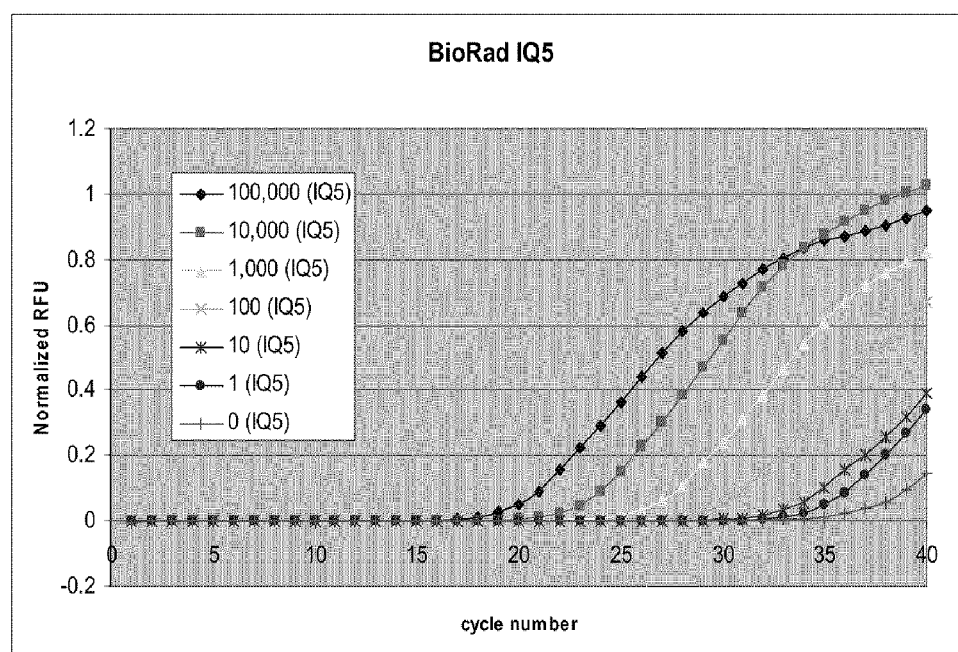

FIG. 40 shows normalized data from the cartridge of the invention compared with normalized data from the Bio-RadIQ5.

Figure 41:
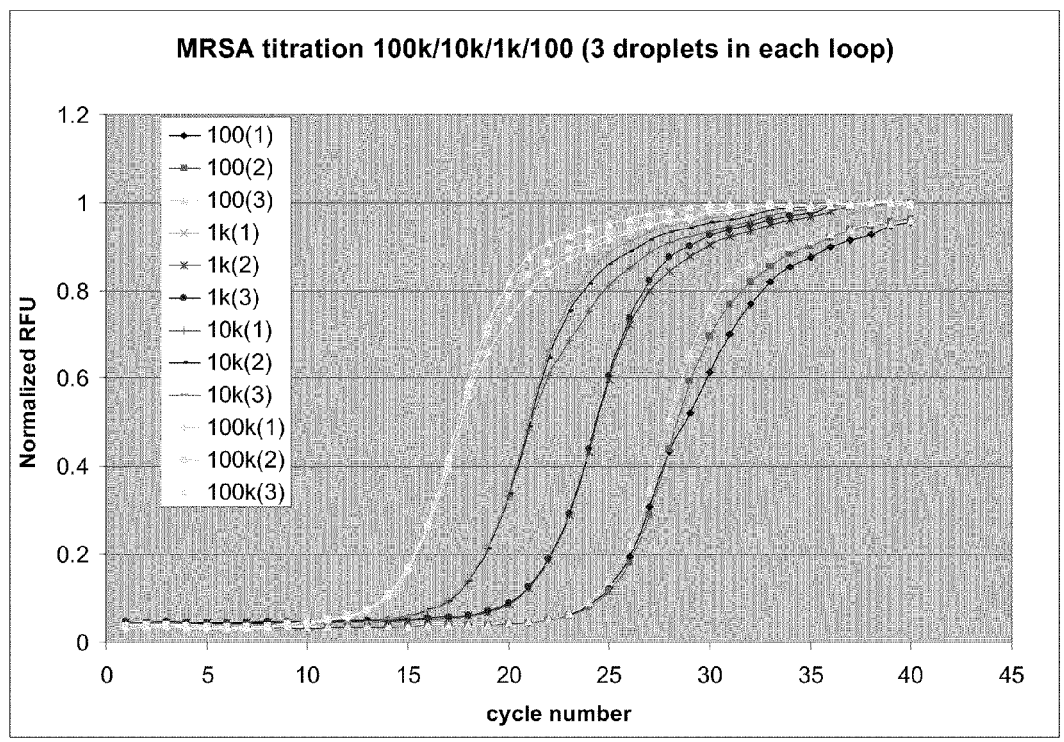
FIG. 41 shows the results of 12 simultaneous amplification reactions on one droplet actuator.

FIG. 41 shows the results of 12 simultaneous reactions (3 replicates each of 4 concentrations) on one droplet actuator. Each set of replicates was amplified on a single loop.

Figure 42:
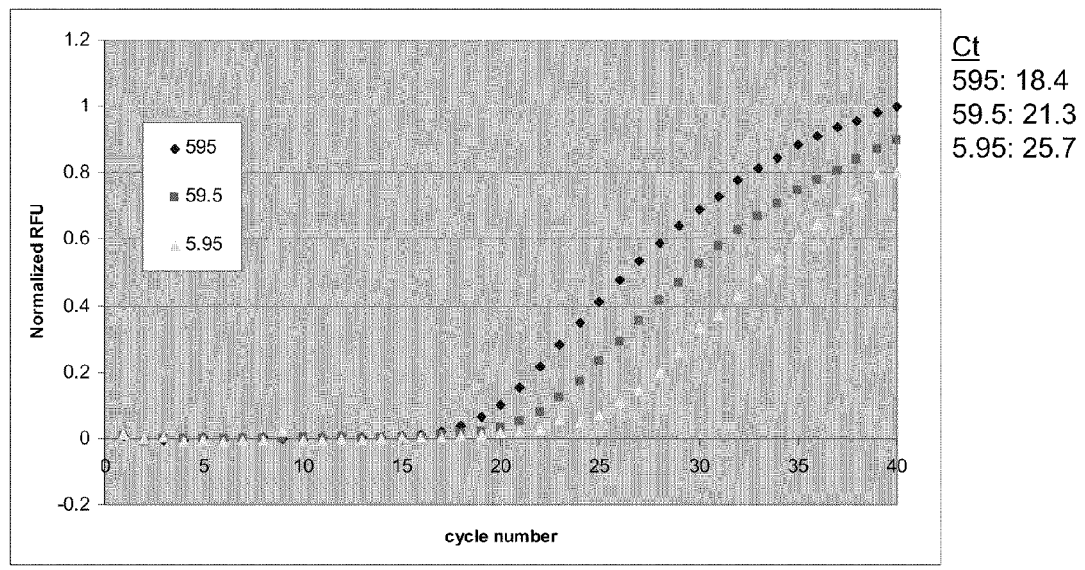
FIG. 42 shows results of another thermal cycling experiment using the cartridge layout shown in FIGS. 37 and 38.

FIG. 42 shows results of another thermal cycling experiment using the cartridge layout shown in FIGS. 37 and 38. Experimental details are as follows:
  *Candida albicans*/Taq Man System
    Target: 172 bp fragment of 18S ribsomal RNA gene (70-100 copies per genome)
    Sample: *Candida albicans* gDNA (ATCC#10232D-5)
    PCR Mixture
    TaqMan probe (FAM-BHQ)
    Bio-Rad iTaq
    Filler Fluid:
    Silicone oil
    Thermal Program
    Hotstart: 120 s @ 95 C
    40 cycles (15 s 95 C, 60 s @ 60 C)

Quantitation in FIG. 42 is by number of organisms or genome equivalents of the input amount of gDNA.

Figure 43:
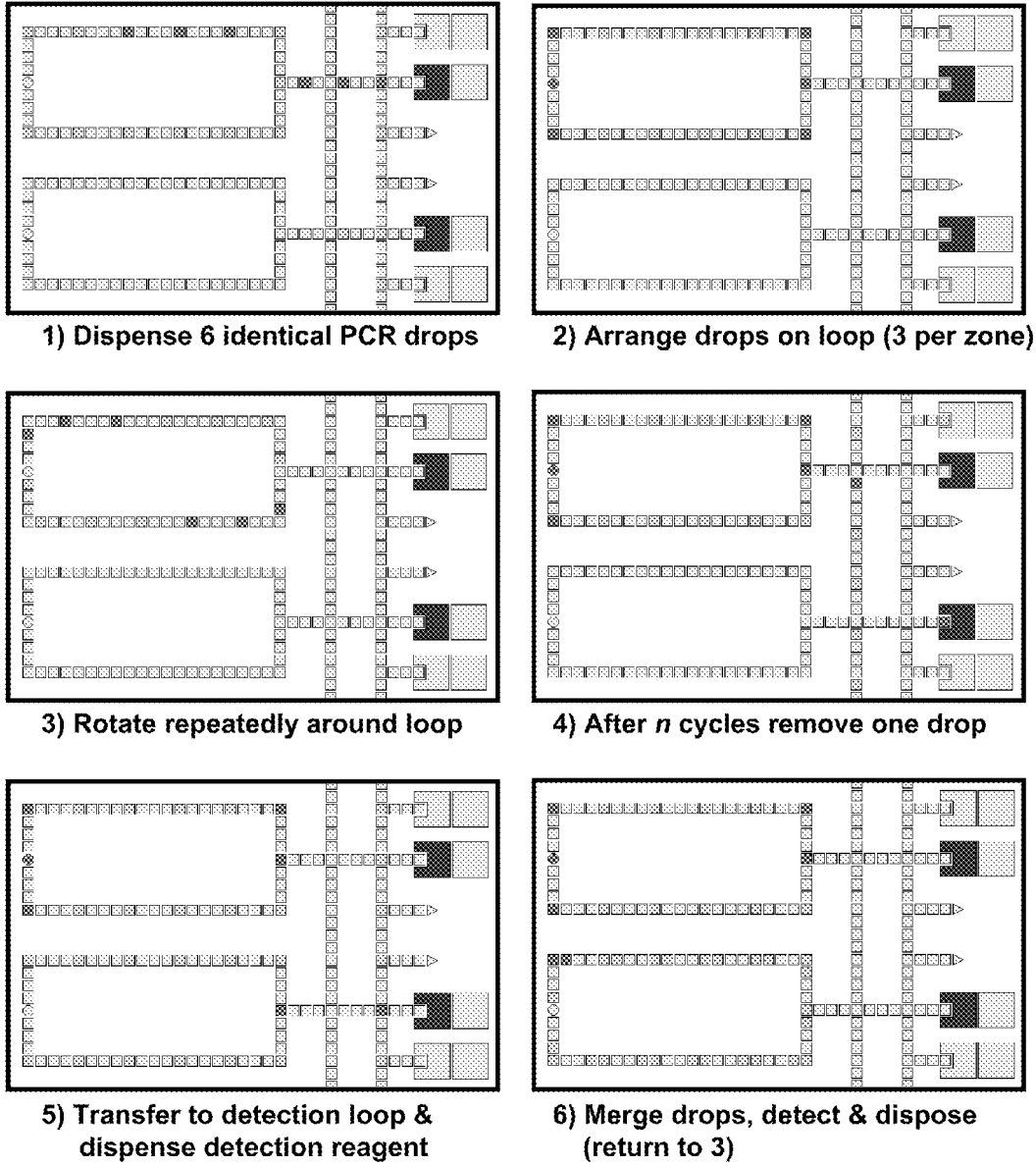
FIG. 43 shows results of the experiment described with respect to FIG. 44.

FIG. 43 shows the droplet protocol used in an experiment in which amplification is separated from detection. A population of identical droplets was thermal cycled without dye. Periodically, one droplet was removed, combined with a dye droplet, subjected to detection and then transported to a waste reservoir. The MRSA system described above was used, with 87,000 copies and 5 cycle separation. In step 1, six droplets were dispensed and transported onto a thermal cycling loop of the droplet actuator illustrated in FIGS. 37 and 38. The droplets included amplification reagents but lack detection reagents. In step 2, three of the droplets were arranged in each temperature control zone. In step 3, the droplets were rotated around the loop to effect thermal cycling. In step 4, after n thermal cycles, a droplet was removed from the thermal cycling loop. In step 5, the removed at droplet was transported away from the thermal zones. In step 6, the removed to droplet was combined with a detection droplet, subjected to detection, and disposed. Steps 4, 5, and 6 were repeated for subsequent droplets.

Figure 44:
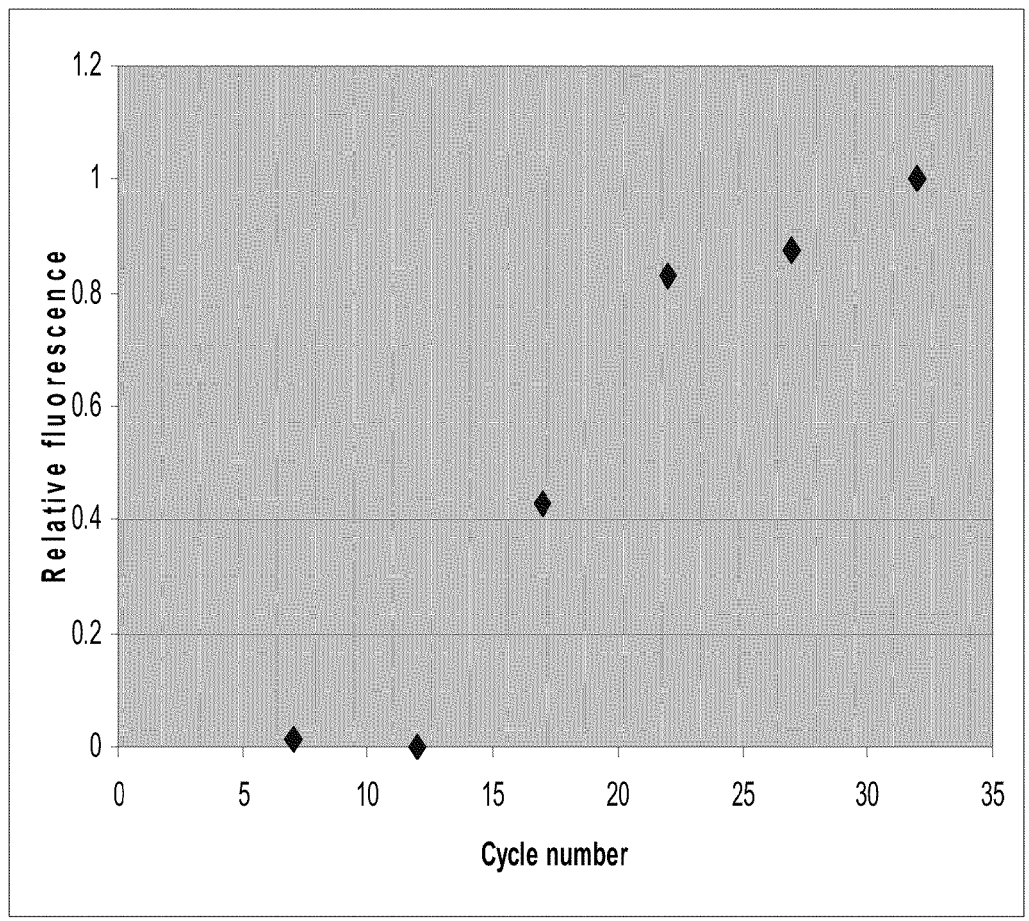
FIG. 44 shows a droplet protocol used in an experiment in which amplification is separated from detection.

FIG. 44 shows results of the experiment described with respect to FIG. 43. The results show that an amplification curve can be generated using a protocol in which amplification is separated from detection and in which a set of individual sub-sample droplets are differentially thermal cycled to produce a single real-time amplification curve.

7.10 Stopping Reactions

In various embodiments herein in which it is desired to quench or otherwise substantially stop a nucleic acid amplification reaction, a variety of reagents known to stop amplification reactions may be used. For example, reagents may interfere with polymerase activity, e.g., by binding to, denaturing and/or degrading the polymerase. Further examples are provided in the following table:

| Inhibitor | Proposed mechanism | Reference |
|---|---|---|
| Calcium ions | Competing with Mg++ as polymerase cofactor | Bickley et al. (1996) |
| EDTA | Chelation of Mg++ ions | Rossen et al. (1992) |
| Exopolysaccharides | Binding to DNA polymerase | Monteiro et al. (1997) |
| Heparin | Binding to nucleic acids | Satsangi et al. (1994) |
| IgG | Binding to nucleic acids | Abu Al-Soud et al. (2000) |
| Lactoferrin | Release of iron ions | Abu Al-Soud and Rådström (2001) |
| Phenol | Denaturation of DNA polymerase | Katcher and Schwartz (1994) |
| Proteinases | Degradation of DNA polymerase | Powell et al. (1994) |

7.11 Digital PCR

Digital PCR has been reported as a highly quantitative way to measure the exact number of template copies in a sample. A sample droplet may be dispensed or divided into multiple nanoliter size subunits. Most of the daughter droplets will include zero or one copy (some might have 2 or more copies due to Poisson distribution). The invention provides techniques for performing digital PCR on a droplet actuator. Small unit sized electrodes are preferable. In one embodiment, the electrodes are about 200×200 µm electrodes. The droplet operations gap height may also be adjusted. A droplet operations gap height of about 100 µm with the 200×200 µm electrodes will establish droplets having a volume of about 4 nL. Numerous such droplets may be generated using various droplet dispensing techniques. In one example, a series of electrodes are activated to produce an elongated chain, then an interspersed group of the activated electrodes is deactivated, yielding nanoliter-sized daughter droplets on the activated electrodes. Traditional dispense and transport techniques can also be used to form a series of daughter droplets. The entire droplet actuator may be thermal cycled to conduct amplification or individual droplets may be cycled through thermal control zones in order to effect thermal cycling. Droplets may be maintained in position throughout the reaction by voltage, chemical or physical patterning on the droplet actuator surface. The presence of amplified nucleic acid may be detected in the droplets, and the quantity of target nucleic acid may be determined.

Thus, for example, the invention provides method including providing a sample droplet comprising a target nucleic acid, and optionally comprising amplification reagents; dispensing sub-droplets from the sample droplet, and if amplification reagents are not present in the sample droplet, combining each sub-droplet with amplification reagents to yield an amplification-ready droplet; subjecting each sub-droplet to a thermal cycling protocol selected to amplify the target nucleic acid; detecting amplified product in each sub-droplet; and determining the number of sub-droplets that contain a sample portion from which said amplified product is formed. In some embodiments, at least one of said sub-droplets includes at least one target nucleic acid molecule. The amplification reagents may include any reagents suitable for amplifying the target. In some cases, the amplification reagents include at least one probe that hybridizes to amplified target molecules and has a fluorescence property that changes upon hybridization or as a consequence of hybridization. Determining the number of sub-droplets that contain a sample portion from which said amplified product is formed may include detecting the fluorescence change consequence to hybridization of said at least one probe. Determining the number of sub-droplets that contain a sample portion from which said amplified product is formed may include imaging all sub-droplets together, or imaging individual droplets or groups of droplets sequentially, e.g., by transporting droplets one at a time or in sub-groups through a detection window. The sub-droplets may have volumes less than about 1 µL. In other embodiments, the sub-droplets have volumes ranging from greater than about 1 µL to about 1000 µL, or from greater than about 100 µL to about 500 µL. Various steps of the method may be performed in a droplet operations gap or on a droplet operations surface of a droplet actuator. In some cases, the sub-droplets are compressed into a flattened or disk-shaped conformation between two substrates in the droplet operations gap. Where a droplet operations gap is provided, it may have any height suitable for conducting the required droplet operations. In some cases, the droplet operations gap has a height ranging from about 50 µm to about 1000 µm, or from greater than about 100 µm to about 500 µm. In certain embodiments, the thermal cycling is effected by transporting droplets from one thermal zone to another. In certain embodiments, the droplet actuator lacks sample chambers and/or lacks a flow-through channel. In certain embodiments, dispensing sub-droplets from the sample droplet is effected without a displacing fluid displacing sample from the flow-through channel. The sample droplet may be provided with amplification reagents, or the amplification reagents may be added using droplet operations, e.g., by combining each sub-droplet with amplification reagents to yield an amplification-ready droplet. The sample droplet may be provided with detection reagents, or the detection reagents may be added using droplet operations, e.g., by combining each sub-droplet with detection reagents to yield a detection-ready droplet. Detection reagents may be added before or after amplification.

In a related embodiment, after a sample droplet is divided to a set of nanoliter daughter droplets, a different set of primers may be mixed with each daughter droplet to conduct the PCR for a specific nucleic acid sequence. This approach facilitates assessment of the expression levels of multiple nucleic acids simultaneously on a droplet actuator.

7.12 Manipulating Magnetically Responsive Beads for Detection

In droplet actuator-based PCR (e.g., quantitative real-time PCR (QRT-PCR)), target nucleic acids may be immobilized on magnetically responsive beads for amplification reactions. To quantify amplification products, reaction droplets that include the magnetically responsive beads may be transported using droplet operations to a detection window on a droplet actuator. In some examples (e.g., QRT-PCR), detection of amplified product may employ fluorescent dyes, such as SybrGreen, to quantitate the amount of amplified product. However, magnetically responsive beads that are dispersed in the sample droplet may interfere with detection of the fluorescent dyes by blocking the fluorescent light from the detection device (e.g., a fluorimeter).

A magnetic field may be used to (a) remove magnetic beads from an amplification droplet for detection of unincorporated labeled nucleotides, or (b) pull droplets aside in an amplification droplet for detection of unincorporated labeled nucleotides.

Figure 45:
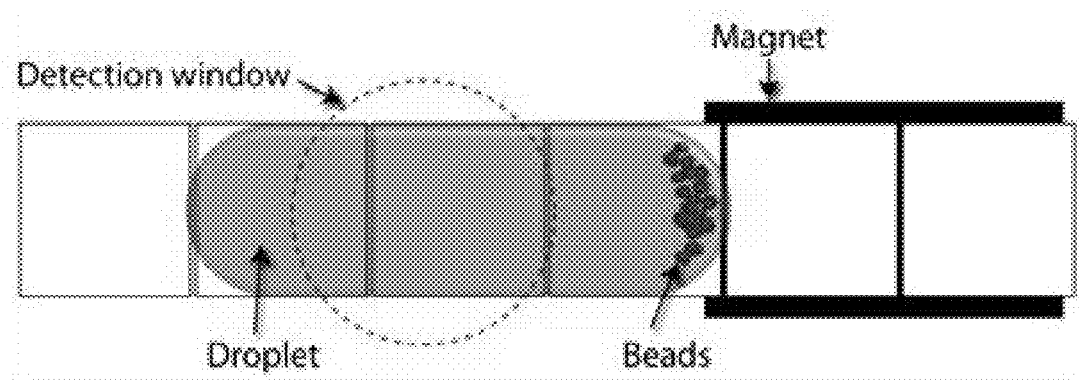
FIG. 45 illustrates an embodiment of the invention in which magnetically responsive beads are pulled aside within an elongated droplet so that no beads are exposed to the detection window during detection.

FIG. 45 illustrates an embodiment of the invention in which beads are pulled aside within an elongated droplet so that no beads are exposed to the detection window during detection. The magnet may, of course, be provided in a variety of arrangements in relation to the droplet operations surface or droplet operations. For example, as illustrated in FIG. 45, the magnet is situated under the droplet operations surface. However, the magnet may alternatively be situated atop the droplet actuator, laterally adjacent to the droplet actuator, in the droplet actuator gap, and/or in or partially in one or more of the substrates forming the droplet actuator. In short, the magnet may be provided in any position which attracts the beads to a region of the droplet which is outside of or at least substantially outside of the detection window.

In an alternative embodiment, the magnet may pull the beads entirely out of the droplet that is being subjected to detection. For example, a droplet actuator may include a powerful magnet in a region of the droplet actuator established for bead removal. The power of the magnet may be selected to pull magnetic beads out of any droplet which is moved into the bead removal region of the droplet actuator. In some cases, removal of the beads may effectively be irreversible.

Figure 46A:
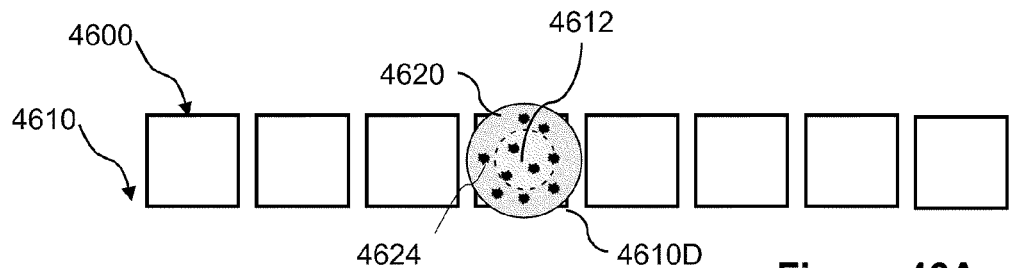
FIGS. 46A, 46B, and 46C illustrate top views of a region of a droplet actuator and together show certain steps of a method of manipulating magnetically responsive beads in order to improve analyte detection.
Figure 46B:
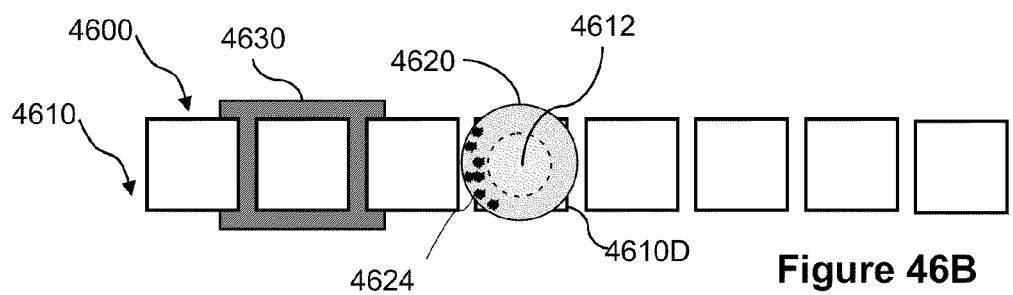
Figure 46C:
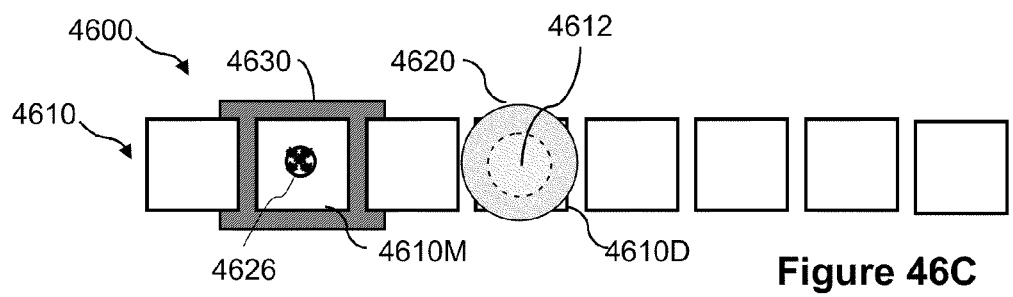

FIGS. 46A, 46B, and 46C illustrate top views of a region of a droplet actuator and show a method and results of manipulating magnetically responsive beads in order to improve analyte detection. Droplet actuator 4600 may include a path or array of droplet operations electrodes 4610 (e.g., electrowetting electrodes) that are configured for conducting droplet operations required for a nucleic acid-based assay, such as an amplification reaction, such as PCR. In particular, a detection window 4612 is provided on the droplet operations surface. Detection window 4612 may be located at a certain droplet operations electrode 4610D, or may be a region to which a droplet may be transported using droplet operations electrodes, optionally with other transport mechanisms, such as hydrophilic surfaces or variations in the topography of the top and/or bottom substrate. Droplet actuator 4600 may include a sample droplet 4620 that may be transported along droplet operations electrodes 4610 via droplet operations. Sample droplet 4620 may include a quantity of beads, such as magnetically responsive beads 4624 that have an affinity for a target nucleic acid to be analyzed.

As shown in FIG. 46A, sample droplet 4620 that has beads 4624 therein is positioned at droplet operation electrode 4610D, which is within the range of detection window 4612. Detection window 4612 is typically smaller in diameter than sample droplet 4620. Magnetically responsive beads 4624 are dispersed within sample droplet 4620 including the area occupied by detection window 4612 and may interfere with detection of the amplification signal, e.g., fluorescent dyes by blocking the fluorescent light from the detection device (i.e., a fluorimeter), resulting in scattered readings and background noise.

As shown in FIG. 46B, a magnet 4630 is positioned in proximity to sample droplet 4620. Magnet 4630 may be a permanent magnet or an electromagnet. Magnet 4630 is positioned at a distance from operation electrode 4610D and sample droplet 4620 to provide a sufficient magnet field to attract and aggregate magnetically responsive beads 4624 substantially to the edge of sample droplet 4620 and substantially away from detection window 4612. In some cases, the strength of the magnetic field provided by magnet 4630 is such that beads 4624 do not form a tight aggregate and may be easily redistributed in subsequent droplet operations. In other cases, aggregation is not an issue, as the bead removal is intended to be essentially permanent.

As shown in FIG. 46C, magnet 4630 may be used to separate magnetically responsive beads 4624 from sample droplet 4620. After a sufficient number of thermal cycle reactions (e.g., about 10 cycles), the amount of amplified nucleic acid in the liquid phase of a PCR droplet may be of sufficient quantity to be accurately detected in the absence of magnetically responsive beads. Using droplet operations, sample droplet 4620 may be transported via droplet operations into and out of the magnetic field of magnet 4630. As sample droplet 4620 is transported away from magnet 4630, a concentration of beads 4626 is left behind at droplet operations electrode 4610M. The volume of bead droplet 4626 may be just large enough the encapsulate beads 4624. Sample droplet 4620 is now sufficiently devoid of magnetically responsive beads and fluorescence detection may proceed in the absence of bead interference.

Figure 46D:
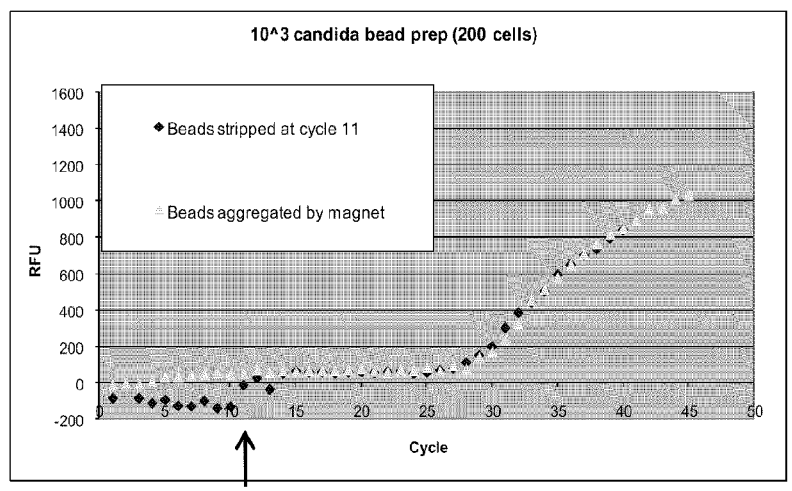
FIG. 46D shows a plot of real time PCR data that was obtained from thermal cycling reactions.

FIG. 46D shows a plot of real time PCR data that was obtained from thermal cycling reactions using the methods of FIG. 46B (i.e., magnetically responsive beads aggregated by a magnet) and FIG. 46C (PCR droplet devoid of magnetically responsive beads). FIG. 46D shows the instability and background noise in the detection signal that may result from the interference of magnetically responsive beads during detection of a fluorescent signal. When the magnetically responsive beads are removed, for example, at thermal cycle 11 (indicated by arrow) the detection signal is sufficiently stabilized.

7.13 Polar Fluorophores

Nucleic acid amplification methods use thermal cycling, i.e., alternately heating and cooling the a droplet including sample and amplification reagents through a defined series of temperature changes. In droplet actuator-based amplification (e.g., PCR conducted using droplet operations, such as electrode-mediated droplet operations), temperature control elements (e.g., Peltier units, heating blocks, cooling units, etc.) may be used to control the temperature of the filler fluid in the on a droplet actuator surface or in a droplet actuator gap. However, the elevated temperature required for thermal cycling may cause loss of a detection signal when fluorescence enhancement is used as a detection method and a fluorescent dye (i.e., fluorophore), such as SybrGreen, is used as a detection dye. Cell-permeable fluorophores, such as the SYBR® Green dye, may have sufficient solubility in a hydrophobic phase (e.g., oil filler fluid) and may partition from an aqueous PCR droplet into the filler fluid, particularly at elevated temperatures, such as those that occur during thermal cycling.

As an alternative to cell-permeable fluorophores, polar or cell-impermeable fluorophores may be used. For example, the EVAGREEN® polar fluorophore may be used in PCR without significant loss of a fluorescence detection signal. A number of different polar fluorophores, such as EVAGREEN® polar fluorophore (available from Biotium, Hayward, Calif.) and TO-PRO1 may be used in PCR in order to detect amplification products.

7.14 Passivation

Nucleic acid amplification requires several steps that include a number of different reaction components, such as nucleic acid template, oligonucleotide primers, reagents and enzymes, that are included within a reaction droplet. Many of these components of an amplification droplet, such as nucleic acids, proteins (i.e., enzymes), and/or dye (e.g., fluorescent dye), may potentially be absorbed onto substrate surfaces (e.g., droplet operations electrodes) and/or be distributed into the filler fluid (e.g., oil filler fluid) of a droplet actuator. Loss of these critical components to the substrate surface and/or filler fluid of a droplet actuator may result in reduced efficiency of a PCR reaction and/or failure of a PCR reaction. In one embodiment, the invention provides a surface passivation technique, in which materials are made "passive" in relation to other materials prior to using the materials together. The surface passivation techniques of the invention may reduce and/or eliminate loss of critical components from an amplification droplet to the surface of a droplet actuator.

Passivation reagents (i.e., blocking agents) may be selected to reduce and/or prevent binding of nucleic acid templates and/or oligonucleotide primers to substrate surfaces and/or loss to filler fluid include. Examples include other nucleic acid molecules, such as non-target DNA molecules and/or additional quantities of oligonucleotide primers.

Passivation reagents (i.e., blocking agents) may be selected to reduce and/or prevent binding of proteins to substrate surfaces and/or loss to filler fluid. Examples include, but are not limited to, various polymers such as polyvinylpyrrolidone (PVP), polyethylene glycol (PEG); surfactants, such as Tween; and bovine serum albumin (BSA).

In one example, the surface of a droplet actuator is pre-treated with a quantity of passivation agent(s) that is included within a pre-treatment droplet. The pre-treatment droplet may be transported along one or more PCR paths of a droplet actuator through one or more reaction cycles. As the pre-treatment droplet is cycled in the PCR paths, passivation agents, such as nucleic acids, proteins (i.e., enzymes), and/or dye (e.g., fluorescent dye), may be absorbed onto substrate surfaces (e.g., droplet operations electrodes) and/or be distributed into the filler fluid (e.g., oil filler fluid) and effectively saturate potential absorption sites from subsequent binding of components in a PCR droplet. In another example, a quantity of passivation agent(s) may be added directly into a PCR droplet (i.e., dynamic passivation). In this example, the passivation agents within a PCR droplet may effectively compete with reaction components for available absorption sites on substrate surfaces and/or filler fluid of a droplet actuator.

7.15 Gap Height

Droplet actuators that are used to perform PCR may include a bottom substrate and a top substrate separated by a droplet operations gap. Because surface tension decreases with increasing temperature, if the surface tension is too low the droplet may split or fragment at an elevated temperature. Therefore, a gap height configuration that may work well at room temperature may not work at elevated temperatures because the surface tension is effectively reduced. The inventors have discovered that this effect can be compensated for by using a larger gap. The surface tension (energy) is the same for a larger gap, but the area is larger so more total energy is required for the droplet to fragment. Typically, the droplet operations gap height in a droplet actuator that is used to perform thermal cycling may be about 200 μm. However, too small of a gap height may result in fragmentation of an amplification droplet during droplet operations, such as when shuttling a droplet between thermal cycling zones. Fragmentation of a PCR droplet may result in loss of target nucleic acids and reagent components. Loss of these critical components may result in sufficiently reduced efficiency of an amplification reaction and/or failure of an amplification reaction.

The droplet operations gap height may be selected relative to the unit sized electrode and unit sized droplet volume such that the droplet is substantially spherical in shape. Lower aspect ratio droplets are more close to spherical size and the higher aspect ratio droplets are more disk-shaped. The inventors have discovered that disk-shaped droplets require less voltage for droplet operations such as droplet transport, dispensing, and splitting, but they also tend to form microdroplets more readily than more spherical droplets. Substantially spherical droplets require higher voltage for the same droplet operations, but they have a lower tendency to form microdroplets during droplet operations. In assays requiring droplets to be subjected to elevated temperatures, microdroplet formation is enhanced. In one example, the inventors found that electrode pitch:gap height ratios of 4:1 or 3:1 (equivalent to an electrode pitch of about 1200 μm and a droplet operations gap height of about 300 or about 400 μm) substantially reduced formation of microdroplets.

The invention provides for a droplet actuator that has increased gap height in order to improve droplet stability (e.g., sufficiently reduce fragmentation of a PCR droplet) during droplet operations. For example, a droplet operations gap height of about 320 μm to about 350 μm provides for improved stability of a PCR droplet transported via droplet operations.

In one embodiment, the electrode pitch of the unit sized droplet operations electrode is approximately 1200 μm, and the droplet operations gap has a height greater than about 250 μm. In another embodiment, the electrode pitch of the unit sized droplet operations electrode is approximately 1200 μm, and the droplet operations gap has a height ranging from about 250 μm to about 500 μm. In another embodiment, the electrode pitch of the unit sized droplet operations electrode is approximately 1200 μm, and the droplet operations gap has a height ranging from about 275 μm to about 450 μm. In another embodiment, the electrode pitch of the unit sized droplet operations electrode is approximately 1200 μm, and the droplet operations gap has a height ranging from about 300 μm to about 400 μm. In another embodiment, the electrode pitch of the unit sized droplet operations electrode is approximately 1200 μm, and the droplet operations gap has a height ranging from about 320 μm to about 375 μm. In another embodiment, the electrode pitch of the unit sized droplet operations electrode is approximately 1200 μm, and the droplet operations gap has a height ranging from about 320 μm to about 350 μm.

In one embodiment, the invention provides a droplet actuator having an electrode pitch:gap height ratio in the range of about 7:1 to about 2.8:1. In another embodiment, the invention provides a droplet actuator having an electrode pitch:gap height ratio in the range of about 6:1 to about 3:1. In yet another embodiment, the invention provides a droplet actuator having an electrode pitch:gap height ratio in the range of about 4.3:1 to about 3.4:1.

In another embodiment, the invention provides a droplet actuator having an electrode pitch of about 1200 μm and a droplet operations gap height ranging from about 175 μm (~7:1 aspect ratio) to about 450 μm (~2.8:1 aspect ratio). In yet another embodiment, the invention provides a droplet actuator having an electrode pitch of about 1200 μm and a droplet operations gap height ranging from about 200 μm (~6:1 aspect ratio) to about 400 μm (~3:1 aspect ratio). In yet another embodiment, the invention provides a droplet actuator having an electrode pitch of about 1200 μm and a droplet operations gap height ranging from about 280 μm (4.3:1) to about 350 μm (3.4:1).

Gap height in a droplet actuator may, for example, be controlled by "sandwiching" a spacer material of appropriate thickness between the lower and upper droplet actuator surfaces. Alternatively, a layer of material may be adhered to the inside surface of either top or bottom substrate to provide a stand-off to establish a gap spacing of appropriate thickness between at least a portion of the two substrates. Alternatively, the stand-off may be an integral part of one or both of the substrates, as for example, a protruding post or other structure molded or shaped into the substrate during an injection molding or other forming process. A variety of additional means of controlling the gap height to achieve the desired increased aspect ratio will be readily apparent to those of skill in the art.

7.16 Reduction of Carry-Over Contamination

Droplet-based nucleic acid amplification on a droplet actuator includes a sequence of droplet operations in which amplification-ready droplets are shuttled, using electrode mediated droplet operations, between thermal reaction zones and a detector. When this process involves multiple droplets travelling along a common path or nearby paths, residual components from an amplification droplet may carry from one droplet to another, contaminating subsequent amplification droplets in the sequence of droplet operations. The invention provides a droplet actuator for and method of reducing cross-contamination between amplification droplets that uses oil ensconced amplification droplets.

The droplet actuator of the invention may include a bottom substrate and a top substrate that is separated by a droplet operations gap. In designated areas of the droplet actuator, the droplet operations gap may include a liquid filler fluid, such as an oil filler fluid. In other designated areas of the droplet actuator, the droplet operations gap may be filled with a gaseous filler fluid, such as air.

An oil ensconced droplet may, for example, be formed by filling a sample reservoir with an oil, subsequently loading the reservoir with an aqueous sample, e.g., a PCR sample, and using droplet operations to dispense or "pinch off" an aqueous PCR droplet that is surrounded by an oil layer. To facilitate the formation of oil-ensconced PCR droplets, high-viscosity oils that have a high surface tension may be used. Examples of suitable oils include, but are not limited to, heptadecane or octadecane oils. As an oil-ensconced PCR droplet is dispensed, it may be transported using droplet operations into an area of the droplet actuator that is devoid of oil (i.e., gap is filled with air) for subsequent PCR reactions.

High viscosity oils may be partially solid or solid at ambient temperature (i.e., about 22° C. to 28° C.). For example the melting point of heptadecane, octadecane, nonadecane, and eicosane oils are 20-22° C., 26-29° C., 30-34° C., and 35-37° C., respectively. For droplet actuator-based amplification, an oil may be selected based on its melting temperature for different applications. For example, from a manufacturing standpoint where shipping of a droplet actuator is required, a reservoir may be filled with oil at a temperature above the melting point of the selected oil and then allowed to cool and solidify in the droplet actuator. Because droplet actuator-based PCR typically operates at about 60° C. or higher, the selected oil would be in the liquid phase and available for formation of oil-ensconced PCR droplets.

7.17 Concentration and Collection of Target Nucleic Acids

In some applications of droplet actuator-based nucleic acid amplification, it may be necessary to concentrate an analyte (e.g., bacterial, viral, fungal, and/or nucleic acid) in a sample fluid prior to PCR analysis. For example, the volume of a sample fluid may be too large and/or the concentration of an analyte to low to provide for optimum analysis.

FIGS. 47A through 47I illustrate a cross-sectional side view of a region of a droplet actuator 4700 and illustrate the use of magnetically responsive capture beads in a process of concentrating and collecting target nucleic acid from a sample fluid for nucleic acid amplification and analysis.

Figure 47A:
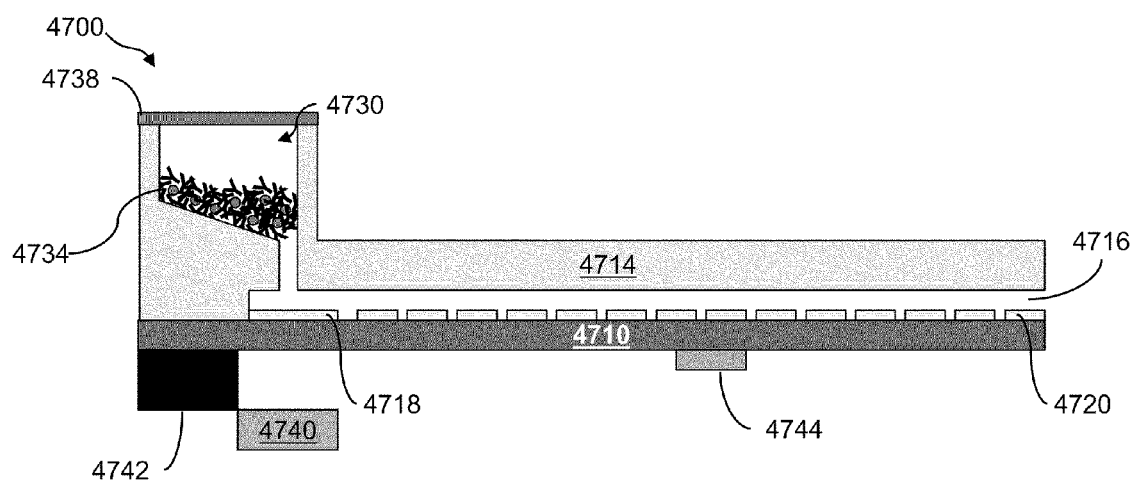
FIGS. 47A through 47I illustrate a cross-sectional side view of a region of a droplet actuator and provide an example of the use of magnetically responsive capture beads in a process of concentrating and collecting target nucleic acid from a sample fluid for nucleic acid amplification and analysis.

As illustrated in FIG. 47A, droplet actuator 4700 may include a bottom substrate 4710. Bottom substrate 4710 may be separated from a top substrate 4714 by a droplet operations gap 4716. A reservoir electrode 4718 may be disposed on bottom substrate 4710. Reservoir electrode 4718 may be arranged in association with a path or array of droplet operations electrodes 4720 (e.g., electrowetting electrodes), such that a droplet may be dispensed from the reservoir electrode 4718 onto the path or array of droplet operations electrodes 4720. A dielectric may overly the electrodes. A hydrophobic layer may overly the dielectric (or a hydrophobic dielectric may be selected). A reservoir 4730 is provided in top substrate 4714, establishing a liquid path from reservoir 4730 into gap 4716 and into sufficient proximity with reservoir electrode 4718 in order to permit the electrode to interact with a liquid flowed through the liquid path. Reservoir 4730 may be of sufficient size to include, for example, about 1 milliliter (ml) or more of a sample fluid. Reservoir 4730 includes a quantity of magnetically responsive capture beads 4734. Magnetically responsive capture beads 4734 may, for example, be beads that include a primary capture antibody, or oligonucleotide sequence, or any binding protein that has an affinity to a specific target analyte that provides for a binding and capture event. Reservoir 4730 is sealed by a septum 4738. Septum 4738 provides a barrier against contamination of reservoir 4730 by unwanted material.

A magnet 4740 is associated with droplet actuator 4700. The magnet is arranged such that reservoir electrode 4718 is within the magnetic field of magnet 4740. Magnet 4740 may, for example, be a permanent magnet or an electromagnet. In one example, magnet 4740 is a permanent magnet whose position is adjustable such that it may be moved into proximity of reservoir electrode 4718 or away from reservoir electrode 4718. Magnet 4740 may be used, for example, to attract and/or immobilize the magnetically responsive capture beads 4734. In operation, magnet 4740 may be used to assist in a process of concentrating a target analyte that is bound to magnetically responsive capture beads 4734.

A sonicator 4742 is associated with droplet actuator 4700. Sonicator 4742 may be used to apply sound energy (e.g., ultrasound) to a sample fluid in reservoir 4730 in order to agitate particles in the fluid. In one example, sonicator 4742 may be used to gently agitate and resuspend the particles in a sample fluid. In another example, sonicator 4742 may be used to vigorously agitate the particles in a sample fluid. In some applications, vigorous sonication may be used to disrupt cell membranes and release cellular contents. Additionally, the position of sonicator 4742 relative to reservoir 4730 may be varied.

A second magnet 4744 is associated with droplet actuator 4700. Magnet 4744 may, for example, be a permanent magnet or an electromagnet. Magnet 4744 is arranged such that one or more droplet operations electrodes 4720 are within the magnetic field of magnet 4744. Magnet 4744 may, for example, be used to provide a magnetic field for a second capture event using magnetically responsive beads in order to further concentrate and purify a target nucleic acid.

Figure 47B:
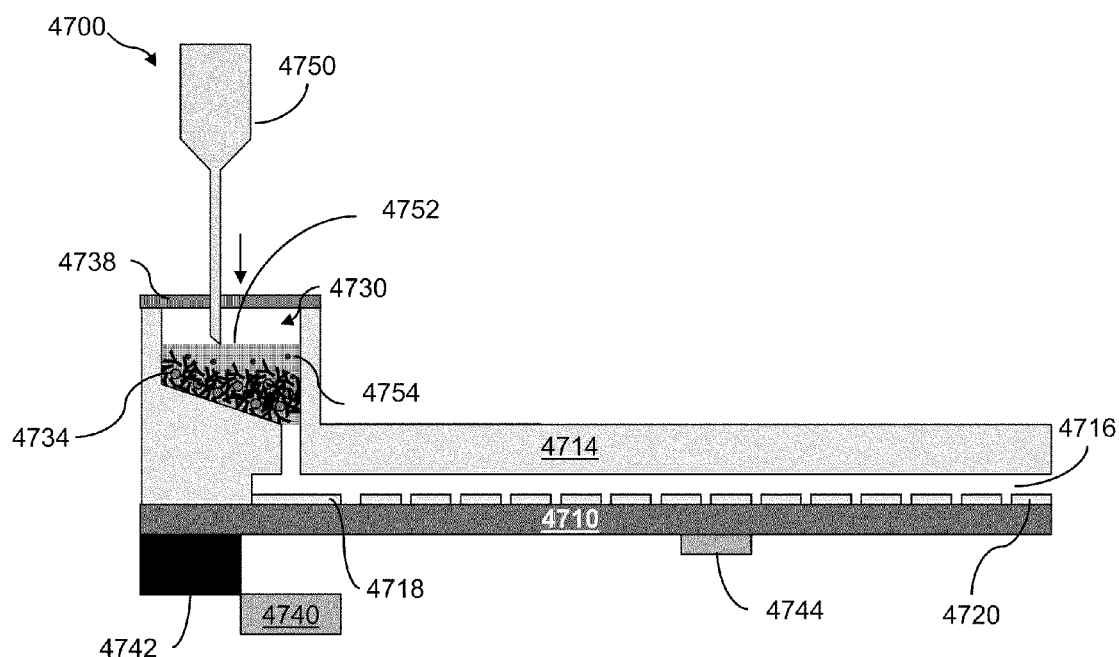

An example of a process of using magnetically responsive capture beads in order to concentrate and collect target nucleic acid from a sample fluid may include, but is not limited to, the following steps:

FIG. 47B shows a first step in a process of concentrating and collecting target nucleic acid from a sample fluid. In this step, a loading device 4750 (e.g., syringe and needle, micropipette) is used to deposit a quantity of sample fluid 4752 in reservoir 4730. Sample fluid 4752 may, for example, be a blood sample or a nasal pharyngeal wash sample of about 1 ml or more in volume. Sample fluid 4752 may include a quantity of target analytes 4754. Target analyte 4754 may, for example, be bacterial, viral, and/or fungal targets that have an affinity for magnetically responsive capture beads 4734. Because reservoir electrode 4718 is not activated and because the position of magnet 4740 is such that there is substantially no magnetic field present at reservoir electrode 4718, sample fluid 4752 is retained in reservoir 4730.

Figure 47C:
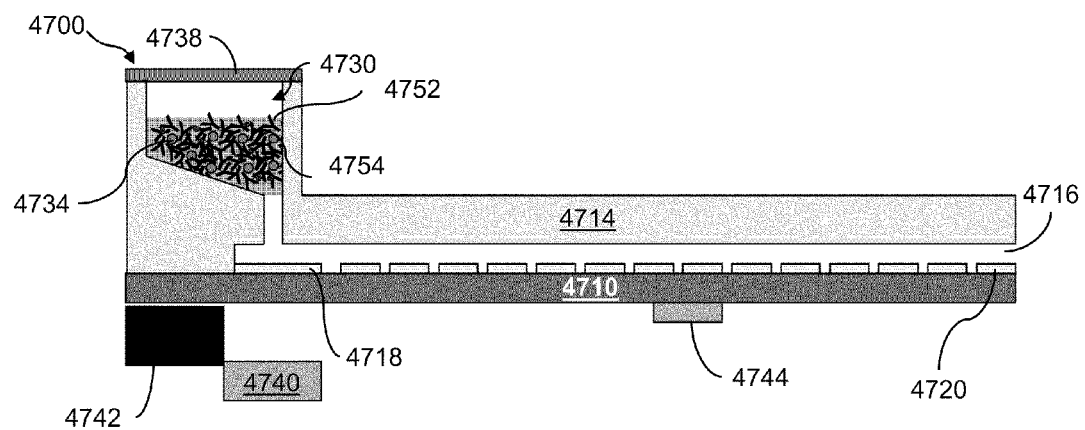

FIG. 47C shows another step in a process of concentrating and collecting a target nucleic acid from a sample fluid. In this step, sonicator 4742 is activated (e.g., low energy operation) and used to gently agitate and resuspend the magnetically responsive capture beads 4734 in sample fluid 4752. Sonciator 4742 may be activated for a period of time sufficient to provide optimum mixing and binding (i.e., primary capture) of target analytes 4754 to magnetically responsive capture beads 4734.

Figure 47D:
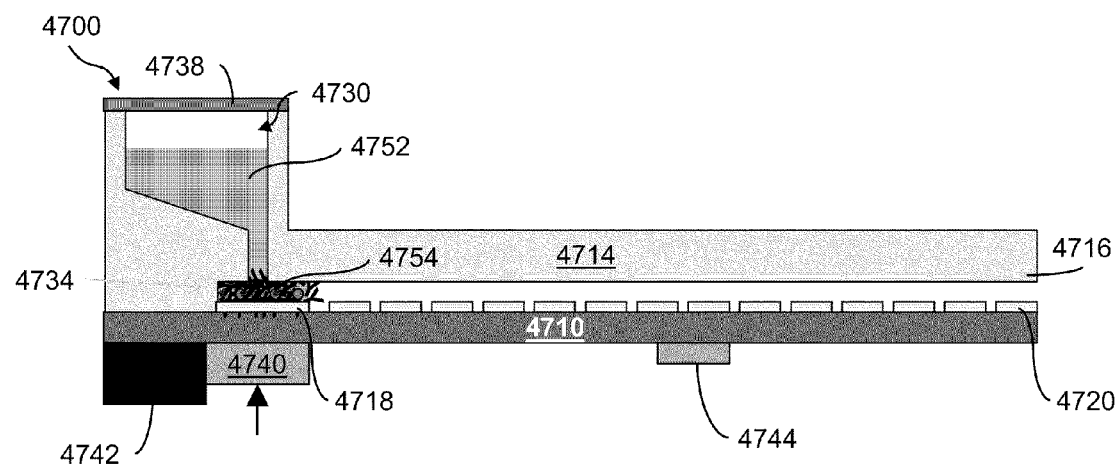

FIG. 47D shows another step in a process of concentrating and collecting a target nucleic acid from a sample fluid. In this step, sonicator 4742 is switched off, the position of magnet 4740 is such that there is a certain magnetic field present at reservoir electrode 4718 of droplet actuator 4700, and reservoir electrode 4718 is activated. As a result of the magnetic field and activation of reservoir electrode 4718, magnetically responsive capture beads 4734 that include bound target analyte 4754 settle at reservoir electrode 4718 and are effectively concentrated in sample fluid 4752.

Figure 47E:
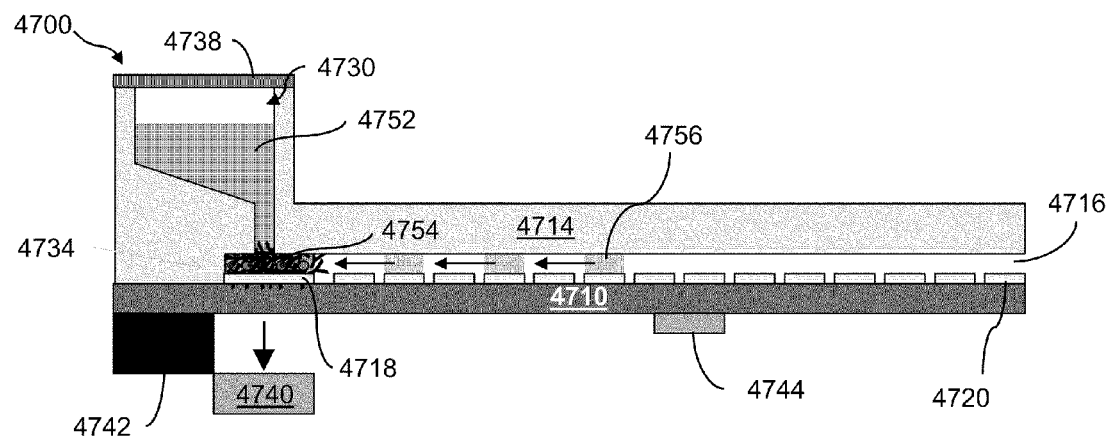

FIG. 47E shows another step in a process of concentrating and collecting a target nucleic acid from a sample fluid. In this step, magnet 4740 is physically moved away from droplet actuator 4700 such that there is substantially no magnetic field present at reservoir electrode 4718. As a result of the removal of the magnetic field, magnetically responsive capture beads 4734 are no longer immobilized on the surface of reservoir electrode 4718 and are distributed in a sample volume within gap 4716. In this example, when target analyte 4754 may, for example, be bacterial, viral, and/or fungal, lysis reagent droplet 4756 is transported and merged with the sample volume within gap 4716 using droplet operations. One or more lysis reagent droplets 4756 may be used to provide for sufficient lysis of target analyte 4754 and release of target nucleic acid.

Figure 47F:
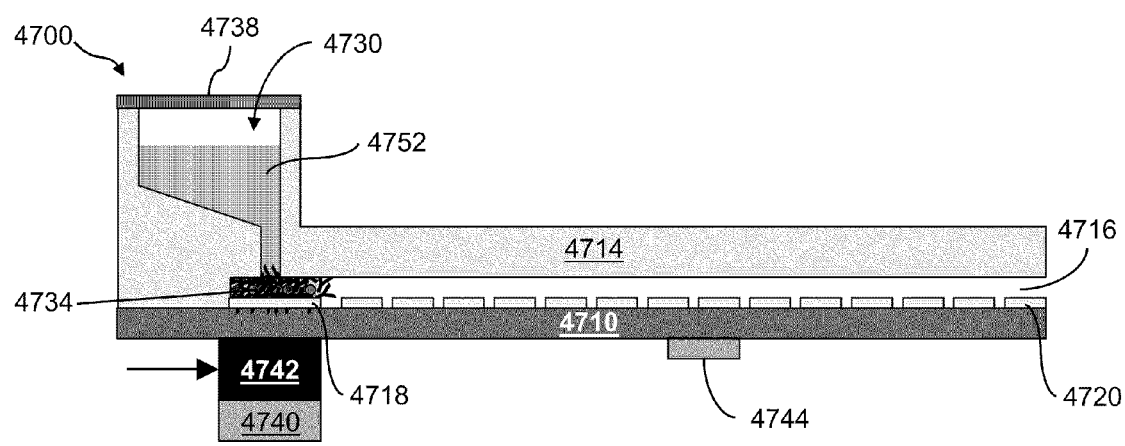

FIG. 47F shows another step in a process of concentrating and collecting a target nucleic acid from a sample fluid. In this step, sonicator 4742 is physically moved in proximity of reservoir electrode 4718, which is activated. Sonicator 4742 is activated (e.g., high energy operation) and used to vigorously agitate and mix sample fluid 4752. Sonciator 4742 may be activated for a period of time that is sufficient to provide optimum lysing of target analyte 4754 and release of nucleic acid. In another embodiment, a single sonicator may be strategically placed in a manner which permits simultaneous sonication of a droplet in the droplet operations gap and the fluid in the reservoir. In yet another embodiment, more than one sonicator may be provided.

In one example, vigorous sonication in combination with a chemical and/or enzymatic lysis reagent (i.e., lysis reagent droplet 4756) may be helpful for biological samples that include fungal pathogens.

Figure 47G:
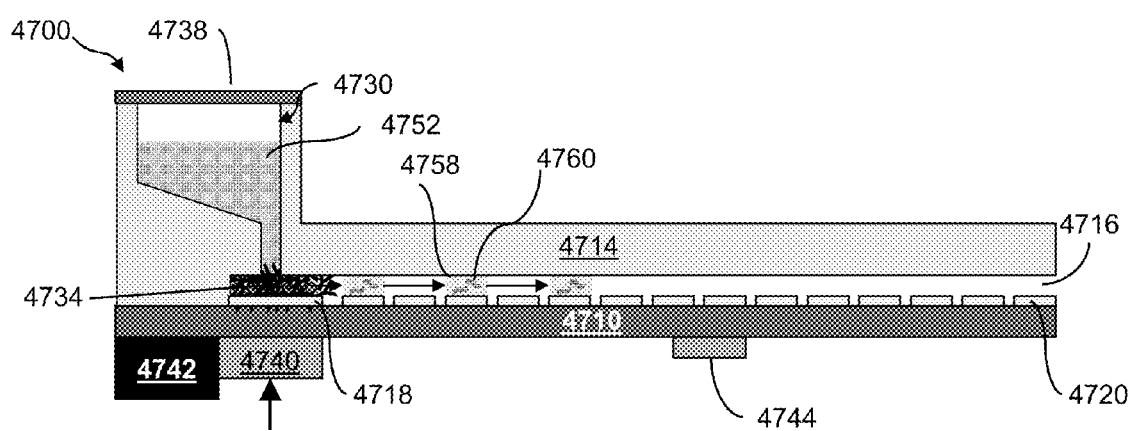

FIG. 47G shows another step in a process of concentrating and collecting a target nucleic acid from a sample fluid. In this step, the position of magnet 4740 is such that there is a certain magnetic field present at reservoir electrode 4718 of droplet actuator 4700. As a result of the magnetic field, magnetically responsive capture beads 4734 that have target analyte 4754 bound thereon settle at reservoir electrode 4718. Because target analyte 4754 has been lysed, nucleic acid is released into sample fluid 4752. One or more lysate droplets 4758 that include a quantity of target nucleic acid 4760 (e.g., DNA or RNA) are transported using droplet operations away from reservoir electrode 4718 along a path of droplet operations electrodes 4720 towards magnet 4744.

Figure 47H:
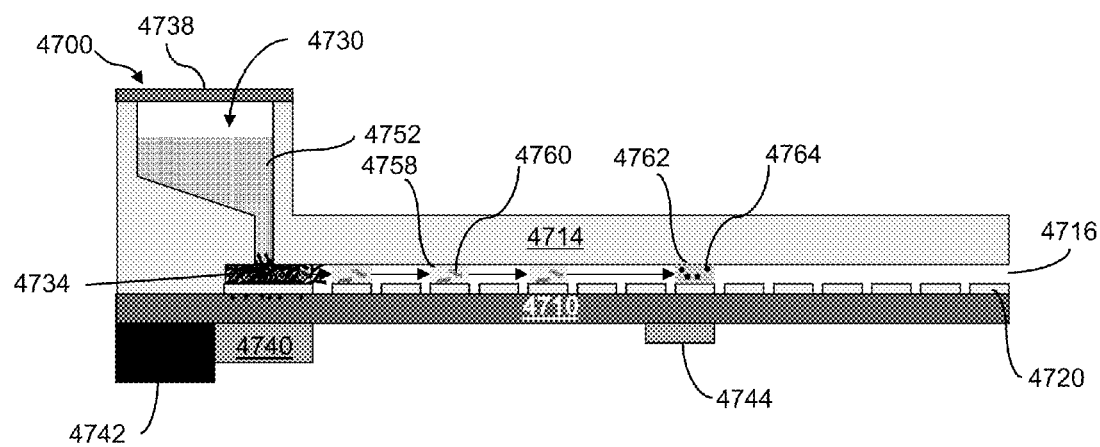

FIG. 47H shows another step in a process of concentrating and collecting a target nucleic acid from a sample fluid. In this step, a capture droplet 4762 that includes a quantity of magnetically responsive capture beads 4764 is positioned using droplet operations at second magnet 4744. Capture beads 4764 include a quantity of oligonucleotide sequences that are used to anneal to and capture target nucleic acid 4760 in lysate droplet 4758. Using droplet operations, one or more lysate droplets 4758 are transported to and merged with capture droplet 4762. In this step, target nucleic acid 4760 is further concentrated and purified.

Figure 47I:
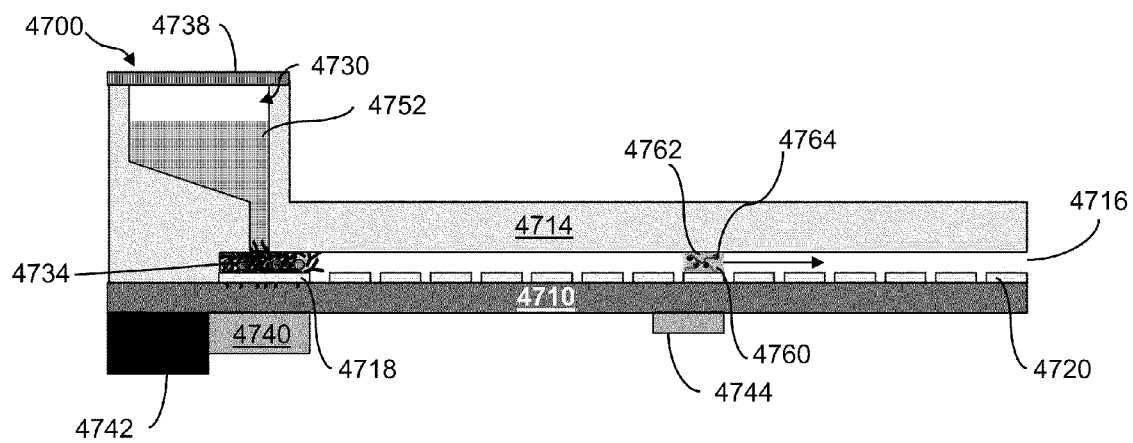

FIG. 47I shows another step in a process of concentrating and collecting a target nucleic acid from a sample fluid. In this step, capture droplet 4762 is washed using a series of droplet operations in order to remove unbound material. Bound nucleic acid 4760 in capture droplet 4762 is now ready for PCR.

In another embodiment, when target analyte 4754 is a nucleic acid, lysis steps, (i.e., FIGS. 47E and 47F) may not be required.

7.18 Sample

In various embodiments of the invention, the invention makes use of a nucleic acid sample. The nucleic acid sample is a sample that at least potentially contains a target nucleic acid or a nucleic acid coupled directly or indirectly to a target substance, such as a target molecule, cell or organism. In certain embodiments, a nucleic acid sample may be subdivided into subsamples. For example, subsample droplets may be dispensed using droplet operations from a sample droplet.

Individual subsamples may be amplified for a predetermined numbers of cycles to generate a series of endpoint measurements. The endpoint measurements may include measurements of each of the subsamples (and/or of sets of subsamples) taken after, or at the end of, of a certain predetermined number of amplification cycles. Endpoint measurements of different subsamples may be used to generate a curve that may be used to quantify the target nucleic acid present in the original sample. For example, endpoint measurements of different subsample droplets may be used to generate a curve that may be used to quantify the target nucleic acid present in the sample droplet, or the original sample from which the sample droplet was derived.

A nucleic acid sample may be a sample from a subject, a control, a standard or a replicate. The nucleic acid may be coupled to another substance, such as a target molecule, which is the actual analyte of interest. In various embodiments, a protocol may involve amplification of material from one or more subject samples, as well as amplification of one or more controls and/or replicates. In certain embodiments, a particular subsample is used to produce only a single data point. In other embodiments, multiple identical subsample droplets may be differentially amplified to produce a series of data points indicating the amount of amplification signal detected as a function of the number of amplification cycles.

Nucleic acid samples may, for example, be derived from environmental samples, such as air samples, water samples, soil samples; forensic samples, such as hair samples, skin cells, and other forensic residues; and other biological samples, such as whole blood, lymphatic liquid, serum, plasma, sweat, tear, saliva, sputum, cerebrospinal liquid, amniotic liquid, seminal liquid, vaginal excretion, serous liquid, synovial liquid, pericardial liquid, peritoneal liquid, pleural liquid, transudates, exudates, cystic liquid, bile, urine, gastric liquid, intestinal liquid, fecal samples, liquids containing single or multiple cells, liquids containing organelles, fluidized tissues, fluidized organisms, liquids containing multi-celled organisms, biological swabs and biological washes.

7.19 Detection

Various approaches to detecting amplification may be used in the practice of the invention. For example, in one embodiment each subsample droplet is subjected to a fluorescence intensity measurement at a predetermined wavelength. In one embodiment, detection is accomplished contemporaneously with the amplification reaction. In other words, while multiple subsample droplets may be amplified, as each subsample droplet completes its predetermined number of cycles, it may be subjected to detection. While one droplet is subject to detection, other droplets may continue to be amplified. In certain embodiments, a group of droplets is being amplified generally at the same time, and after each n cycles, at least one droplet is subjected to detection. The number of cycles between each detection step may be selected based on the data needs of a particular assay. In general, more accurate quantification will require detection at a greater number or fraction of the total amplification cycles.

Detection may be accomplished generally as the subsample droplets become available, i.e., as the predetermined number of cycles is complete. Subsample droplets may be tested in place or may be transported or moved elsewhere for subsequent detection. The latter approach may be useful for separating amplification and detection functions. For example, subsample droplets may be transported elsewhere on the droplet actuator and parked while they await detection. When subsample droplets are ready for detection, a sensor may scan the region in which the droplets are parked to take a measurement of each droplet. Alternatively, the subsample droplets may be transported one or more at a time into the presence of a sensor for detection. For example, each subsample droplet may be transported through a detection window, and a measurement may be taken by a sensor for each droplet while it is present in the detection window.

Droplets may be subjected to detection using various techniques. In one embodiment, the droplets may be transported into the presence of the detector. In this embodiment, one or more fixed sensors may be used to accomplish the detection. Such a configuration reduces instrument cost and complexity. In another embodiment, the sensor is moved into the presence of the droplets for detection. Droplets may be arrayed on or off the droplet actuator for detection at a later time. Arrayed droplets may be scanned or imaged by a sensor. For example, arrayed droplets may be imaged by an array detector, such as a CCD or LED/photodiode array. Droplets may be moved into the presence of the CCD or LED/photodiode array and/or the CCD or LED/photo diode array may be moved into the presence of the droplets.

As already mentioned, in certain embodiments, amplification in detection may be separated. This advantage is facilitated by the use of multiple endpoint reactions, rather than multiple measurements of the same reaction over time. This approach also facilitates the addition of detection reagent following amplification but prior to detection. The separation of thermal cycling and detection provides greater design flexibility when designing a droplet actuator capable of conducting nucleic acid application.

In various embodiments, detection reagent is added to each subsample droplet following amplification but before or during detection. For example, droplets including intercalating dyes (such as SYBR Green) and/or molecular beacons may be added to a subsample droplet following amplification. This embodiment facilitates the use of reagents that may inhibit amplification, since the reagents would be added after the amplification is complete. The reagent may be added prior to or during detection. In another embodiment, some portion of the amplification cycles may be conducted prior to addition of the detection reagent. In other words, the detection reagent may be added during or prior to one or more final cycles. This approach may be useful for detection chemistries that require the detection reagent to be present during polymerization, such as Taqman® reagents.

As noted, the separation of amplification and detection improves design flexibility for the droplet actuator and the instrumentation required for operating the droplet actuator. For example, a detector module and a heating module may exchange positions when performing their respective functions. This approach would allow heaters to be arranged on both sides of the droplet actuator without interfering with detection. In another example, a separate surface may be provided for thermal cycling and detection.

Detection may be accomplished in a matter of seconds, whereas thermal cycling may require a matter of minutes, up to an hour. Consequently, one detection instrument may be used to support multiple thermal cyclers or a bank of thermal cyclers in an instrument used for controlling thermal cycling on multiple droplet actuators. For example, an instrument may be provided having multiple slots for thermal cycling, and only one or a few slots for detection. Droplet actuators may be moved from thermal cycling slots to detection slots by a user, by robotic means, or other means.

When droplets are ready for detection, they may be arrayed in any manner suitable for the form of detection to be used. For example, they may be lined up single file or packed into a dense array. The spacing and arrangement for detection is not constrained by the requirements for thermal cycling. The ability to arrange droplets in tight 1-D arrays reduces the cost and complexity of a scanning detector. Total travel for the sensor may be reduced to a linear, one axis direction only. Similarly, a smaller CCD or LED/photodiode array may be used.

Other design advantages arise out of the different requirements for thermal cycling and detection. For example optical transparency may be required for some forms of detection, but may not be required for certain thermal cycling configurations. Thermal properties may be optimized for thermal cycling regions of a droplet actuator, while optical properties may be optimized for detection regions of the droplet actuator. Further, droplet actuators of the invention may be employed to store droplet arrays for retesting at a later time.

Among other advantages, the thermal cycling techniques of the invention facilitate amplification of a droplet without requiring a detection agent, such as a binding agent, to be present in the droplet during amplification. As noted, in some cases, sub-droplets may be dispensed from a droplet undergoing thermal cycling. The sub-droplets may exit the thermal cycling process and be combined with an appropriate detection agent, then subjected to detection. Endpoint detection schemes as described herein may also employ this technique. Each sub-droplet may be combined with a droplet including a binding agent after completing the thermal cycling process.

In certain embodiments, the methods of the invention omit thermal cycling of an amplification reaction mixture that includes sample and binding agent together. Techniques of the invention may, in certain embodiments, specifically exclude a detector operable to detect a fluorescence optical signal while the amplification reaction is in progress.

In various embodiments, where the detection agent is added after thermal cycling, agents that would otherwise interfere with nucleic acid amplification may be employed. For example, a binding agent that would inhibit thermal cycling if it were present during amplification can be used in the techniques of the invention in which the binding agent is added following amplification. Thus, in certain embodiments, the invention employs binding agents that significantly inhibit the rate of nucleic acid amplification and reagents for amplification.

In other embodiments, detection may be accomplished using labeled nucleotides. Templates may be bound to beads and amplified using a labeled nucleotide, such as fluorescent nucleotide. The labeled nucleotide may be incorporated into the amplified strands, and detection may be based on (a) depletion of the labeled nucleic acid from the droplet, and/or (b) incorporation of labeled nucleic acid into amplified strands. Bead washing techniques, such as those described in U.S. Pat. No. 7,439,014, entitled "Droplet-based Surface Modification and Washing," may, in certain embodiments, be used to wash away unbound labeled nucleotide for detection of labeled nucleotide incorporated in amplified strands. This technique may be enhanced by using fluorescent nucleotides with capture beads with internal fluorescence; the beads will amplify the fluorescence of the fluorescent nucleotides.

In yet another embodiment, DNA synthesis may be measured based on production of pyrophosphate. At each cycle, the incorporation of a deoxytrinucleotide will liberate a molecule of pyrophosphate. The amount of pyrophosphate released will be proportional to the length of the amplicon minus the length of the primers. At the end of each cycle, chemical methods may be used to detect the pyrophosphate. In some cases, sub-droplets may be dispensed from a droplet undergoing thermal cycling and subjected to testing for pyrophosphate release. The sub-droplets may exit the thermal cycling process and subjected to a pyrophosphate detection protocol.

Endpoint detection schemes as described herein may also employ this technique. Droplets may be subjected to a pyrophosphate detection protocol following after completing the thermal cycling process. In either case, the pyrophosphate detection protocol may be accomplished using droplet operations, such as those described in International Patent Publication No. WO/2007/120240, entitled "Droplet-Based Pyrosequencing," published on Oct. 25, 2007.

It will be appreciated that the various detection approaches described here may generally be used with any of the embodiments described hereafter.

7.20 Heater Bar

Figure 48A:
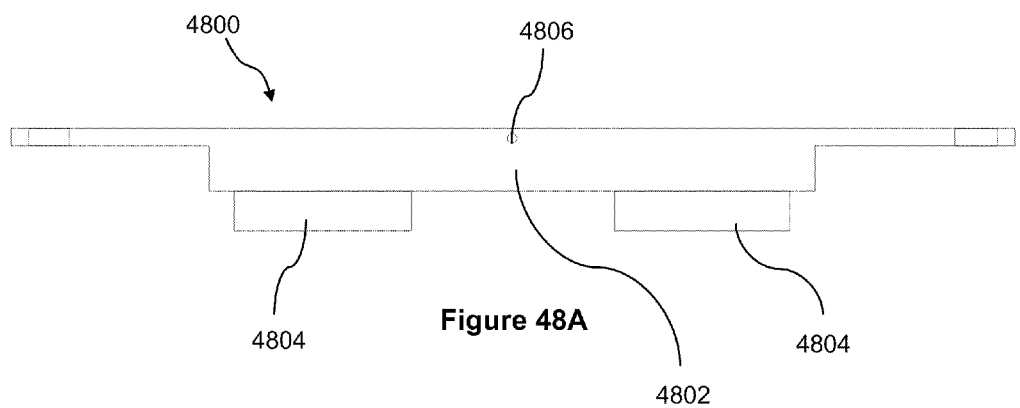
FIGS. 48A and 48B illustrate a side view of a heater bar and installed heater bar.
Figure 48B:
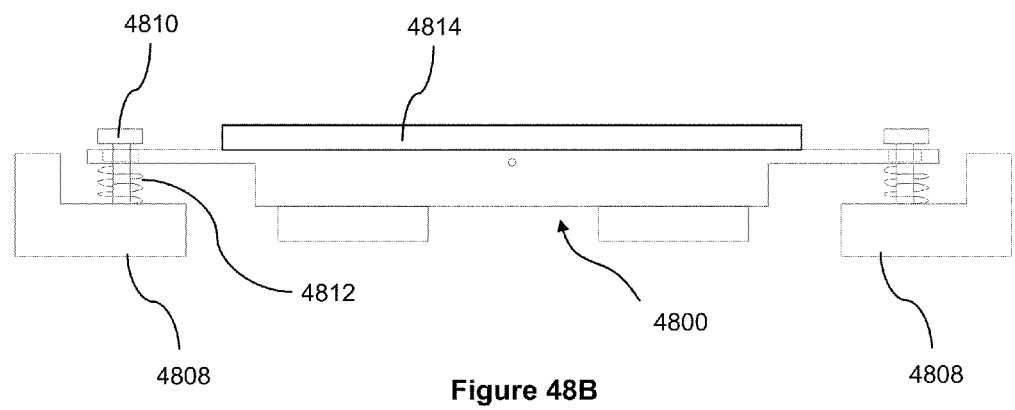

As described herein and shown in FIGS. 48A and 48B, a heater bar 4800 can be made of aluminum, such as aluminum bar 4802, for good thermal conductivity. Two resistors 4804 (15Ω each) are installed at the two ends on the bottom side to provide uniform heating. A thermistor probe 4806 can be inserted to the center of the heater bar to provide temperature measurement for the heater PID controller. The heater bar is placed on the cartridge deck 4808 using positioning screws 4810 and supported by springs 4812 underneath. The spring force ensures tight contact between the heater bar surface and the PCB cartridge 4814 to be heated. The spring-suspended heater bar does not contact the cartridge deck so the unwanted heater transfer to the deck is minimized 7.21 Systems As will be appreciated by one of skill in the art, the invention may be embodied as a method, system, or computer program product. Accordingly, various aspects of the invention may take the form of hardware embodiments, software embodiments (including firmware, resident software, microcode, etc.), or embodiments combining software and hardware aspects that may all generally be referred to herein as a "circuit," "module" or "system." Furthermore, the methods of the invention may take the form of a computer program product on a computer-usable storage medium having computer-usable program code embodied in the medium.

Any suitable computer useable medium may be utilized for software aspects of the invention. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium may even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Computer program code for carrying out operations of the invention may be written in an object oriented programming language such as Java, Smalltalk, C++ or the like. However, the computer program code for carrying out operations of the invention may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

Certain aspects of invention are described with reference to various methods and method steps. It will be understood that each method step can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the methods.

The computer program instructions may also be stored in a computer-readable memory that can direct a computer or other programmable data processing apparatus to function in a particular manner, such that the instructions stored in the computer-readable memory produce an article of manufacture including instruction means which implement various aspects of the method steps.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing various functions/acts specified in the methods of the invention.

CONCLUDING REMARKS

The foregoing detailed description of embodiments refers to the accompanying drawings, which illustrate specific embodiments of the invention. Other embodiments having different structures and operations do not depart from the scope of the invention. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the invention may be changed without departing from the scope of the invention. Furthermore, the foregoing description is for the purpose of illustration only, and not for the purpose of limitation, as the invention is defined by the claims as set forth hereinafter.

We claim:

1. A method of detecting an analyte, the method comprising:
   (a) providing a droplet in a droplet operations gap of a droplet actuator in a detection window comprising an opening or window in a substrate of the droplet actuator, the droplet comprising:
      (i) a signal-producing substance indicative of the presence and/or quantity of an analyte;
      (ii) one or more magnetically responsive beads which may interfere with signal produced by the signal producing substance;
   (b) using a magnetic field for:
      (i) magnetically removing the magnetically responsive beads from the detection window, wherein the magnetic field aggregates the magnetically responsive beads in a region of the droplet which is outside the detection window; and/or
      (ii) magnetically restricting the magnetically responsive beads from entering the detection window while transporting and/or retaining the droplet in the detection window, wherein the magnetic field aggregates the magnetically responsive beads in a region of the droplet which is outside the detection window;
   (c) detecting a signal from the droplet within the detection window produced by the signal-producing substance to detect the presence, absence and/or quantity of the analyte while the magnetically responsive beads are outside the detection window.

2. The method of claim 1 wherein,
   step 1(b) comprises providing a fixed magnet in proximity to the detection window; and
   transporting the droplet into the detection window delivers the magnetically responsive beads into sufficient proximity with the fixed magnet that the beads are pulled away from and/or restricted from entering the detection window.

3. The method of claim 1 wherein the magnetic field is generated by a magnetic field source comprising a fixed permanent magnet.

4. The method of claim 1 wherein the magnetic field is generated by a magnetic field source comprising a moveable permanent magnet.

5. The method of claim 1 wherein the magnetic field is generated by a magnetic field source comprising an electromagnet.

6. The method of claim 1 wherein the magnetic field aggregates the magnetically responsive beads at an edge of the droplet.

7. The method of claim 1 wherein the signal is produced by a fluorescent dye.

8. The method of claim 1 wherein the magnetic field attracts the magnetically responsive beads in a manner which restricts substantially all of the beads from entering or re-entering the detection window as the droplet is transported into the detection window.

9. The method of claim 1 wherein the detection window is provided in a substrate of a droplet actuator device.

10. The method of claim 9 wherein the droplet actuator comprises a plurality of paths of electrodes associated with the droplet operations substrate, each path associated with
    a detection window; and
    a magnetic field in proximity to the path, the magnetic field arranged for:
       (i) magnetically removing the magnetically responsive beads from the corresponding detection window; and/or
       (ii) magnetically restricting the magnetically responsive beads from entering the corresponding detection window while transporting into and/or retaining the droplet in the detection window.

11. The method of claim 1 wherein the one or more analytes comprise amplified nucleic acid.

12. The method of claim 1 wherein,
    the detection window is located in a substrate of a droplet actuator;
    the droplet actuator comprises temperature control zones along the path of electrodes for conducting a thermal cycling reaction; and
    the method comprises:
       (i) thermal cycling an amplification-ready droplet to yield an amplified droplet; and
       (ii) transporting the amplified droplet into the detection window.

13. The method of claim 12 comprising transporting a droplet comprising magnetically responsive beads along the path of electrodes to the path of electrodes at least partially into the detection window following 1 or more of the thermal cycles.

14. The method of claim 1 wherein the droplet is retained in place in the detection window by electrowetting while the magnetic field aggregates the magnetically responsive beads in a region of the droplet which is outside the detection window.

* * * * *